US010274484B2

(12) United States Patent
Chang et al.

(10) Patent No.: US 10,274,484 B2
(45) Date of Patent: Apr. 30, 2019

(54) MOLECULAR BIOSENSORS WITH A MODULAR DESIGN

(71) Applicant: Mediomics LLC, St. Louis, MO (US)

(72) Inventors: Yie-Hwa Chang, St. Louis, MO (US); Ling Tian, St. Louis, MO (US); Sally Tricomi, St. Louis, MO (US)

(73) Assignee: Mediomics LLC, St. Louis, MO (US)

( * ) Notice: Subject to any disclaimer, the term of this patent is extended or adjusted under 35 U.S.C. 154(b) by 253 days.

(21) Appl. No.: 14/851,788

(22) Filed: Sep. 11, 2015

(65) Prior Publication Data

US 2016/0077088 A1    Mar. 17, 2016

Related U.S. Application Data

(60) Provisional application No. 62/049,562, filed on Sep. 12, 2014.

(51) Int. Cl.
*G01N 33/542* (2006.01)

(52) U.S. Cl.
CPC ................................ *G01N 33/542* (2013.01)

(58) Field of Classification Search
CPC .. C12Q 1/68; C12M 1/00; C12M 1/34; G01N 33/566; C40B 30/04
See application file for complete search history.

(56) References Cited

U.S. PATENT DOCUMENTS

| | | |
|---|---|---|
| 4,894,347 A | 1/1990 | Hillyard et al. |
| 5,270,163 A | 12/1993 | Gold et al. |
| 5,475,096 A | 12/1995 | Gold et al. |
| 5,476,766 A | 12/1995 | Gold et al. |
| 5,543,293 A | 8/1996 | Gold et al. |
| 5,567,588 A | 10/1996 | Gold et al. |
| 5,582,981 A | 12/1996 | Toole et al. |
| 5,637,459 A | 6/1997 | Burke et al. |
| 5,641,629 A | 6/1997 | Pitner et al. |
| 5,650,275 A | 7/1997 | Pitner et al. |
| 5,660,985 A | 8/1997 | Pieken et al. |
| 5,670,637 A | 9/1997 | Gold et al. |
| 5,683,867 A | 11/1997 | Biesecker et al. |
| 5,688,935 A | 11/1997 | Stephens et al. |
| 5,696,249 A | 12/1997 | Gold et al. |
| 5,705,337 A | 1/1998 | Gold et al. |
| 5,712,375 A | 1/1998 | Jensen et al. |
| 5,723,289 A | 3/1998 | Eaton et al. |
| 5,723,592 A | 3/1998 | Eaton et al. |
| 5,750,342 A | 5/1998 | Stephens et al. |
| 5,756,291 A | 5/1998 | Griffin et al. |
| 5,763,566 A | 6/1998 | Jensen et al. |
| 5,763,595 A | 6/1998 | Gold et al. |
| 5,773,598 A | 6/1998 | Burke et al. |
| 5,789,157 A | 8/1998 | Jensen et al. |
| 5,789,160 A | 8/1998 | Eaton et al. |
| 5,817,785 A | 10/1998 | Gold et al. |
| 5,840,867 A | 11/1998 | Toole et al. |
| 5,843,653 A | 12/1998 | Gold et al. |
| 5,853,984 A | 12/1998 | Davis et al. |
| 5,858,660 A | 1/1999 | Eaton et al. |
| 5,861,254 A | 1/1999 | Schneider et al. |
| 5,864,026 A | 1/1999 | Jensen et al. |
| 5,874,218 A | 2/1999 | Drolet et al. |
| 5,958,691 A | 9/1999 | Pieken et al. |
| 5,962,219 A | 10/1999 | Gold et al. |
| 5,989,823 A | 11/1999 | Jayasena et al. |
| 5,998,142 A | 12/1999 | Gold et al. |
| 6,001,570 A | 12/1999 | Grossman |
| 6,001,577 A | 12/1999 | Gold et al. |
| 6,011,020 A | 1/2000 | Gold et al. |
| 6,013,443 A | 1/2000 | Heilig et al. |
| 6,024,918 A | 2/2000 | Hendriks et al. |
| 6,030,776 A | 2/2000 | Eaton et al. |
| 6,048,698 A | 4/2000 | Eaton et al. |
| 6,083,696 A | 7/2000 | Biesecker et al. |
| 6,110,900 A | 8/2000 | Gold et al. |
| 6,114,120 A | 9/2000 | Jensen et al. |
| 6,127,119 A | 10/2000 | Stephens et al. |
| 6,147,204 A | 11/2000 | Gold et al. |
| 6,177,555 B1 | 1/2001 | Jayasena et al. |
| 6,207,388 B1 | 3/2001 | Grossman |
| 6,225,058 B1 | 5/2001 | Munishkin et al. |
| 6,261,774 B1 | 7/2001 | Pagratis et al. |
| 6,261,783 B1 | 7/2001 | Jayasena et al. |
| 6,287,772 B1 | 9/2001 | Stefano et al. |
| 6,291,184 B1 | 9/2001 | Gold et al. |
| 6,300,074 B1 | 10/2001 | Gold et al. |
| 6,329,145 B1 | 12/2001 | Janjic et al. |

(Continued)

FOREIGN PATENT DOCUMENTS

JP    2003-508729 A    3/2003
WO    1997/00446 A1    1/1997

(Continued)

OTHER PUBLICATIONS

Li et al., "Molecular Aptamer Beacons for Real-Time Protein Recognition," Biochem. and Biophys. Res. Commun., 2002, pp. 31-40, vol. 292, No. 1.
Lipovsek et al., "In-vitro protein evolution by ribosome display and mRNA display," J. Immun. Methods, 2004, pp. 51-67, vol. 290.
Mathis, "Probing Molecular Interactions with Homogeneous Techniques Based on Rare Earth Cryptrates and Fluorescence Energy Transfer," Clinic. Chem., 1995, pp. 1391-1397, vol. 41, No. 9.
Matlock et al., "Sequence Determinants for the Recognition of the Fork Junction DNA Containing the -10 Region of Promoter DNA by E. coli RNA Polymerase," Biochem., 2000, pp. 12274-12283, vol. 39, No. 40.

(Continued)

*Primary Examiner* — Narayan K Bhat
(74) *Attorney, Agent, or Firm* — Polsinelli PC

(57) ABSTRACT

The invention generally provides molecular biosensors with modular epitope binding constructs. The molecular biosensors are useful in several methods including in the identification and quantification of target molecules.

25 Claims, 19 Drawing Sheets
(3 of 19 Drawing Sheet(s) Filed in Color)
Specification includes a Sequence Listing.

(56) References Cited

U.S. PATENT DOCUMENTS

| | | |
|---|---|---|
| 6,331,398 B1 | 12/2001 | Gold et al. |
| 6,344,318 B1 | 2/2002 | Gold et al. |
| 6,376,190 B1 | 4/2002 | Gold et al. |
| 6,380,377 B1 | 4/2002 | Dattagupta |
| 6,391,593 B1 | 5/2002 | Weston et al. |
| 6,399,302 B1 | 6/2002 | Lannigan et al. |
| 6,423,493 B1 | 7/2002 | Gorenstein et al. |
| 6,451,588 B1 | 9/2002 | Egholm et al. |
| 6,465,188 B1 | 10/2002 | Gold et al. |
| 6,506,887 B1 | 1/2003 | Smith et al. |
| 6,511,809 B2 | 1/2003 | Baez et al. |
| 6,544,746 B2 | 4/2003 | Heyduk |
| 6,566,495 B1 | 5/2003 | Fodor et al. |
| 6,593,091 B2 | 7/2003 | Keys et al. |
| 6,613,526 B2 | 9/2003 | Heilig et al. |
| 6,680,377 B1 | 1/2004 | Stanton et al. |
| 6,716,583 B2 | 4/2004 | Gold et al. |
| 6,730,482 B2 | 5/2004 | Gold et al. |
| 6,815,164 B2 | 11/2004 | Kurn |
| 6,878,515 B1 | 4/2005 | Landegren |
| 6,916,613 B2 | 7/2005 | Munishkin et al. |
| 7,125,660 B2 | 10/2006 | Stanton et al. |
| 7,172,865 B2 | 2/2007 | Heyduk |
| 7,282,328 B2 | 10/2007 | Kong et al. |
| 7,306,904 B2 | 12/2007 | Landegren et al. |
| 7,419,835 B2 | 9/2008 | Torres et al. |
| 7,435,542 B2 | 10/2008 | Shi et al. |
| 7,576,192 B2 | 8/2009 | Heyduk |
| 7,795,009 B2 | 9/2010 | Heyduk |
| 7,811,809 B2 | 10/2010 | Heyduk et al. |
| 7,939,313 B2 | 5/2011 | Heyduk et al. |
| 8,431,388 B2 | 4/2013 | Heyduk |
| 8,592,202 B2 | 11/2013 | Heyduk et al. |
| 8,945,840 B2 | 2/2015 | Heyduk et al. |
| 8,956,857 B2 | 2/2015 | Heyduk et al. |
| 8,993,245 B2 | 3/2015 | Heyduk et al. |
| 9,040,287 B2 | 5/2015 | Chang et al. |
| 9,618,505 B2 | 4/2017 | Heyduk |
| 9,671,403 B2 | 6/2017 | Heyduk |
| 9,797,892 B2 | 10/2017 | Chang |
| 9,951,376 B2 | 4/2018 | Heyduk |
| 2002/0022224 A1 | 2/2002 | Hornby et al. |
| 2002/0037506 A1 | 3/2002 | Lin et al. |
| 2002/0051986 A1 | 5/2002 | Baez et al. |
| 2002/0064779 A1 | 5/2002 | Landegren et al. |
| 2003/0087239 A1 | 5/2003 | Stanton et al. |
| 2003/0207271 A1 | 11/2003 | Holwitt et al. |
| 2003/0224435 A1 | 12/2003 | Seiwert et al. |
| 2003/0232383 A1 | 12/2003 | Daunert et al. |
| 2003/0232388 A1 | 12/2003 | Kreimer et al. |
| 2004/0053310 A1 | 3/2004 | Shi et al. |
| 2004/0058378 A1 | 3/2004 | Kong et al. |
| 2004/0067501 A1 | 4/2004 | Kage |
| 2004/0180360 A1 | 9/2004 | Wilson et al. |
| 2004/0219523 A1 | 11/2004 | Stanton et al. |
| 2005/0009050 A1 | 1/2005 | Nadeau et al. |
| 2005/0069910 A1 | 3/2005 | Turner et al. |
| 2005/0089890 A1 | 4/2005 | Cubicciotti |
| 2005/0089899 A1 | 4/2005 | Cubicciotti |
| 2005/0095627 A1 | 5/2005 | Kolman et al. |
| 2005/0106594 A1 | 5/2005 | Ellington et al. |
| 2005/0112710 A1 | 5/2005 | Torres et al. |
| 2005/0221408 A1 | 10/2005 | Nalefski et al. |
| 2006/0110739 A1 | 5/2006 | Heyduk et al. |
| 2007/0154899 A1 | 7/2007 | Coull et al. |
| 2007/0287197 A1 | 12/2007 | Harris et al. |
| 2008/0044826 A1 | 2/2008 | Heyduk |
| 2008/0044834 A1 | 2/2008 | Heyduk |
| 2008/0171322 A1 | 7/2008 | Heyduk et al. |
| 2009/0202990 A1 | 8/2009 | Heyduk et al. |
| 2010/0021899 A1 | 1/2010 | Ikebukuro et al. |
| 2010/0297654 A1 | 11/2010 | Heyduk |
| 2011/0091893 A1 | 4/2011 | Heyduk et al. |
| 2012/0028242 A1 | 2/2012 | Heyduk et al. |
| 2013/0034846 A1 | 2/2013 | Chang et al. |
| 2014/0243208 A1 | 8/2014 | Chang et al. |
| 2014/0248710 A1 | 9/2014 | Heyduk et al. |
| 2015/0191779 A1 | 7/2015 | Heyduk et al. |
| 2015/0219668 A1 | 8/2015 | Heyduk et al. |
| 2015/0226739 A1 | 8/2015 | Heyduk et al. |
| 2015/0253315 A1 | 9/2015 | Chang et al. |
| 2017/0269082 A1 | 9/2017 | Heyduk |
| 2018/0011087 A1 | 1/2018 | Chang |

FOREIGN PATENT DOCUMENTS

| | | |
|---|---|---|
| WO | 2000/70329 A1 | 11/2000 |
| WO | 2003/064657 A1 | 8/2003 |
| WO | 2003/078449 A2 | 9/2003 |
| WO | 2005/059509 A2 | 6/2005 |
| WO | 2006/128138 A2 | 11/2006 |
| WO | 2006/135527 A2 | 12/2006 |
| WO | 2007/005649 A2 | 1/2007 |
| WO | 2008/108873 A2 | 9/2008 |
| WO | 2010/059820 A1 | 5/2010 |
| WO | 2011/100561 A1 | 8/2011 |
| WO | 2013016280 A2 | 1/2013 |
| WO | 2016/040830 A1 | 3/2016 |

OTHER PUBLICATIONS

Mills et al., "Flexibility of Single-Stranded DNA: Use of Gapped Duplex Helices to Determine the Persistence Lengths of Poly(dT) and Poly(dA)," J. Mol. Biol., 1999, pp. 245-257, vol. 285.

Minutes of Oral Proceedings dated May 20, 2010 from related European Patent Application No. 04813618.8, 5 pgs.

Notice of Allowance from related Chinese Patent Application No. 200480036874.7, dated Feb. 29, 2012; 3 pgs.

Notice of Allowance and Interview Summary from related U.S. Appl. No. 12/830,958, dated Dec. 20, 2012; 16 pgs.

Notice of Allowance from related U.S. Appl. No. 12/961,135, dated Jul. 24, 2013; 10 pgs.

Notice of Allowance from related U.S. Appl. No. 13/133,198, dated Aug. 28, 2014; 13 pgs.

Notice of Allowance from related U.S. Appl. No. 11/916,776, dated Aug. 5, 2014; 7 pgs.

Notice of Allowance from related U.S. Appl. No. 13/728,226, dated Jun. 16, 2014; 21 pgs.

Notice of Allowance from related Canadian Patent Application No. 2,611,198, dated Aug. 19, 2014; 1 page.

Office Action from related European Patent Application No. 06770407.2, dated Apr. 4, 2011; 3 pgs.

Office Action from related European Patent Application No. 04813618.8, dated Dec. 18, 2008; 3 pgs.

Office Action from related European Patent Application No. 04813618.8, dated Jul. 1, 2008; 3 pgs.

Office Action from related European Patent Application No. 07873908.3, dated Jan. 4, 2012; 3 pgs.

Office Action from related European Patent Application No. 07873908.3, dated Oct. 26, 2010; 5 pgs.

Office Action from related Chinese Patent Application No. 200480036874.7, dated Aug. 9, 2010; 23 pgs.

Office Action from related Chinese Patent Application No. 200480036874.7, dated Jan. 19, 2011; 12 pgs.

Office Action from related Chinese Patent Application No. 200480036874.7, dated Jun. 23, 2011; 9 pgs.

Office Action from related Chinese Patent Application No. 200780037379.1 dated Oct. 10, 2011; 14 pgs.

Office Action from related Chinese Patent Application No. 200780037379.1 dated Jul. 10, 2012; 8 pgs.

Office Action from related Chinese Patent Application No. 200980146720.6, dated May 27, 2013; 18 pgs.

Office Action from related Chinese Patent Application No. 200980146720.6, dated Dec. 10, 2013; 34 pgs.

Office Action from related Chinese Patent Application No. 200980146720.6, dated May 20, 2014; 25 pgs.

Office Action from related Japanese Patent Application No. 2006-543991, dated Feb. 23, 2010; 6 pgs.

(56) References Cited

OTHER PUBLICATIONS

Office Action from related Japanese Patent Application No. 2006-543991, dated Nov. 24, 2010; 4 pgs.
Office Action from related Japanese Patent Application No. 2011-284014, dated Jul. 29, 2014; 1 page (English Translation only).
Office Action from related Japanese Patent Application No. 2011-284014, dated Oct. 8, 2013; 2 pgs. (English Translation only).
Office Action from related Canadian Patent Application No. 2,545,006, dated Feb. 3, 2011; 5 pgs.
Office Action from related Canadian Patent Application No. 2,660,129, dated Aug. 21, 2013; 3 pgs.
Office Action from related Canadian Patent Application No. 2,787,483, dated Feb. 19, 2014; 3 pgs.
Office Action from related Canadian Patent Application No. 2,611,198, dated Aug. 30, 2013; 2 pgs.
Office Action from related Canadian Patent Application No. 2,744,003, dated Dec. 27, 2013; 2 pgs.
Office Action from related Canadian Patent Application No. 2,611,198, dated Nov. 20, 2012; 3 pgs.
Office Action from related Canadian Patent Application No. 2,744,003, dated Mar. 26, 2013; 3 pgs.
Office Action from related Indian Patent Application No. 1337/CHENP/2009, dated Nov. 27, 2013; 4 pgs.
Office Action from related U.S. Appl. No. 12/961,135, dated Dec. 1, 2011; 23 pgs.
Office Action from related U.S. Appl. No. 12/961,135, dated Jun. 17, 2011; 17 pgs.
Office Action from related U.S. Appl. No. 10/539,107, dated Dec. 18, 2009; 22 pgs.
Office Action from related U.S. Appl. No. 10/539,107, dated Jul. 2, 2008; 21 pgs.
Office Action from related U.S. Appl. No. 10/539,107 dated Mar. 12, 2009; 23 pgs.
Office Action from related U.S. Appl. No. 11/916,776, dated Jun. 14, 2010; 9 pgs.
Office Action from related U.S. Appl. No. 11/916,776, dated Jun. 30, 2011; 12 pgs.
Office Action from related U.S. Appl. No. 11/836,339, dated Sep. 14, 2009; 16 pgs.
Office Action from related U.S. Appl. No. 11/836,339, dated Mar. 8, 2010; 14 pgs.
Office Action from related U.S. Appl. No. 11/836,333, dated Sep. 30, 2009; 32 pgs.
Office Action from related U.S. Appl. No. 12/830,958, dated May 8, 2012; 21 pgs.
Oligonucleotide Modifications (TriLink Products) screen from http://www.trilinkbiotech.com/products/oligo/details_modifications.asp?ProducUD=133, printed Sep. 8, 2009; 1 page.
Abravaya et al., "Detection of point mutations with a modified ligase chain reaction (Gap-LCR)," Nucleic Acids Research, 1995, pp. 675-682, vol. 23, No. 4.
Bevan et al., "Sequencing of PCR-amplified DNA," PCR Methods and Applications, Genome Res., 1992, pp. 222-228, vol. 1.
Bock et al., "Selection of single-stranded DNA molecules that bind and inhibit human thrombin," Nature, 1992, pp. 564-566, vol. 355.
Boder et al., "Yeast surface display for screening combinatorial polypeptide libraries," Nat. Biotech., 1997, pp. 553-557, vol. 15.
Burgstaller et al., "Synthetic Ribozymes and the First Deoxyribozyme," Angew. Chem. Int. Ed. Engl., 1995, pp. 1189-1192, vol. 34, No. 11.
Chemical bond, http://en.wikipedia.org/wiki/Chemical_bond, printed Jun. 24, 2008; 11 pgs.
Daniels et al., "Generation of RNA Aptamers to the G-Protein-Coupled Receptor for Neurotensin, NTS-1," Analytical Biochemstry, 2002, pp. 214-226, vol. 305.
Decision of Refusal dated Aug. 23, 2011 from related Japanese Patent Application No. 2006 543991; 6 pgs.
Decision on Oral Proceedings dated May 26, 2010 from related European Patent Application No. 04813618.8; 7 pgs.
Decision to Grant dated Sep. 5, 2013 from related European Patent Application No. 07873908.3; 2 pgs.
Decision to Grant dated Nov. 14, 2011 from related European Patent Application No. 06770407.2; 5 pgs.
Ellington et al., "In vitro selection of RNA molecules that bind specific ligands," Nature, 1990, pp. 818-822, vol. 346.
Extended European Search Report from related European Patent Application No. 078739083, dated Dec. 22, 2009; 6 pgs.
Supplementary Search Report from related European Patent Application No. 04813618.8, dated Apr. 23, 2008; 2 pgs.
Extended European Search Report from related European Patent Application No. 06770407.2, dated Jul. 9, 2010; 4 pgs.
Extended European Search Report from related European Patent Application No. 13194822.6, dated Jan. 17, 2014; 6 pgs.
Extended European Search Report from related European Patent Application No. 11742872.2, dated Aug. 23, 2013; 6 pgs.
Famulok et al., "In Vitro Selection of Specific Ligand Binding Nucleic Acids," Angew. Chem. Int. Ed. Engl., 1992, pp. 979-988, vol. 31.
Famulok et al., "Selection of Functional RNA and DNA Molecules from Randomized Sequences," Nucl. Acids and Mol. Biol., 1993, pp. 271-284, vol. 7.
Fang et al., "Synthetic DNA Aptamers to Detect Protein Molecular Variants in a High-Throughput Fluorescence Quenching Assay," ChemBioChem, 2003, pp. 829-834, vol. 4.
Francisco et al., "Production and fluorescence-activated cell sorting of *Escherichia coli* expressing a functional antibody fragment on the external surface," Proc. Natl. Acad. Sci. USA, 1993, pp. 10444-10448, vol. 90, No. 22.
Fredriksson et al., "Protein Detection Using Proximity-dependent DNA Ligation Assays," Nature Biotechnology, 2002, pp. 473-477, vol. 20.
Fried et al., "Equilibria and kinetics of lac repressor-operator interactions by polyacrylamide gel electrophoresis," Nucl. Acid Res., 1981, pp. 6505-6525, vol. 9, No. 23.
Georgiou et al., "Display of heterologous proteins on the surface of microorganisms: From the screening of combinatorial libraries to live recombinant vaccines," Nat. Biotech., 1997, pp. 29-34, vol. 15.
Gold et al., "Diversity of Oligonucleotide Functions," Ann. Rev. Biochem., 1995, pp. 763-797, vol. 64.
Hamaguchi et al., "Aptamer Beacons for the Direct Detection of Proteins," Analyt. Biochem., 2001, pp. 126-131, vol. 294.
Hanes et al., "In vitro selection and evolution of functional proteins by using ribosome display," Proc. Natl. Acad. Sci. USA, 1997, pp. 4937-4942, vol. 94.
Heyduk et al., "Nucleic Acid-Based Fluorescence Sensors for Detecting Proteins," Anal. Chem., 2005, pp. 1147-1156, vol. 77, No. 4.
Heyduk et al., "Conformational Changes of DNA Induced by Binding of Chironomus High Mobility Group Protein 1a (cHMG1a)," J. Biol. Chem., 1997, pp. 19763-19770, vol. 272, No. 32.
Heyduk et al., "Homogeneous fluorescence assay for cyclic AMP," Combinatorial Chemistry & High Throughput Screening, 2003, pp. 347-354, vol. 6, No. 4.
Heyduk et al., "Thiol-reactive, Luminescent Europium Chelates: Luminescence Probes for Resonance Energy Transfer Distance Measurements in Biomolecules," Anal. Biochem., 1997, pp. 216-227, vol. 248.
Heyduk et al., "Molecular beacons for detecting DNA binding proteins:mechanism of action," Analyt. Biochem., 2003, pp. 1-10, vol. 316.
Heyduk et al., "Luminescense Energy Transfer with Lanthanide Chelates: Interpretation of Sensitized Acceptor Decay Amplitudes," Analyt. Biochem., 2001, pp. 60-67, vol. 289, No. 1.
Heyduk et al., "Molecular beacons for detecting DNA binding proteins," Nat. Biotech., 2002, pp. 171-176, vol. 20.
Heyduk et al., "Molecular Pincers: Antibody-Based Homogeneous Protein Sensors," Anal. Chem., 2008, pp. 5152-5159, vol. 80, No. 13.
Heyduk et al., "Fluorescent homogenous immunosensors for detecting pathogenic bacteria," Anal. Biochem., 2010, pp. 298-303, vol. 396, No. 2.
Heyduk, "Practical biophysics: Sensors for rapid detection of biological targets utilizing target-induced oligonucleotide annealing," Biophysical Chemistry, 2010, pp. 91-95, vol. 151, No. 3.

(56) References Cited

OTHER PUBLICATIONS

Hosse et al., "A new generation of protein display scaffolds for molecular recognition," Protein Science, 2006, pp. 14-27, vol. 15.
HyTher—Hibridization Thermodynamics—Module 1, http://ozone3.chem.wayne.edu/cgi-bin/login/execs/HytherMI.cgi, printed Mar. 5, 2009; 1 page.
International Search Report and Written Opinion from related International Patent Application No. PCT/US2007/075560, dated Aug. 25, 2008; 10 pgs.
International Search Report and Written Opinion from related International Patent Application No. PCT/US2006/018845, dated Aug. 3, 2007; 8 pgs.
International Search Report and Written Opinion from related International Patent Application No. PCT/US2009/065142, dated Jan. 20, 2010; 7 pgs.
International Search Report and Written Opinion from related International Patent Application No. PCT/US2004/041315, dated Sep. 24, 2007; 6 pgs.
International Search Report and Written Opinion from related International Patent Application No. PCT/US2012/047840, dated Jan. 11, 2013; 19 pgs.
Jayasena, "Aptamers: An Emerging Class of Molecules That Rival Antibodies in Diagnostics," Clinical Chemistry, 1999, pp. 1628-1650, vol. 45, No. 9.
Jeppesen et al., "Impact of Polymer Tether Length on Multiple Ligand-Receptor Bond Formation," Science, 2001, pp. 465-468, vol. 293.
Keefe et al., "Functional proteins from a random-sequence library," Nature, 2001, pp. 715-718, vol. 410, No. 6829.
Klug et al., "All you wanted to know about SELEX (but were afraid to ask . . . )", Mol. Biol. Reports, 1994, pp. 97-107, vol. 20.
Knoll et al., "Unimolecular Beacons for the Detection of DNA-Binding Proteins," Anal. Chem., 2004, pp. 1156-1164, vol. 76, No. 4.
Lass-Napiorkowska et al., "Detection Methodology Based on Target Molecule-Induced Sequence-Specific Binding to a Single-Stranded Oligonucleotide," Anal. Chem., 2012, pp. 3382-3389, vol. 84.
Notice of Allowance from related U.S. Appl. No. 11/916,776, dated Sep. 19, 2014; 16 pgs.
Notice of Allowance from related U.S. Appl. No. 13/728,226, dated Oct. 1, 2014; 8 pgs.
Notice of Allowance from related U.S. Appl. No. 13/133,198, dated Nov. 18, 2014; 15 pgs.
Notice of Allowance from related U.S. Appl. No. 13/578,718, dated Jan. 27, 2015; 13 pgs.
Supplemental Notice of Allowability from related U.S. Appl. No. 13/578,718, dated Mar. 5, 2015; 4 pgs.
Office Action from related Chinese Patent Application No. 201280038577.0 dated Jul. 7, 2015; 14 pgs.
Office Action from related Chinese Patent Application No. 201280038577.0, dated Nov. 3, 2014; 12 pgs.
Office Action from related Canadian Patent Application No. 2,787,483, dated Mar. 19, 2015; 4 pgs.
Office Action from related U.S. Appl. No. 13/133,198, dated Nov. 5, 2012; 12 pgs.
OPffice Action from related U.S. Appl. No. 13/133,198, dated Jun. 27, 2013; 14 pgs.
Office Action from related European Patent Application No. 11742872.2, dated May 19, 2014; 3 pgs.
Stoltenburg et al., "SELEX—A (r)evolutionary method to generate high-affinity nucleic acid ligands," Biomolecular Engineering, 2007, pp. 381-403, vol. 24, No. 4.
Supplementary European Search Report from related European Patent Application No. 12817830.8, dated Nov. 25, 2014; 11 pgs.
Darmanis et al., "Self-assembly of proximity probes for flexible and modular proximity ligation assays," BioTechniques, 2007, pp. 443-450, vol. 43, No. 4.
International Search Report and Written Opinion from related International Patent Application No. PCT/US2011/024547, dated Jun. 28, 2011; 10 pages.
International Search Report and Written Opinion from related International Patent Application No. PCT/US2015/049733, dated Jan. 29, 2016; 15 pages.
Notice of Allowance from related Canadian Patent Application No. 2,660,129, dated Feb. 10, 2015; 1 page.
Office Action from related European Patent Application No. 03703998.9, dated Jan. 8, 2015; 3 pages.
Office Action from related European Patent Application No. 03703998.9, dated May 30, 2012; 3 pages.
Office Action from related U.S. Appl. No. 11/609,628, dated Oct. 1, 2008; 5 pages.
Office Action from related European Patent Application No. 11742872.2, dated Apr. 2, 2015; 4 pages.
Office Action from related U.S. Appl. No. 13/578,718, dated Sep. 13, 2013; 25 pages.
Office Action from related U.S. Appl. No. 13/578,718, dated Feb. 21, 2014; 33 pages.
Office Action from related U.S. Appl. No. 14/234,329, dated Aug. 7, 2015; 10 pages.
Office Action from related U.S. Appl. No. 14/234,329, dated Apr. 1, 2016; 10 pages.
Office Action from related U.S. Appl. No. 13/728,226, dated Jan. 10, 2014; 30 pages.
Office Action from related U.S. Appl. No. 13/578,718, dated Nov. 5, 2014; 21 pages.
Office Action from related European Patent Application No. 13194822.6, dated Dec. 19, 2014; 4 pages.
Office Action from related U.S. Appl. No. 14/623,348, dated Jun. 17, 2016; 21 pages.
Office Action dated Sep. 8, 2011 from related Chinese Patent Application No. 200480036874.7, 5 pages with English translation.
Supplementary European Search Report dated Jun. 11, 2010 from elated EP Application No. EP 06770407, 1 page.
European Search Report dated Nov. 16, 2009, from related Application No. EP 07873908, 2 pages.
Final Office Action dated Aug. 3, 2010 from related U.S. Appl. No. 11/836,339, 13 pages.
Office Action dated May 30, 2016 from related Canadian Patent Application No. 2,787,483; 3 pages.
Office Action from related U.S. Appl. No. 14/234,329, dated Nov. 16, 2016; 13 pages.
Notice of Allowance dated Nov. 25, 2016 from related U.S. Appl. No. 14/623,348; 14 pages.
Office Action from related U.S. Appl. No. 14/673,336, dated Aug. 8, 2016; 60 pages.
Notice of Allowance dated Jan. 31, 2017 from related U.S. Appl. No. 14/673,336; 10 pages.
Office Action from related U.S. Appl. No. 14/719,867, dated Nov. 8, 2016; 68 pages.
Notice of Allowance dated Apr. 24, 2017 from related U.S. Appl. No. 14/719,867; 10 pages.
Order Rescheduling Oral Proceedings dated Jan. 28, 2014 from related European Patent Application No. 04813618.8; 1 page.
Ozawa et al., "Identification and Characterization of Peptides Binding to Newcastle Disease Virus by Phage Display," J. Vet Med. Sci., 2005, pp. 1237-1241, vol. 67, No. 12.
Ratilainen et al., "Hybridization of Peptide Nucleic Acid," Biochemistry, 1998, pp. 12331-12342, vol. 37.
Request for Postponement of Oral Proceedings dated Jan. 27, 2014 from related European Patent Application No. 04813618.8; 1 page.
Response to Communication Under Article 15(1) of the Rules of Procedure of the Board of Appeals dated Aug. 1, 2014 from related European Patent Application No. 04813618.8; 8 pgs.
Result of Telephone Consultation with Examiner dated Apr. 13, 2010 from related European Patent Application No. 04813618.8; 3 pgs.
Roberts et al., "RNA-peptide fusions for the in vitro selection of peptides and proteins," PNAS, 1997, pp. 12297-12302, vol. 94, No. 23.

(56) References Cited

OTHER PUBLICATIONS

Rockett et al., "DNA arrays: technology, options and toxicological applications," Xenobiotics, 2000, pp. 155-177, vol. 30, No. 2.

Santalucia et al., "Improved Nearest-Neighbor Parameters for Predicting DNA Duplex Stability," Biochemistry, 1996, pp. 3555-3562, vol. 35, No. 11.

Santalucia, "A unified view of polymer, dumbbell, and oligonucleotide DNA nearest-neighbor thermodynamics," PNAS, 1998, pp. 1460-1465, vol. 95.

Sayer et al., "Structural characterization of a 2'F-RNA aptamer that binds a HIV-1 SU glycoprotein, g120," Biochem. and Biophys. Res. Comm., 2002, pp. 924-931, vol. 293, No. 3.

Selvin et al., "Luminescence energy transfer using a terbium chelate: Improvements on fluorescence energy transfer," Proc. Natl. Acad. Sci. USA, 1994, pp. 10024-10028, vol. 91.

Selvin et al., "Luminescence Resonance Energy Transfer," J. Am. Chem. Soc., 1994, pp. 6029-6030, vol. 116.

Sen et al., "On the stability of peptide nucleic acid duplexes in the presence of organic solvents," Nucleic Acids Research, 2007, pp. 3367-3374, vol. 35, No. 10.

Sequence alignment brochure SEQ ID No. 1 and 2, http://blast.ncbi.nlm.nih.gov/Blast.cgi, printed Sep. 13, 2009; 4 pgs.

Sequence alignment brochure SEQ ID No. 1 and 3, http://blast.ncbi.nlm.nih.gov/Blast.cgi, printed Sep. 15, 2009; 4 pgs.

Sequence alignment brochure SEQ ID No. 2 and 3, http://blast.ncbi.nlm.nih.gov/Blast.cgi, printed Sep. 13, 2009; 4 pgs.

Sequence alignment brochure SEQ ID No. 5 and 12, http://blast.ncbi.nlm.nih.gov/Blast.cgi, printed Sep. 13, 2009; 4 pgs.

Sequence alignment brochure SEQ ID No. 7 and 12, http://blast.ncbi.nlm.nih.gov/Blast.cgi, printed Sep. 15, 2009; 4 pgs.

Statement of Grounds for Appeal dated Oct. 15, 2010 form related European Patent Application No. 04813618.8; 22 pgs.

Summons to Oral Proceedings dated Dec. 19, 2013 from related European Patent Application No. 04813618.8; 1 page.

Tanaka et al., "Specificity of Hybridization Between DNA Sequences Based on Free Energy," DNA Computing, 2006, pp. 371-379.

Tasset et al., "Oligonucleotide Inhibitors of Human Thrombin that Bind Distinct Epitopes," J. Mol. Biol., 1997, pp. 688-698, vol. 272, No. 5.

Telephone Consultation Records faxed May 6, 2010 regarding telephone interviews held on Apr. 27, and May 3, 2010 from related European Patent Application No. 04813618.8; 5 pgs.

Tuerk et al., "Systematic Evolution of Ligands by Exponential Enrichment: RNA Ligands to Bacteriophage T4 DNA Polymerase," Science, 1990, pp. 505-510, vol. 249, No. 4968.

Uptima FT-UP17412 SMCC sSMCC Heterobifunctional cross-linkers brochure, undated, Office Action dated Jul. 2, 2008 in related U.S. Appl. No. 10/539,107; 3 pgs.

Uptima FT-UP79042 SPDP, Ic-SPDP, Sulfo-Ic-SPDP Heterobifunctional cross-linkers brochure, undated (Sep. 15, 2009), Office action dated Sep. 30, 2009 in related U.S. Appl. No. 11/836,333; 3 pgs.

Wilson et al., "In Vitro Selection of Functional Nucleic Acids," Ann. Rev. Biochem., 1999, pp. 611-647, vol. 68.

Written Submissions dated Apr. 22, 2010 from related European Patent Application No. 04813618.8; 15 pgs.

Written Submissions dated Apr. 30, 2010 from related European Patent Application No. 04813618.8; 37 pgs.

Written Submissions dated Apr. 6, 2010 from related European Patent Application No. 04813618.8; 16 pgs.

Xu et al., "Anti-peptide aptamers recognize amino acid sequence and bind a protein epitope," Proc. Natl. Acad. Sci. USA, 1996, pp. 7475-7480, vol. 93.

Yamamoto et al., "Molecular beacon aptamer fluoresces in the presence of Tat protein of HIV-1," Genes to Cells, 2000, pp. 389-396, vol. 5.

Zalipsky, "Chemistry of polyethylene glycol conjugates with biologically active molecules," Advanced Drug Delivery Reviews, 1995, pp. 157-182, vol. 16.

Zhang et al., "A Simple Statistical Parameter for Use in Evaluation and Validation of High Throughput Screening Assays," J. Biomol. Screening, 1999, pp. 67-73, vol. 4, No. 2.

ss DNA/RNA-ss DNA/RNA
ss DNA/RNA ds DNA-protein protein-protein

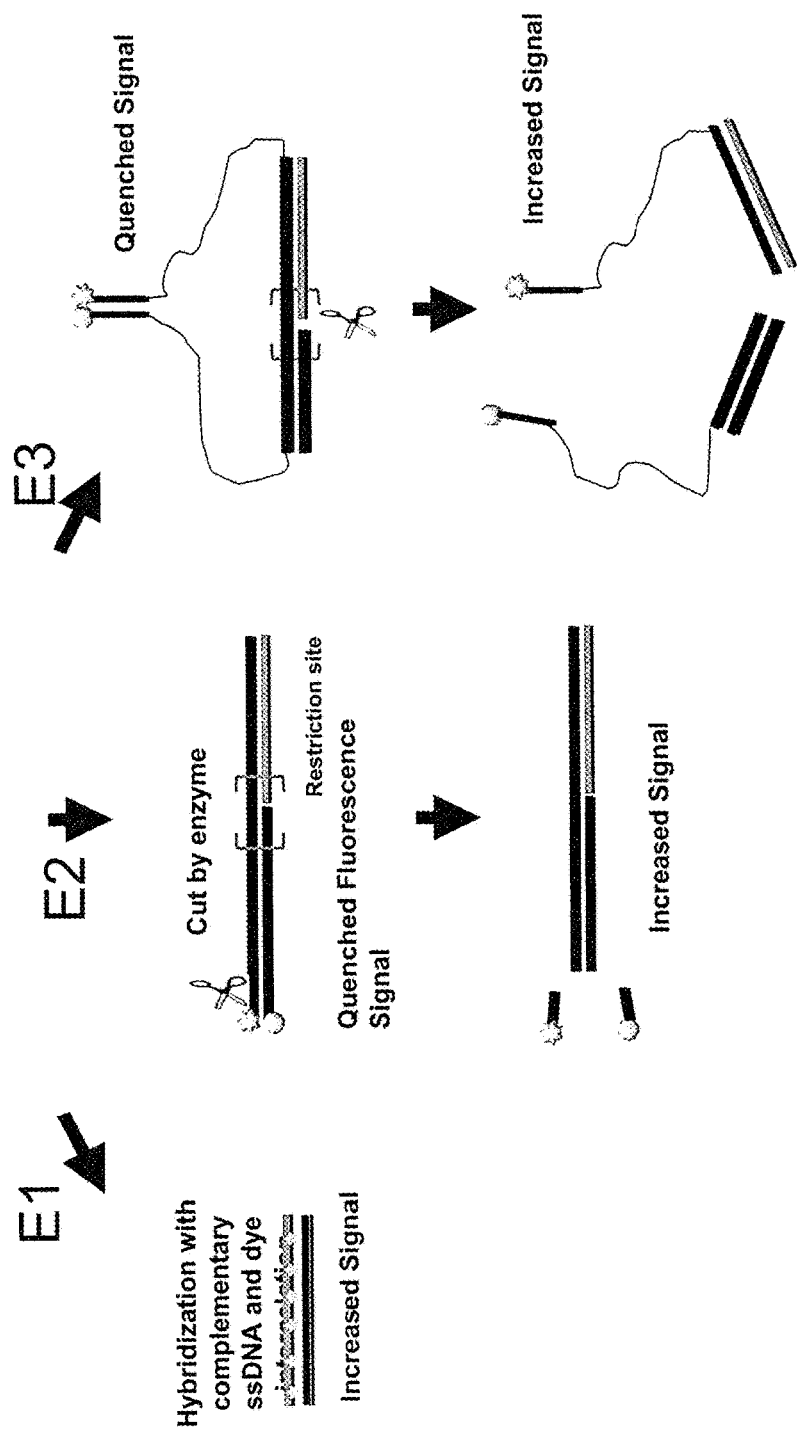

SEQUENCE LISTING

```
<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 1

Asp Tyr Lys Asp Asp Asp Lys
1               5

<210> SEQ ID NO 2
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 2

Tyr Pro Tyr Asp Val Pro Asp Tyr Ala
1               5

<210> SEQ ID NO 3
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 3

Glu Gln Lys Leu Ile Ser Glu Glu Asp Leu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 4

Gly Lys Pro Ile Pro Asn Pro Leu Leu Gly Leu Asp Ser Thr
1               5                   10
```

MOLECULAR BIOSENSORS WITH A MODULAR DESIGN

CROSS REFERENCE TO RELATED APPLICATIONS

This application claims the priority of U.S. provisional application No. 62/049,562, filed Sep. 12, 2014, which is hereby incorporated by reference in its entirety.

GOVERNMENTAL RIGHTS

This invention was made, in part, with government support under SBIR grant numbers 200-2012-52857 and HHSN261201200081C awarded by the NIH. The U.S. Government has certain rights in this invention.

FIELD OF THE INVENTION

The invention relates to two- and three-component molecular biosensors that have a modular design, and methods for detecting several types of target molecules, such as antibodies. The invention also relates to solid surfaces immobilized with one component of the biosensor.

BACKGROUND OF THE INVENTION

The detection, identification and quantification of specific molecules in our environment, food supply, water supply and biological samples (blood, cerebral spinal fluid, urine, et cetera) can be very complex, expensive and time consuming. Methods utilized for detection of these molecules include gas chromatography, mass spectroscopy, DNA sequencing, immunoassays, cell-based assays, biomolecular blots and gels, and myriad other multi-step chemical and physical assays.

There continues to be a high demand for convenient methodologies for detecting and measuring the levels of specific proteins in biological and environmental samples. Detecting and measuring levels of proteins is one of the most fundamental and most often performed methodologies in biomedical research. While antibody-based protein detection methodologies are enormously useful in research and medical diagnostics, they are not well adapted to rapid, high-throughput parallel protein detection.

Previously, the inventor had developed a fluorescent sensor methodology for detecting a specific subclass of proteins, i.e., sequence-specific DNA binding proteins (Heyduk, T.; Heyduk, E. Nature Biotechnology 2002, 20, 171-176; Heyduk, E.; Knoll, E.; Heyduk, T. Analyt. Biochem. 2003, 316, 1-10; U.S. Pat. No. 6,544,746 and copending patent application Ser. No. 10/062,064, PCT/US02/24822 and PCT/US03/02157, which are incorporated herein by reference). This methodology is based on splitting the DNA binding site of proteins into two DNA "half-sites." Each of the resulting "half-sites" contains a short complementary single-stranded region of the length designed to introduce some propensity for the two DNA "half-sites" to associate recreating the duplex containing the fully functional protein binding site. This propensity is designed to be low such that in the absence of the protein only a small fraction of DNA half-sites will associate. When the protein is present in the reaction mixture, it will bind only to the duplex containing fully functional binding site. This selective binding will drive association of DNA half-sites and this protein-dependent association can be used to generate a spectroscopic signal reporting the presence of the target protein. The term "molecular beacons" is used in the art to describe the above assay to emphasize that selective recognition and generation of the signal reporting the recognition occur in this assay simultaneously. Molecular beacons for DNA binding proteins have been developed for several proteins illustrating their general applicability (Heyduk, T.; Heyduk, E. Nature Biotechnology 2002, 20, 171-176, which is herein incorporated by reference). Their physical mechanism of action has been established and they have also been used as a platform for the assay detecting the presence of ligands binding to DNA binding proteins (Heyduk, E.; Knoll, E.; Heyduk, T. Analyt. Biochem. 2003, 316, 1-10; Knoll, E.; Heyduk, T. Analyt. Chem. 2004, 76, 1156-1164; Heyduk, E.; Fei, Y.; Heyduk, T. Combinatorial Chemistry and High-throughput Screening 2003, 6, 183-194, which are incorporated herein by reference.)

Two- and three-component molecular biosensors for targets other than DNA binding proteins have also been described (U.S. Pat. Nos. 7,939,313, 7,795,009, 7,811,809, 8,431,388, 12/961,135, 13/728,226, 3/133,198, 13/578,718, which are incorporated herein by reference). Both the two- and three-component designs typically comprise two epitope binding constructs covalently attached to a signaling oligonucleotide through a flexible linker. The two-component design is directly labeled with a detection means, while the three-component design comprises a third construct labeled with a detection means. Regardless of the design, co-association of two epitope-binding agent constructs with a target molecule results in bringing two signaling oligonucleotides into proximity such that a detectable signal is produced. While already very useful, the design of the above biosensors are not compatible with epitope binding agents that have poor solubility. Thus, there remains a need in the art.

SUMMARY OF THE INVENTION

In an aspect, the present invention encompasses a molecular biosensor comprising two construction. The two constructs together have the formula (I):

$(R^1-(X^1{}_1)_n)-X^2{}_1-R^2-R^3-R^4$; and $(R^5-(X^1{}_2)_m)-X^2{}_2-R^6-R^7-R^8$;  (I)

wherein:
$X^1{}_1$ and $X^2{}_1$ are a first affinity binding pair;
$X^1{}_2$ and $X^2{}_2$ are a second affinity binding pair;
n and m are each an integer from 1 to 2;
$R^1$ is a first epitope binding agent that binds to a first epitope on a target molecule;
$R^2$ is a flexible linker attaching $X^1{}_1$ to $R^3$;
$R^3$ and $R^7$ comprise a pair of complementary nucleotide sequences such that $R^3$ and $R^7$ only associate when $R^1$ and $R^5$ are bound to the target molecule;
$R^4$ and $R^8$ together comprise a detection means such that when $R^3$ and $R^7$ associate a detectable signal is produced;
$R^5$ is a second epitope binding agent that binds to a second epitope on the target molecule; and
$R^6$ is a flexible linker attaching $X^2{}_2$ to $R^7$.

In another aspect, the present invention encompasses a method for detecting a target molecule. The method comprises contacting a sample comprising the target molecule with a molecular biosensor. The biosensor comprises:

$(R^1-(X^1{}_1)_n)-X^2{}_1-R^2-R^3-R^4$; and $(R^5-(X^1{}_2)_m)-X^2{}_2-R^6-R^7-R^8$;

wherein:
X$^1_1$ and X$^2_1$ are a first affinity binding pair;
X$^1_2$ and X$^2_2$ are a second affinity binding pair;
n and m are each an integer from 1 to 2;
R$^1$ is a first epitope binding agent that binds to a first epitope on a target molecule;
R$^2$ is a flexible linker attaching X$^1_1$ to R$^3$;
R$^3$ and R$^7$ comprise a pair of complementary nucleotide sequences such that R$^3$ and R$^7$ only associate when R$^1$ and R$^5$ are bound to the target molecule;
R$^4$ and R$^8$ together comprise a detection means such that when R$^3$ and R$^7$ associate a detectable signal is produced;
R$^5$ is a second epitope binding agent that binds to a second epitope on the target molecule; and
R$^6$ is a flexible linker attaching X$^2_2$ to R$^7$; and
detecting the signal produced by the association of R$^3$ with R$^7$.

In still another aspect, the present invention encompasses a molecular biosensor comprising three constructs which together have the formula (III):

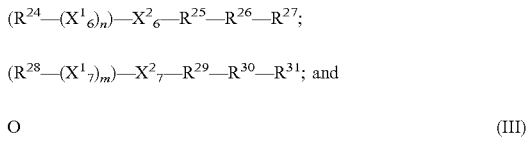

O           (III)

wherein:
X$^1_6$ and X$^2_6$ are a first affinity binding pair;
X$^1_7$ and X$^2_7$ are a second affinity binding pair;
n and m are each an integer from 1 to 2;
R$^{24}$ is an epitope-binding agent that binds to a first epitope on a target molecule;
R$^{25}$ is a flexible linker attaching X$^2_6$ to R$^{26}$;
R$^{26}$ and R$^{30}$ comprise a pair of nucleotide sequences that are not complementary to each other, but are complementary to two distinct regions on O;
R$^{27}$ and R$^{31}$ together comprise a detection means such that when R$^{26}$ and R$^{30}$ associate with O, a detectable signal is produced;
R$^{28}$ is an epitope-binding agent that binds to a second epitope on the target molecule;
R$^{29}$ is a flexible linker attaching X$^2_7$ to R$^{30}$; and
O is a nucleotide sequence comprising a first region that is complementary to R$^{26}$, and a second region that is complementary to R$^{30}$.

DESCRIPTION OF THE FIGURES

The application file contains at least one photograph executed in color. Copies of this patent application publication with color photographs will be provided by the Office upon request and payment of the necessary fee.

FIG. 13A depicts an aptamer-apatmer biosensor detecting protein. FIG. 13B depicts an dsDNA-aptamer biosensor detecting protein. FIG. 13C depicts an aptamer-antibody biosensor detecting protein. FIG. 13D depicts a dsDNA-antibody biosensor detecting protein. FIG. 13E depicts an antibody-antibody biosensor detecting protein. The antibodies may detect repeating or distinct epitopes. FIG. 13F depicts a dsDNA-dsDNA biosensor detecting protein. FIG. 13G depicts a ssDNA/RNA-ssDNA/RNA biosensor detecting ssDNA/RNA. FIG. 13H depicts a biosensor detecting dsDNA and protein interaction. FIG. 13I depicts a biosensor detecting protein-protein interaction.

(FIG. 15A) Design of the model for a competitive molecular sensor for detecting a protein. (FIG. 15B) Design of a competitive sensor for detecting an antigen.

FIG. 17A and FIG. 17B depict the overall design and function of a two-component molecular biosensor comprising a single nicking site. FIG. 17A depicts binding interactions, formation of restriction site, enzyme nicking and chain elongation. (Step A) The epitope-binding agent constructs each comprise a single-stranded nucleotide sequence. Each single-stranded sequence comprises a complementary sequence. Additionally, at least one single-stranded sequence comprises a restriction endonuclease recognition site. Association of the epitope binding agents with a target molecule results in annealing of the complementary sequences of the single-stranded nucleotide sequences. (Step B) When the complementary regions are extended in the presence of a polymerase, a double-stranded endonuclease recognition site is reconstituted. (Step C) The newly synthesized double-stranded recognition sequence may be nicked by a nicking restriction endonuclease that recognizes the reconstituted restriction enzyme recognition site. (Step D) A DNA polymerase may then extend a second nucleic acid from the nick, thereby displacing the first nicked strand to form a displaced strand. The second extended strand may then be nicked, repeating the extension and displacement steps such that multiple copies of the displaced strand are produced, thereby amplifying the signal from the biosensor. FIG. 17B depicts several different methods that may be used to detect the displaced strand. (Step E1) A displaced strand may be detected and/or quantitated by contacting a displaced strand with a complementary nucleic acid sequence. The resulting double-stranded nucleotide sequence may be detected using nucleic acid staining methods specific for double-stranded sequences. (Step E2) A displaced strand may be detected and/or quantitated by associating with a Type IIS endonuclease nucleic acid construct. (Step E3) A displaced strand may be detected by a linker construct.

DETAILED DESCRIPTION OF THE INVENTION

Figure 1:
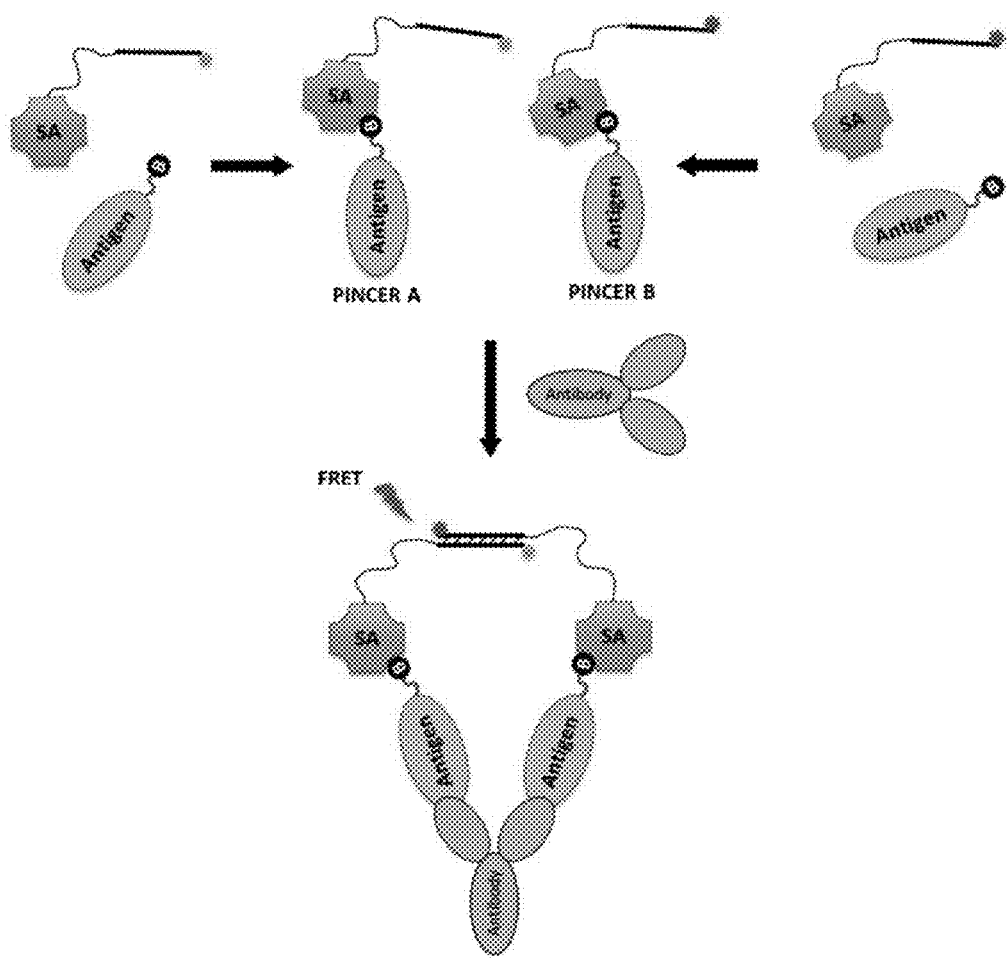
FIG. 1 is an illustration of a generic two-component biosensor assay for antibody detection. In this illustration, the affinity binding pair is biotin and streptavidin, the first and second epitope binding agents are antigens, and the target molecule is an antibody. Contacting a first signaling oligonucleotide attached to streptavidin through a flexible linker with a first epitope binding agent modified with biotin results in the non-covalent binding of biotin to streptavidin and the tight association of the epitope binding agent to the signaling oligonucleotide to produce the first epitope binding agent construct (labeled Pincer A in the illustration). The second epitope binding agent construct is similarly produced (labeled Pincer B in the illustration). Co-association of the two epitope-binding agent constructs with the target molecule results in bringing the two signaling oligonucleotides into proximity such that a detectable signal is produced.

The present invention is directed to molecular biosensors comprising epitope-binding agent constructs with a modular design. The epitope-binding agent constructs each comprise a signaling oligonucleotide that is non-covalently bound to an epitope binding agent through the interaction of an affinity binding pair, wherein a flexible linker attaches the signaling oligonucleotide to one member of the affinity binding pair. Advantageously, when an affinity binding pair has a small dissociation constant, the design allows for use of poorly soluble epitope binding agents that are intractable in traditional designs of molecular biosensors. The modular design also provides cost- and time-saving benefits, by offering a universal approach for developing multiple epitope-binding agent constructs comprised of the same signaling oligonucleotide with different epitope binding agents.

The molecular biosensors may be utilized in several different methods, such as the detection of a target molecule. In one design, the biosensor is comprised of two components, which comprise two epitope-binding agent constructs. In the two-component design, detection of a target molecule typically involves target-molecule induced co-association of two epitope-binding agent constructs that each recognize separate epitopes on the target molecule. The epitope-binding agent constructs each comprise complementary signaling oligonucleotides that are labeled with detection means and are attached to an epitope binding agent through the interaction of an affinity binding pair, wherein a flexible linker attaches the signaling oligonucleotide to one member of the affinity binding pair. Co-association of the two epitope-binding agent constructs with the target molecule results in bringing the two signaling oligonucleotides into proximity such that a detectable signal is produced.

Alternatively, in another design the biosensor is comprised of three components, which comprise two epitope-binding agent constructs and an oligonucleotide construct. In the three-component design, analogous to the two-component design, detection of a target molecule typically involves target-molecule induced co-association of two epitope-binding agent constructs that each recognize separate epitopes on the target molecule. Unlike the two-component design, however, the epitope-binding agent constructs each comprise non-complementary signaling oligonucleotides that are labeled with detection means and are attached to the epitope-binding agents through the interaction of an affinity binding pair, wherein a flexible linker attaches the signaling oligonucleotide to one member of the affinity binding pair. Each signaling oligonucleotide is complementary to one of two distinct regions on the oligonucleotide construct. Co-association of the two epitope-binding agent constructs with the target molecule results in hybridization of each signaling oligonucleotide to the oligonucleotide construct. Binding of the two signaling oligonucleotides to the oligonucleotide construct brings them into proximity such that a detectable signal is produced.

The molecular biosensors, irrespective of the design, provide a rapid homogeneous means to detect a variety of target molecules, including but not limited to proteins, carbohydrates, macromolecules, and analytes. In an exemplary embodiment, a biosensor may be used to detect an antigen. In another exemplary embodiment, a biosensor may be used to detect a target antibody. For instance, a target antibody may be a disease or disorder specific antibody. Nonlimiting examples of target antibodies may be anticancer antibodies, antimicrobial antibodies, antiviral antibodies or autoimmune antibodies. In some embodiments target antibodies may be IgG, IgM, IgA, or IgE. In particular, the three-component biosensors are useful in several applications involving solid surfaces.

I Epitope-Binding Agent Constructs with a Modular Design

One aspect of the invention, accordingly, encompasses an epitope-binding agent construct with a modular design. Generally speaking, an epitope-binding agent construct of the invention comprises a signaling oligonucleotide that is non-covalently bound to an epitope binding agent through the interaction of an affinity binding pair, wherein a flexible linker attaches the signaling oligonucleotide to one member of the affinity binding pair. In certain embodiments, an epitope-binding agent construct further comprises a detectable means. The signaling oligonucleotide, flexible linker, epitope binding agent and detectable means are described in detail in Sections II-IV.

As used herein, the phrase "affinity binding pair" refers to a ligand and its cognate binding partner. In some embodiments, a binding partner is capable of binding only one ligand. In other embodiments, a binding partner is capable of binding more than one of the ligand. Binding partners capable of binding more than one of the ligand can be described as multivalent. In an embodiment, a multivalent binding partner may be capable of binding 2, 3 or 4 or more ligands. In a specific embodiment, a multivalent binding partner binds 1 ligand. The multivalent binding partner may be positioned on the epitope binding agent or the signaling oligonucleotide provided it does not interfere with binding of the epitope binding agent to the target molecule. In an embodiment, an epitope binding agent comprises the ligand and the signaling oligonucleotide comprises the cognate binding partner via a flexible linker. Alternatively, an epitope binding agent comprises the cognate binding partner and the signaling oligonucleotide comprises the ligand via a flexible linker. Generally speaking, the member of the affinity binding pair that is smaller in size is attached to the epitope binding agent in order to minimize steric interference of the epitope binding agent-target molecule interaction. In another embodiment, both a signaling oligonucleotide may comprise a ligand via a linker and an epitope binding agent may comprise a ligand. In such an embodiment, both ligands are bound to the same multivalent cognate binding pair thereby linking the epitope binding agent and signaling oligonucleotide.

The affinity between the ligand and its cognate binding partner can be described in terms of a dissociation constant ($K_d$). In some embodiments, affinity binding pairs of the invention may have at least a micromolar dissociation constant. For example, the ligand and its cognate binding partner may bind with a dissociation constant of at least about $10^{-6}$ M. Stated another way, the binding partners may bind with a dissociation constant of about $1\times10^{-6}$ M, about $2\times10^{-6}$ M, about $3\times10^{-6}$ M, about $4\times10^{-6}$ M, about $5\times10^{-6}$ M, about $6\times10^{-6}$ M, about $7\times10^{-6}$ M, about $8\times10^{-6}$ M, about $9\times10^{-6}$ M, about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-8}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, about $9\times10^{-9}$ M, about $1\times10^{-10}$ M, about $2\times10^{-10}$ M, about $3\times10^{-10}$ M, about $4\times10^{-10}$ M, about $5\times10^{-10}$ M, about $6\times10^{-10}$ M, about $7\times10^{-10}$ M, about $8\times10^{-10}$ M, about $9\times10^{-10}$ M, $1\times10^{-11}$ M, about $2\times10^{-11}$ M, about $3\times10^{-11}$ M, about $4\times10^{-11}$ M, about $5\times10^{-11}$ M, about $6\times10^{-11}$ M, about $7\times10^{-11}$ M, about $8\times10^{-11}$ M, about $9\times10^{-11}$ M, about $1\times10^{-12}$ M, about $2\times10^{-12}$ M, about $3\times10^{-12}$ M, about $4\times10^{-12}$ M, about $5\times10^{-12}$ M, about $6\times10^{-12}$ M, about $7\times10^{-12}$ M, about $8\times10^{-12}$ M, about $9\times10^{-12}$ M, about $1\times10^{-13}$ M, about $2\times10^{-13}$ M, about $3\times10^{-13}$ M, about $4\times10^{-13}$ M, about $5\times10^{-13}$ M, about $6\times10^{-13}$ M, about $7\times10^{-13}$ M, about $8\times10^{-13}$ M, about $9\times10^{-13}$ M, about $1\times10^{-14}$ M, about $2\times10^{-14}$ M, about $3\times10^{-14}$ M, about $4\times10^{-14}$ M, about $5\times10^{-14}$ M, about $6\times10^{-14}$ M, about $7\times10^{-14}$ M, about $8\times10^{-14}$ M, about $9\times10^{-14}$ M, about $1\times10^{-15}$ M, about $2\times10^{-15}$ M, about $3\times10^{-15}$ M, about $4\times10^{-15}$ M, about $5\times10^{-15}$ M, about $6\times10^{-15}$ M, about $7\times10^{-15}$ M, about $8\times10^{-15}$ M, or about $9\times10^{-15}$ M. In other embodiments, affinity binding pairs of the invention may have at least a nanomolar dissociation constant. For example, the ligand and its cognate binding partner may bind with a dissociation constant of at least about $10^{-9}$ M. In still other embodiments, affinity binding pairs of the invention have at least a picomolar dissociation constant. For example, the ligand and its cognate binding partner may bind with a dissociation constant of at least about $10^{-12}$ M. In yet other embodiments, affinity binding pairs of the invention have at least a femtomolar dissociation constant. For example, the ligand and its cognate binding partner may bind with a dissociation constant of at least about $10^{-15}$ M.

In a preferred embodiment, an affinity binding pair of the invention remains bound in the presence of a protein or a nucleic acid denaturant. Protein or nucleic acid denaturants are well known in the art. Non-limiting examples include high temperature, high pH, organic solvents, urea, guanidinium chloride, sodium dodecyl sulfate (SDS), Triton, and other detergents. In some embodiments, an affinity binding pair of the invention remains bound in the presence of about 0.1 M to about 1 M urea. In other embodiments, an affinity binding pair of the invention remains bound in the presence of about 0.1 M to about 0.5 M urea. In still other embodiments, an affinity binding pair of the invention remains bound in the presence of about 0.4 M to about 0.5 M urea. As described in Example 1, attempts to create an epitope-binding agent construct comprising a poorly soluble epitope binding agent by standard methods were not successful, as the epitope binding agent precipitated when the necessary modifications were made. In contrast, the instantly claimed design allows incorporation of the poorly soluble epitope binding agent in the presence of a denaturant, which keeps the epitope binding agent soluble. Non-limiting examples of suitable affinity binding pairs include biotin/biotin binding protein and anti-tag antibody/tag protein. Non-limiting examples of suitable anti-tag antibody/tag protein pairs include anti-DDK antibody/DYKDDDK (SEQ ID NO:1) epitope (FLAG), anti-GFP antibody/GFP, anti-GST antibody/GST tag, anti-HA antibody/HA tag (YPYDVPDYA (SEQ ID NO:2) epitope), anti-His antibody/His tag (6×-His), anti-Myc antibody/Myc tag (EQKLISEEDL (SEQ ID NO:3) epitope), anti-V5 antibody/V5 tag (GKPIPNPLL-GLDST (SEQ ID NO:4) epitope), anti-mCherry antibody/mCherry, anti-tdTomato antibody/tdTomato, and other anti-fluorescent protein antibodies and their respective fluorescent protein. In an exemplary embodiment, an affinity binding pair of the invention comprises biotin and a biotin binding protein. Non-limiting examples of biotin binding proteins include avidin, deglycosylated avidin, native streptavidin, and recombinant streptavidin. The phrase "recombinant streptavidin" includes monovalent, divalent, trivalent, or tetravalent streptavidin, as well as truncated variants that comprise the 3-barrel structure characteristic of streptavidin. Truncated streptavidins are known in the art; see for example Sano et al. *J. Biol. Chem* 270: 28201 to 28209, 1995, hereby incorporated by reference in its entirety.

A skilled artisan will be familiar with the numerous different biotinylation reagents and procedures that are well known in the art, in some cases commercially available, and suitable for the invention. Biotin may be incorporated into or attached to a wide diversity of compounds, including, but not limited to proteins, peptides, nucleotides, carbohydrates, and polysaccharides. For example, proteins and peptides may be biotinylated on a free amine, sulfhydryl and/or carboxy group using an appropriate biotin derivative (e.g. N-hydroxysuccinimide ester (NHS-ester) of biotin, 3-(N-maleimidopropionyl) biocytin or iodoacetyl-LC biotin, or biocytin hydrazide, respectively). Carbohydrates or glycoproteins are easily biotinylated by using biotin-LC-hydrazide or biocytin hydrazide, after the vicinal hydroxyl group of the sugar has been oxidized to an aldehyde. Nucleic acid biotinylation can be accomplished with several different procedures, including introduction of biotinylated nucleotides using nick translation or random priming, or chemical labeling of aliphatic primary amines on nucleotide or modified nucleotide bases. For a review see Diamandis et al *Clin Chem* 37(5): 625-636, 1991. Biotin binding proteins may be recombinantly produced, purified from naturally producing organisms, or commercially acquired. Like biotin and its derivatives, biotin binding proteins may be modified with peptides, nucleic acids and carbohydrates following standard chemical procedures known to one skilled in the art. Further details can be also found in the Examples.

In certain embodiments, the performance of molecular biosensors of the invention is affected by the degree of biotinylation. Generally speaking, Applicants have found assay performance can be inversely correlated to biotinylation of the epitope binding agent. A functional biosensor can be produced using a ratio of biotin:epitope binding agent of about 10:1, but more preferably the ratio is about 3:1, about 2:1 or about 1:1. In a specific embodiment, a ratio of biotin:epitope binding agent may be about 1:1. The degree of biotinylation can be experimentally determined using methods known in the art, or as detailed in the Examples.

An epitope-binding agent construct of the invention may be produced by (1) modifying an epitope binding agent with a ligand, (2) attaching a signaling oligonucleotide to the cognate binding partner through a flexible linker, and (3) contacting the components of (1) and (2) under effective conditions for a period of time sufficient to allow formation of a complex between the ligand and the affinity binding partner. In embodiments where the epitope-binding agent construct further comprises a detectable means, the signaling oligonucleotide attached to the cognate binding partner through the flexible linker may be conjugated directly or indirectly to the detectable means before or after contacting the signaling oligonucleotide to the modified epitope binding agent. Alternatively, an epitope-binding agent construct of the invention may be produced by (1) modifying an epitope binding agent with a ligand, (2) attaching the cognate binding partner to the flexible linker via a covalent linkage and attaching the signaling oligonucleotide to the flexible linker via annealing of complementary nucleotide sequences, and (3) contacting the components of (1) and (2) under effective conditions for a period of time sufficient to allow formation of a complex between the ligand and the affinity binding partner. Alternatively, an epitope-binding agent construct of the invention may be produced by (1) modifying an epitope binding agent with a ligand, (2) providing a signaling oligonucleotide attached to the cognate binding partner through a flexible linker, and (3) contacting the components of (1) and (2) under effective conditions for a period of time sufficient to allow formation of a complex between the ligand and the affinity binding partner. In a different aspect, an epitope-binding agent construct of the invention may be produced by (1) modifying a signaling oligonucleotide with a ligand through a flexible linker, (2) attaching an epitope binding agent to the cognate binding partner, and (3) contacting the components of (1) and (2) under effective conditions for a period of time sufficient to allow formation of a complex between the ligand and the affinity binding partner. In yet another aspect, an epitope-binding agent construct of the invention may be produced by (1) providing a signaling oligonucleotide bound to a ligand through a flexible linker, (2) attaching an epitope binding agent to the cognate binding partner, and (3) contacting the components of (1) and (2) under effective conditions for a period of time sufficient to allow formation of a complex between the ligand and the affinity binding partner. Variables such as time, temperature and the ratio of the two components can be experimentally determined, as detailed in the Examples. Epitope-binding agent constructs with a modular design may be used in a molecular biosensor as described below.

II Two-Component Molecular Biosensors

Another aspect of the invention encompasses a two-component molecular biosensor. Several molecular configurations of biosensors are suitable for use in the invention as illustrated by way of non-limiting example in FIGS. 13, 14, and 15. In one embodiment, the molecular biosensor will be monovalent comprising a single epitope-binding agent that binds to an epitope on a target molecule. The molecular biosensor of the invention, however, is typically multivalent. It will be appreciated by a skilled artisan, depending upon the target molecule, that the molecular biosensor may comprise from about 2 to about 5 epitope binding agents. Typically, the molecular biosensor will comprise 2 or 3 epitope binding agents and more typically, will comprise 2 epitope binding agents. In one alternative of this embodiment, therefore, the molecular biosensor will be bivalent comprising a first epitope binding agent that binds to a first epitope on a target molecule and a second epitope binding agent that binds to a second epitope on the target molecule. In yet another alternative of this embodiment, the molecular biosensor will be trivalent comprising a first epitope binding agent that binds to a first epitope on a target molecule, a second epitope binding agent that binds to a second epitope on a target molecule and a third epitope binding agent that binds to a third epitope on a target molecule. In each of the above embodiments, the first and second epitope may be a repeating epitope on a target molecule or may be distinct epitopes on a target molecule.

(a) Bivalent Molecular Sensors

In one alternative of the invention, a molecular biosensor will be bivalent. In a typical embodiment, a bivalent molecular sensor will comprise a first epitope binding agent that binds to a first epitope on a target molecule, a first affinity binding pair, a first linker, a first signaling oligo, a first detection means, a second epitope binding agent that binds to a second epitope on the target molecule, a second affinity binding pair, a second linker, a second signaling oligo, and a second detection means.

In one preferred embodiment, the molecular biosensor comprises two epitope-binding agent constructs, which together have formula (I):

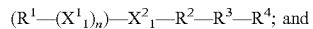

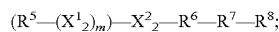

wherein:
- $X^1_1$ and $X^2_1$ are a first affinity binding pair;
- $X^1_2$ and $X^2_2$ are a second affinity binding pair;
- n and m are each an integer from 1 to 2;
- $R^1$ is a first epitope binding agent that binds to a first epitope on a target molecule;
- $R^2$ is a flexible linker attaching $X^2_1$ to $R^3$;
- $R^3$ and $R^7$ comprise a pair of complementary nucleotide sequences having a free energy for association from about −5.5 kcal/mole to about −8.0 kcal/mole at a temperature from about 21° C. to about 40° C. and at a salt concentration from about 1 mM to about 100 mM;
- $R^4$ and $R^8$ together comprise a detection means such that when $R^3$ and $R^7$ associate a detectable signal is produced;
- $R^5$ is a second epitope binding agent that binds to a second epitope on the target molecule; and
- $R^6$ is a flexible linker attaching $X^2_2$ to $R^7$.

As will be appreciated by those of skill in the art, the choice of epitope binding agents, $R^1$ and $R^5$, in molecular biosensors comprising two epitope-binding agent constructs having formula (I) can and will vary depending upon the particular target molecule. By way of example, when the target molecule is a protein, peptide or antigen, $R^1$ and $R^5$ may be an aptamer, or antibody. By way of further example, when the target molecule is an antibody, $R^1$ and $R^5$ may be an antigen or peptide specifically recognized by the variable region of a target antibody. By way of another example, when $R^1$ and $R^5$ are double stranded nucleic acid the target molecule is typically a macromolecule that binds to DNA or a DNA binding protein. In an aspect, $R^1$ and $R^5$ may be two epitope binding agents that each specifically recognize distinct epitopes on the same target molecule. In another aspect, $R^1$ and $R^5$ may be two epitope binding agents that each specifically recognize distinct epitopes on different target molecules. In still another aspect, $R^1$ and $R^5$ may be two epitope binding agents that each specifically recognize a repeating epitope on the same target molecule. It is contemplated herein that $R^1$ and $R^5$ may or may not be the same epitope binding agent. For example, $R^1$ and $R^5$ may be independently selected from a group of suitable epitope binding agents. Non-limiting examples of suitable epitope binding agents, depending upon the target molecule, include agents selected from the group consisting of an aptamer, an antibody, an antibody fragment, a double-stranded DNA sequence, an antigen, modified nucleic acids, nucleic acid mimics, a ligand, a ligand fragment, a receptor, a receptor fragment, a protein, a polypeptide, a peptide, a coenzyme, a coregulator, an allosteric molecule, and an ion.

In some embodiments, $R^1$ and $R^5$ are each aptamers having a sequence ranging in length from about 20 to about 110 bases. In other embodiments, $R^1$ and $R^5$ are each an antibody independently selected from the group consisting of a polyclonal antibody, an ascite, a Fab fragment, a Fab' fragment, a monoclonal antibody, and a humanized antibody. In still other embodiments, $R^1$ and $R^5$ are each a peptide or antigen. For example, $R^1$ and $R^5$ may be peptides or antigens specifically recognized by the variable region of an antibody. By way of non-limiting example, $R^1$ and $R^5$ may be peptides or antigens specifically recognized by the variable region of a disease or disorder specific antibody. In yet other embodiments, $R^1$ and $R^5$ are each double stranded DNA. In different embodiments, $R^1$ is a double stranded nucleic acid and $R^5$ is an aptamer. In still different embodiments, $R^1$ is an aptamer and $R^5$ is a double stranded nucleic acid. In alternative embodiments, $R^1$ is an antibody and $R^5$ is an aptamer. In other alternative embodiments, $R^1$ is an aptamer and $R^5$ is an antibody. In additional embodiments, $R^1$ is an antibody and $R^5$ is a double stranded DNA. In still additional embodiments, $R^1$ is a double stranded DNA and $R^5$ is an antibody. In further embodiments, $R^1$ is an antibody and $R^5$ is a peptide. In still further embodiments, $R^1$ is a peptide and $R^5$ is an antibody. In a preferred embodiment, $R^1$ and $R^5$ are each a monoclonal antibody. In another preferred embodiment, $R^1$ and $R^5$ are each a peptide or antigen.

In another aspect of a molecular biosensor comprising two epitope-binding agent constructs having formula (I), an affinity binding pair ($X^1_1/X^2_1$; $X^1_2/X^2_2$) non-covalently binds each epitope binding agent, $R^1$ and $R^5$, to a signaling oligonucleotide, $R^3$ and $R^7$, respectively, through a flexible linker, $R^2$ and $R^6$, respectively. In some embodiments, the affinity bind pair in each epitope-binding construct is the same. For example, the first and second affinity binding pair may each consist of biotin and a biotin binding partner. In other embodiments, the affinity binding pair in each epitope-binding construct is different. For example, the first affinity binding pair may consist of biotin and a biotin binding partner, and the second affinity binding pair may consist of an anti-tag antibody and tag protein. Suitable affinity binding pairs are described above in Section I. Generally speaking, the member of the affinity binding pair that is smaller in size is attached to the epitope binding agent in order to minimize steric interference of the epitope binding agent—target molecule interaction. By way of non-limiting example, biotin is preferably attached to the epitope binding agent when the affinity binding pair consists of biotin and a biotin binding partner.

Figure 21:
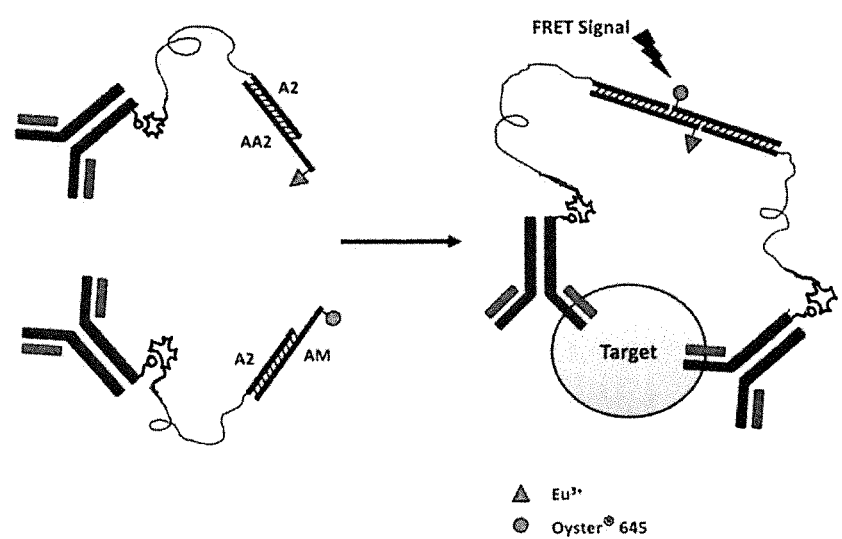
FIG. 21 depicts an embodiment in which the linker comprises a region complementary to the signaling oligonucleotide. A portion of the linker (A2) may be complementary to a portion of the signaling oligo (AA2 or AM). When a linker comprising nucleotides complementary to a portion of a signaling oligo (A2) is contacted with a signaling oligo comprising nucleotides complementary to a linker (AA2 or AM), the linker anneals with the portion of the signaling oligo that is complementary to the linker but do not anneal to the sequences of the signaling oligo that are complementary to the other signaling oligo.

In another aspect of a molecular biosensor comprising two epitope-binding agent constructs having formula (I), linkers, $R^2$ and $R^6$, may functionally keep $R^3$ and $R^7$ in close proximity such that when $R^1$ and $R^5$ each bind to the target molecule, $R^3$ and $R^7$ associate in a manner such that a detectable signal is produced by the detection means, $R^4$ and $R^8$. $R^2$ and $R^6$ may each be a nucleotide sequence from about 10 to about 100 nucleotides in length. In one embodiment, $R^2$ and $R^6$ are from 10 to about 25 nucleotides in length. In another embodiment, $R^2$ and $R^6$ are from about 25 to about 50 nucleotides in length. In a further embodiment, $R^2$ and $R^6$ are from about 50 to about 75 nucleotides in length. In yet another embodiment, $R^2$ and $R^6$ are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment $R^2$ and $R^6$ are comprised of DNA bases. In another embodiment, $R^2$ and $R^6$ are comprised of RNA bases. In yet another embodiment, $R^2$ and $R^6$ are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^2$ and $R^6$ may be nucleotide mimics. Examples of nucleotide mimics include locked nucleic acids (LNA), peptide nucleic acids (PNA), and phosphorodiamidate morpholino oligomers (PMO). A nucleotide linker may be single-stranded, double-stranded, or a combination thereof. Alternatively, $R^2$ and $R^6$ may be a bifunctional chemical linker or a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP(N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Non-limiting examples of additional suitable linkers include polyethylene glycol such as PEG 4, PEG 8, PEG 12 (a 12-unit polyethylene glycol spacer) and the phosphoramidate form of Spacer 18 comprised of polyethylene glycol, as well as those illustrated in the Examples. In one embodiment, $R^2$ and $R^6$ are comprised of nucleotides and a bifunctional chemical linker. In another embodiment, $R^2$ and $R^6$ are comprised of a heterobifunctional chemical linker and nucleotides. In still another embodiment, $R^2$ and $R^6$ are comprised of a heterobifunctional chemical linker, a polyethylene glycol linker, and nucleotides. In a specific embodiment, $R^2$ and $R^6$ are comprised of a SMCC linker and nucleotides. In another specific embodiment, $R^2$ and $R^6$ are comprised of a SMCC linker, a polyethylene glycol linker and nucleotides. The nucleotides of $R^2$ and $R^6$ may be complementary to a portion of the signaling oligos ($R^3$ and $R^7$, respectively), wherein the nucleotides of $R^2$ and $R^6$ are not complementary to the sequences of $R^3$ and $R^7$ that are complementary to each other (described below). All or some of the nucleotides of $R^2$ and $R^6$ may be complementary to a portion of $R^3$ and $R^7$, respectively, wherein the nucleotides of $R^2$ and $R^6$ are not complementary to the sequences of $R^3$ and $R^7$ that are complementary to each other. In an embodiment where all or some of the nucleotides of $R^2$ and $R^6$ are complementary to a portion of $R^3$ and $R^7$, respectively, when $R^2$ and $R^6$ comprising nucleotides complementary to a portion of $R^3$ and $R^7$ are contacted with $R^3$ and $R^7$ comprising nucleotides complementary to $R^2$ and $R^6$, respectively, $R^2$ and $R^6$ anneal with the portion of $R^3$ and $R^7$ that is complementary to $R^2$ and $R^6$ but do not anneal to the sequences of $R^3$ and $R^7$ that are complementary to each other. See, for instance FIG. 21. In one embodiment, $R^2$ and $R^6$ are from about 1 to about 500 angstroms in length. In another embodiment, $R^2$ and $R^6$ are from about 20 to about 400 angstroms in length. In yet another embodiment, $R^2$ and $R^6$ are from about 50 to about 250 angstroms in length.

In another aspect of molecular biosensors comprising two epitope-binding agent constructs having formula (I), $R^3$ and $R^7$ comprise complementary nucleotide sequences having a length such that the complementary nucleotide sequences preferably do not associate unless $R^1$ and $R^5$ bind to separate epitopes on the target molecule. When $R^1$ and $R^5$ bind to separate epitopes of the target molecule, the complementary nucleotide sequences of $R^3$ and $R^7$ are brought to relative proximity resulting in an increase in their local concentration, which drives the association of the complementary nucleotide sequences of $R^3$ and $R^7$. In some embodiments, the complementary nucleotide sequences of $R^3$ and $R^7$ are from about 2 to about 20 nucleotides in length. In other embodiments, the complementary nucleotide sequences of $R^3$ and $R^7$ are from about 4 to about 15 nucleotides in length. In still other embodiments, the complementary nucleotide sequences of $R^3$ and $R^7$ are from about 5 to about 7 nucleotides in length. Typically, the complementary nucleotide sequences of $R^3$ and $R^7$ have a free energy for association from about −5.5 kcal/mole to about −8.0 kcal/mole as measured in the selection buffer conditions, defined below. In certain embodiments, the complementary nucleotide sequences of $R^3$ and $R^7$ have a free energy for association from about −6.0 kcal/mole to about −8.0 kcal/mole as measured in the selection buffer conditions defined below. In certain other embodiments, the complementary nucleotide sequences of $R^3$ and $R^7$ have a free energy for association from about −7.0 kcal/mole to −8.0 kcal/mole in the selection buffer conditions. In a preferred embodiment, the complementary nucleotide sequences of $R^3$ and $R^7$ have a free energy for association of about −7.5 kcal/mole in the selection buffer conditions described below. Preferably, in each embodiment the complementary nucleotide sequences of $R^3$ and $R^7$ are not complementary to $R^1$ and $R^5$ and are also not complementary to $R^2$ and $R^6$. In one embodiment, one or both of $R^3$ and $R^7$ further comprise a nucleotide sequence complementary to a nucleotide sequence of $R^2$ and $R^6$, respectively. In such an embodiment, the free energy for association described above for the complementary nucleotide sequences of $R^3$ and $R^7$ does not include the nucleotide sequences that are complementary to $R^2$ and $R^6$. The free energy for association solely includes the complementary nucleotide sequence of $R^3$ and $R^7$. In some embodiments, the nucleotide sequences of $R^3$ and $R^7$ that are complementary to the nucleotide sequences of $R^2$ and $R^6$, respectively, are from about 2 to about 40 nucleotides in length. In other embodiments, the nucleotide sequences of $R^3$ and $R^7$ that are complementary to the nucleotide sequences of $R^2$ and $R^6$, respectively, are from about 10 to about 30 nucleotides in length. In still other embodiments, the nucleotide sequences of $R^3$ and $R^7$ that are complementary to the nucleotide sequences of $R^2$ and $R^6$, respectively, are from about 15 to about 25 nucleotides in length. In still other embodiments, the nucleotide sequences of $R^3$ and $R^7$ that are complementary to the nucleotide sequences of $R^2$ and $R^6$, respectively, are from about 16 to about 20 nucleotides in length. In another aspect, one or both of $R^3$ and $R^7$ may further comprise a nucleotide sequence that is not complementary to a nucleotide sequence of $R^2$ and $R^6$, respectively, and is also not complementary to a nucleotide sequence of $R^7$ and $R^3$, respectively. In some embodiments, the nucleotide sequences of $R^3$ and $R^7$ that are not complementary to a nucleotide sequence of $R^2$ and $R^6$, respectively, and are also not complementary to a nucleotide sequence of $R^7$ and $R^3$, respectively, are from about 1 to about 10 nucleotides in length. In other embodiments, the nucleotide sequences of $R^3$ and $R^7$ that are not complementary to a nucleotide sequence of $R^2$ and $R^6$, respectively, and are also not complementary to a nucleotide sequence of $R^7$ and $R^3$, respectively, are from about 1 to about 5 nucleotides in length. In still other embodiments, the nucleotide sequences of $R^3$ and $R^7$ that are not complementary to a nucleotide sequence of $R^2$ and $R^6$, respectively, and are also not complementary to a nucleotide sequence of $R^7$ and $R^3$, respectively, are from about 1 to about 3 nucleotides in length.

In another aspect of molecular biosensors comprising two epitope-binding agent constructs having formula (I), $R^4$ and $R^8$ may together comprise several suitable detection means such that when $R^3$ and $R^7$ associate, a detectable signal is produced. Exemplary detections means suitable for use in the molecular biosensors include fluorescent resonance energy transfer (FRET), time resolved-FRET, fluorescence life-time imaging, lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, residence time changes, and redox potential changes.

Preferably, the ratio of epitope binding agent comprising ligand:cognate binding pair:linker:detectable label is 1:1:1:1, wherein the ratio of epitope binding agent:ligand ratio is 1:1 or 1:2. Stated another way, the ratio of $(R^1-(X^1{}_1)_n)$:$X^2{}_1$:$R^2$:$R^3$—$R^4$ is 1:1:1:1 or the ratio of $(R^5-(X^1{}_2)_m)$:$X^2{}_2$:$R^6$:$R^7$—$R^8$ is 1:1:1:1. However, non-limiting examples of other suitable ratios may include 1:1:1.4:1, 1.6:1:1.4:1, and 1.2:1.3:1.8:1.

In a further embodiment, a molecular biosensor comprising two epitope-binding agent constructs will have formula (I)
wherein:
$X^1{}_1$ and $X^2{}_1$ are a first affinity binding pair;
$X^1{}_2$ and $X^2{}_2$ are a second affinity binding pair;
n and m are each an integer from 1 to 2;
$R^1$ is an epitope-binding agent that binds to a first epitope on a target molecule and is selected from the group consisting of an aptamer, an antibody, an antigen, a peptide, and a double stranded nucleic acid;
$R^2$ is a flexible linker attaching $X^2{}_1$ to $R^3$ by formation of a covalent bond with $X^2{}_1$ and by annealing to a complementary sequence of $R^3$, wherein the complementary sequence does not comprise the sequence of $R^3$ complementary to $R^7$ and wherein $R^2$ comprises a bifunctional chemical cross linker and is from 0 to 500 angstroms in length;
$R^3$ and $R^7$ comprise a pair of complementary nucleotide sequences from about 4 to about 15 nucleotides in length and having a free energy for association from about −5.5 kcal/mole to about −8.0 kcal/mole at a temperature from about 21° C. to about 40° C. and at a salt concentration from about 1 mM to about 100 mM;
$R^4$ and $R^8$ together comprise a detection means selected from the group consisting of fluorescent resonance energy transfer (FRET), time resolved-FRET, fluorescence life-time imaging, lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, residence time changes, and redox potential changes such that when $R^3$ and $R^7$ associate a detectable signal is produced;
$R^5$ is an epitope binding agent that binds to a second epitope on the target molecule and is selected from the group consisting of an aptamer, an antibody, an antigen, a peptide, and a double stranded nucleic acid; and
$R^6$ is a flexible linker attaching $X^2{}_1$ to $R^7$ by formation of a covalent bond with $X^2{}_2$ and by annealing to a complementary sequence of $R^7$, wherein the complementary sequence of $R^7$ does not comprise the sequence complementary to $R^3$ and wherein $R^6$ comprises a bifunctional chemical cross linker and is from 1 to 500 angstroms in length.

Yet another embodiment of the invention encompasses a molecular biosensor comprising two epitope-binding agent constructs having formula (I)
wherein:
$X^1{}_1$ and $X^2{}_1$ are a first affinity binding pair;
$X^1{}_2$ and $X^2{}_2$ are a second affinity binding pair;
n and m are each an integer from 1 to 2;
$R^1$ is an aptamer that binds to a first epitope on a target molecule;
$R^2$ is a flexible linker attaching $X^2{}_1$ to $R^3$;
$R^3$ and $R^7$ comprise a pair of complementary nucleotide sequences having a free energy for association from about −5.5 kcal/mole to about −8.0 kcal/mole at a temperature from about 21° C. to about 40° C. and at a salt concentration from about 1 mM to about 100 mM;
$R^4$ and $R^8$ together comprise a detection means such that when $R^3$ and $R^7$ associate a detectable signal is produced;
$R^5$ is an aptamer that binds to a second epitope on the target molecule; and
$R^6$ is a flexible linker attaching $X^2{}_2$ to $R^7$.

A further embodiment of the invention encompasses a molecular biosensor comprising two epitope-binding agent constructs having formula (I)
wherein:
$X^1{}_1$ and $X^2{}_1$ are a first affinity binding pair;
$X^1{}_2$ and $X^2{}_2$ are a second affinity binding pair;
n and m are each an integer from 1 to 2;
$R^1$ is an aptamer that binds to a first epitope on a target molecule;
$R^2$ is a flexible linker attaching $X^2{}_1$ to $R^3$ by formation of a covalent bond with $X^2{}_1$ and by annealing to a complementary sequence of $R^3$, wherein the complementary sequence of $R^3$ does not comprise the sequence complementary to $R^7$ and wherein $R^2$ comprises a bifunctional chemical cross linker and is from 0 to 500 angstroms in length;
$R^3$ and $R^7$ comprise a pair of complementary nucleotide sequences from about 4 to about 15 nucleotides in length and having a free energy for association from about −5.5 kcal/mole to about −8.0 kcal/mole at a temperature from about 21° C. to about 40° C. and at a salt concentration from about 1 mM to about 100 mM;

R[4] and R[8] together comprise a detection means selected from the group consisting of fluorescence resonance energy transfer (FRET), time resolved-FRET, fluorescence life-time imaging, lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, residence time changes, and redox potential changes such that when R[3] and R[7] associate a detectable signal is produced;

R[5] is an aptamer that binds to a second epitope on the target molecule; and

R[6] is a flexible linker attaching $X^2_2$ to R[7] by formation of a covalent bond with $X^2_2$ and by annealing to a complementary sequence of R[7], wherein the complementary sequence of R[7] does not comprise the sequence complementary to R[3] and wherein R[6] comprises a bifunctional chemical cross linker and is from 0 to 500 angstroms in length.

Yet another embodiment of the invention encompasses a molecular biosensor comprising two epitope-binding agent constructs having formula (I)

wherein:

$X^1_1$ and $X^2_1$ are a first affinity binding pair;
$X^1_2$ and $X^2_2$ are a second affinity binding pair;
n and m are each an integer from 1 to 2;
R[1] is a peptide or antigen that binds to a first epitope on a target molecule;
R[2] is a flexible linker attaching $X^2_1$ to R[3];
R[3] and R[7] comprise a pair of complementary nucleotide sequences having a free energy for association from about −5.5 kcal/mole to about −8.0 kcal/mole at a temperature from about 21° C. to about 40° C. and at a salt concentration from about 1 mM to about 100 mM;
R[4] and R[8] together comprise a detection means such that when R[3] and R[7] associate a detectable signal is produced;
R[5] is an peptide or antigen that binds to a second epitope on the target molecule; and
R[6] is a flexible linker attaching $X^2_2$ to R[7].

In the foregoing embodiment, the target molecule may be an antibody that specifically recognizes the peptide or antigen via its variable region.

Yet another embodiment of the invention encompasses a molecular biosensor comprising two epitope-binding agent constructs having formula (I)

wherein:

$X^1_1$ and $X^2_1$ are a first affinity binding pair;
$X^1_2$ and $X^2_2$ are a second affinity binding pair;
n and m are each an integer from 1 to 2;
R[1] is an antibody that binds to a first epitope on a target molecule;
R[2] is a flexible linker attaching $X^2_1$ to R[3];
R[3] and R[7] comprise a pair of complementary nucleotide sequences having a free energy for association from about −5.5 kcal/mole to about −8.0 kcal/mole at a temperature from about 21° C. to about 40° C. and at a salt concentration from about 1 mM to about 100 mM;
R[4] and R[8] together comprise a detection means such that when R[3] and R[7] associate a detectable signal is produced;
R[5] is an antibody that binds to a second epitope on the target molecule; and
R[6] is a flexible linker attaching $X^2_2$ to R[7].

In the foregoing embodiment, the target molecule may be a peptide or antigen.

A further embodiment of the invention encompasses a molecular biosensor comprising two epitope-binding agent constructs having formula (I)

wherein:

$X^1_1$ and $X^2_1$ are a first affinity binding pair;
$X^1_2$ and $X^2_2$ are a second affinity binding pair;
n and m are each an integer from 1 to 2;
R[1] is an antigen or peptide that is specifically recognized by the variable region of a target antibody;
R[2] is a flexible linker attaching $X^2_1$ to R[3] by formation of a covalent bond with $X^2_1$ and by annealing to a complementary sequence of R[3], wherein the complementary sequence of R[3] does not comprise the sequence complementary to R[7] and wherein R[2] comprises a bifunctional chemical cross linker and is from 0 to 500 angstroms in length;
R[3] and R[7] comprise a pair of complementary nucleotide sequences from about 4 to about 15 nucleotides in length and having a free energy for association from about −5.5 kcal/mole to about −8.0 kcal/mole at a temperature from about 21° C. to about 40° C. and at a salt concentration from about 1 mM to about 100 mM;
R[4] and R[8] together comprise a detection means such that when R[3] and R[7] associate a detectable signal is produced;
R[5] is an antigen or peptide that is specifically recognized by the variable region of a target antibody; and
R[6] is a flexible linker attaching $X^2_2$ to R[7] by formation of a covalent bond with $X^2_2$ and by annealing to a complementary sequence of R[7], wherein the complementary sequence of R[7] does not comprise the sequence complementary to R[3] and wherein R[6] comprises a bifunctional chemical cross linker and is from 0 to 500 angstroms in length.

In each of the foregoing embodiments comprising two epitope-binding agent constructs having formula (I), the first and second epitope on the target molecule can bind to either a repeating epitope or distinct epitopes.

In each of the foregoing embodiments for molecular biosensors comprising two epitope-binding agent constructs having formula (I), the first epitope-binding agent construct, (R[1]—($X^1_1$)$_n$)—$X^2_1$—R[2]—R[3]—R[4], and the second epitope-binding agent construct, (R[5]—($X^1_2$)$_n$)—$X^2_2$—R[6]—R[7]—R[8], may optionally be attached to each other by a linker $R^{LA}$ to create tight binding bivalent ligands. Typically, the attachment is by covalent bond formation. Alternatively, the attachment may be by noncovalent bond formation. In one embodiment, $R^{LA}$ attaches R[1] of the first epitope-binding agent construct to R[5] of the second epitope-binding agent construct to form a molecule comprising:

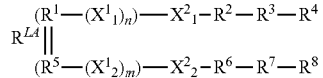

In a further embodiment, $R^{LA}$ attaches $X^1_1$ of the first nucleic acid construct to $X^1_2$ of the second nucleic acid construct to form a molecule comprising:

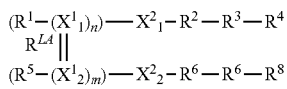

In yet another embodiment, $R^{LA}$ attaches $X^2_1$ of the first nucleic acid construct to $X^2_2$ of the second nucleic acid construct to form a molecule comprising:

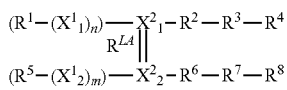

In yet another embodiment, $R^{LA}$ attaches $R^2$ of the first nucleic acid construct to $R^6$ of the second nucleic acid construct to form a molecule comprising:

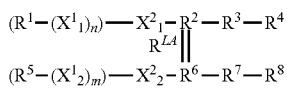

In yet another embodiment, $R^{LA}$ attaches $R^3$ of the first nucleic acid construct to $R^7$ of the second nucleic acid construct to form a molecule comprising:

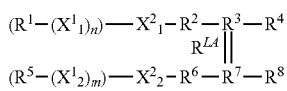

Generally speaking, $R^{LA}$ may be a nucleotide sequence from about 10 to about 100 nucleotides in length. The nucleotides comprising $R^{LA}$ may be any of the nucleotide bases in DNA or RNA (A, C, T, G in the case of DNA, or A, C, U, G in the case of RNA). In one embodiment, $R^{LA}$ is comprised of DNA bases. In another embodiment, $R^{LA}$ is comprised of RNA bases. In yet another embodiment, $R^{LA}$ is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^2$ and $R^6$ may be nucleotide mimics. Examples of nucleotide mimics include locked nucleic acids (LNA), peptide nucleic acids (PNA), and phosphorodiamidate morpholino oligomers (PMO). The nucleotides may be single-stranded, double-stranded, or a combination thereof. Alternatively, $R^{LA}$ may be a bifunctional chemical linker or a polymer of bifunctional chemical linkers. In one embodiment the bifunctional chemical linker is heterobifunctional. Suitable heterobifunctional chemical linkers include sulfoS-MCC (Sulfosuccinimidyl-4-(N-maleimidomethyl)cyclohexane-1-carboxylate), and lc-SPDP(N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Non-limiting examples of additional suitable linkers include polyethylene glycol such as PEG 4, PEG 8, PEG 12 (a 12-unit polyethylene glycol spacer) and the phosphoramidate form of Spacer 18 comprised of polyethylene glycol. In one embodiment, $R^{LA}$ is from about 1 to about 500 angstroms in length. In another embodiment, $R^{LA}$ is from about 20 to about 400 angstroms in length. In yet another embodiment, $R^{LA}$ is from about 50 to about 250 angstroms in length.

(b) Trivalent Molecular Sensors

In another alternative of the invention, the molecular biosensor will be trivalent. In a typical embodiment, the trivalent sensor will comprise a first epitope binding agent that binds to a first epitope on a target molecule, a first affinity binding pair, a first linker, a first signaling oligo, a first detection means, a second epitope binding agent that binds to a second epitope on the target molecule, a second affinity binding pair, a second linker, a second signaling oligo, a second detection means, a third epitope binding agent that binds to a third epitope on a target molecule, a third affinity binding pair, a third linker, a third signaling oligo, and a third detection means.

In one preferred embodiment, the molecular biosensor comprises three epitope-binding agent constructs, which together have formula (II):

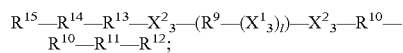

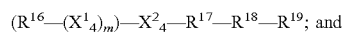

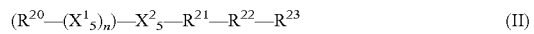 (II)

wherein:

$X^1_3$ and $X^2_3$ are a first affinity binding pair;
$X^1_4$ and $X^2_4$ are a second affinity binding pair;
$X^1_5$ and $X^2_5$ are a third affinity binding pair;
l is an integer from 2 to 4;
m and n are each an integer from 1 to 2;
$R^9$ is an epitope-binding agent that binds to a first epitope on a target molecule;
$R^{10}$ is a flexible linker attaching $X^2_3$ to $R^{11}$;
$R^{11}$ and $R^{22}$ comprise a first pair of complementary nucleotide sequences having a free energy for association from about −5.5 kcal/mole to about −8.0 kcal/mole at a temperature from about 21° C. to about 40° C. and at a salt concentration from about 1 mM b about 100 mM;
$R^{12}$ and $R^{23}$ together comprise a detection means such that when $R^{11}$ and $R^{22}$ associate a detectable signal is produced;
$R^{13}$ is a flexible linker attaching $X^2_3$ to $R^{14}$;
$R^{14}$ and $R^{18}$ comprise a second pair of complementary nucleotide sequences having a free energy for association from about −5.5 kcal/mole to about −8.0 kcal/mole at a temperature from about 21° C. to about 40° C. and at a salt concentration from about 1 mM to about 100 mM;
$R^{15}$ and $R^{19}$ together comprise a detection means such that when $R^{14}$ and $R^{18}$ associate a detectable signal is produced;
$R^{16}$ is an epitope-binding agent that binds to a second epitope on a target molecule;
$R^{17}$ is a flexible linker attaching $X^2_4$ to $R^{18}$;
$R^{20}$ is an epitope binding agent that binds to a third epitope on a target molecule; and
$R^{21}$ is a flexible linker attaching $X^2_5$ to $R^{22}$.

The choice of epitope binding agents, $R^9$, $R^{16}$ and $R^{20}$, in molecular biosensors having formula (II) can and will vary depending upon the particular target molecule. Generally speaking, suitable choices for $R^9$, $R^{16}$ and $R^{20}$ will include three agents that each recognize distinct epitopes on the same target molecule or on different target molecules, or three agents that each recognize the same repeating epitope on the same target molecule or on a different target molecule. In molecular biosensors having formula (II), $R^9$, $R^{16}$ and $R^{20}$ are independently selected from any suitable type of epitope binding agent. Non-limiting examples of suitable epitope binding agents, depending upon the target molecule (s), include agents selected from the group consisting of an aptamer, an antibody, an antibody fragment, a double-stranded DNA sequence, an antigen, modified nucleic acids, nucleic acid mimics, a ligand, a ligand fragment, a receptor, a receptor fragment, a protein, a polypeptide, a peptide, a coenzyme, a coregulator, an allosteric molecule, and an ion. In one embodiment, $R^9$, $R^{16}$ and $R^{20}$ are each aptamers having a sequence ranging in length from about 20 to about 110 nucleotide bases. In another embodiment, $R^9$, $R^{16}$, and $R^{20}$ are peptides. In yet another embodiment, $R^9$, $R^{16}$, and $R^{20}$ are antibodies or antibody fragments.

In another aspect of a molecular biosensor having formula (II), an affinity binding pair ($X^1_3/X^2_3$; $X^1_4/X^2_4$; $X^1_5/X^2_5$) non-covalently binds each epitope binding agent, $R^9$, $R^{16}$ and $R^{20}$, to a signaling oligonucleotide, $R^1/R^{14}$, $R^{18}$ and $R^{22}$, respectively, through a flexible linker, $R^{10}/R^{13}$, $R^{17}$ and $R^{21}$, respectively. In some embodiments, the affinity bind pair in each epitope-binding construct is the same. For example, the first, second and third affinity binding pair may each consist of biotin and a biotin binding partner. In other embodiments, the affinity bind pair in each epitope-binding construct is different. Suitable affinity binding pairs are described above in Section I. Generally speaking, the member of the affinity binding pair that is smaller in size is attached to the epitope binding agent in order to minimize steric interference of the epitope binding agent—target molecule interaction. By way of non-limiting example, biotin is preferably attached to epitope binding agent when the affinity binding pair consists of biotin and a biotin binding partner.

In another aspect of a molecular biosensor having formula (II), exemplary linkers, $R^{10}$ and $R^{21}$, will functionally keep $R^{11}$ and $R^{22}$ in close proximity such that when $R^9$ and $R^{20}$ each bind to the target molecule(s), $R^1$ and $R^{22}$ associate in a manner such that a detectable signal is produced by the detection means, $R^{12}$ and $R^{23}$. In addition, exemplary linkers, $R^{13}$ and $R^{17}$, will functionally keep $R^{14}$ and $R^{18}$ in close proximity such that when $R^9$ and $R^{16}$ each bind to the target molecule(s), $R^{14}$ and $R^{18}$ associate in a manner such that a detectable signal is produced by the detection means, $R^{15}$ and $R^{19}$. In one embodiment, the linkers utilized in molecular biosensors having formula (II) may each be a nucleotide sequence from about 10 to about 100 nucleotides in length. In one embodiment, the linkers are from 10 to about 25 nucleotides in length. In another embodiment, the linkers are from about 25 to about 50 nucleotides in length. In a further embodiment, the linkers are from about 50 to about 75 nucleotides in length. In yet another embodiment, the linkers are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment, the linkers are comprised of DNA bases. In another embodiment, the linkers are comprised of RNA bases. In yet another embodiment, the linkers are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^2$ and $R^6$ may be nucleotide mimics. Examples of nucleotide mimics include locked nucleic acids (LNA), peptide nucleic acids (PNA), and phosphorodiamidate morpholino oligomers (PMO). A nucleotide linker may be single-stranded, double-stranded, or a combination thereof. Alternatively, the linkers may be a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP(N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Non-limiting examples of additional suitable linkers include polyethylene glycol such as PEG 4, PEG 8, PEG 12 (a 12-unit polyethylene glycol spacer) and the phosphoramidate form of Spacer 18 comprised of polyethylene glycol, as well as those illustrated in the Examples. In one embodiment, the linkers are comprised of nucleotides and a bifunctional chemical linker. In another embodiment, the linkers are comprised of a heterobifunctional chemical linker and nucleotides. In still another embodiment, the linkers are comprised of a heterobifunctional chemical linker, a polyethylene glycol linker, and nucleotides. In a specific embodiment, the linkers are comprised of a SMCC linker and nucleotides. In another specific embodiment, the linkers are comprised of a SMCC linker, a polyethylene glycol linker and nucleotides. The nucleotides of the linkers may be complementary to a portion of the signaling oligos ($R^{11}$, $R^{22}$, $R^{14}$ and $R^{18}$), wherein the nucleotides of the linkers are not complementary to the sequences of $R^{11}$ and $R^{22}$ that are complementary to each other or the sequences of $R^{14}$ and $R^{18}$ that are complementary to each other. All or some of the nucleotides of the linkers may be complementary to a portion of the signaling oligos, wherein the nucleotides of the linkers are not complementary to the sequences of $R^{11}$ and $R^{22}$ that are complementary to each other or the sequences of $R^{14}$ and $R^{18}$ that are complementary to each other. In an embodiment where all or some of the nucleotides of the linkers are complementary to a portion of the signaling oligos, when the linkers comprising nucleotides complementary to a portion of $R^{11}$ and $R^{22}$ or $R^{14}$ and $R^{18}$ are contacted with $R^{11}$ and $R^{22}$ or $R^{14}$ and $R^{18}$ comprising nucleotides complementary to the linkers, the linkers anneal with the portion of $R^{11}$ and $R^{22}$ or $R^{14}$ and $R^{18}$ that is complementary to the linkers but do not anneal to the sequences of $R^{11}$ and $R^{22}$ that are complementary to each other or the sequences of $R^{14}$ and $R^{18}$ that are complementary to each other. In one embodiment, the linkers are from 0 to about 500 angstroms in length. In another embodiment, the linkers are from about 20 to about 400 angstroms in length. In yet another embodiment, the linkers are from about 50 to about 250 angstroms in length.

In another aspect of a molecular biosensor having formula (II), $R^{11}$ and $R^{22}$ comprise complementary nucleotide sequences having a length such that the complementary nucleotide sequences preferably do not associate unless $R^9$ and $R^{20}$ bind to separate epitopes on the target molecule(s).

In addition, $R^{14}$ and $R^{18}$ comprise complementary nucleotide sequences having a length such that the complementary nucleotide sequences preferably do not associate unless $R^9$ and $R^{16}$ bind to separate epitopes on the target molecule(s). The complementary nucleotide sequences of $R^{11}$ and $R^{22}$ and $R^{14}$ and $R^{18}$ may be from about 2 to about 20 nucleotides in length. In another embodiment, the complementary nucleotide sequences of $R^{11}$ and $R^{22}$ and $R^{14}$ and $R^{18}$ are from about 4 to about 15 nucleotides in length. In an exemplary embodiment, the complementary nucleotide sequences of $R^{11}$ and $R^{22}$ and $R^{14}$ and $R^{18}$ are from about 5 to about 7 nucleotides in length. In one embodiment, the complementary nucleotide sequences of $R^{11}$ and $R^{22}$ and $R^{14}$ and $R^{18}$ have a free energy for association from about −5.5 kcal/mole to about −8.0 kcal/mole as measured in the selection buffer conditions, defined below. In another embodiment, the complementary nucleotide sequences of $R^{11}$ and $R^{22}$ and $R^{14}$ and $R^{18}$ have a free energy for association from about −6.0 kcal/mole to about −8.0 kcal/mole as measured in the selection buffer conditions defined below. In yet another embodiment, the complementary nucleotide sequences of $R^{11}$ and $R^{22}$ and $R^{14}$ and $R^{18}$ have a free energy for association from about −7.0 kcal/mole to −8.0 kcal/mole in the selection buffer conditions. In a preferred embodiment, the complementary nucleotide sequences of $R^{11}$ and $R^{22}$ and $R^{14}$ and $R^{18}$ have a free energy for association of −7.5 kcal/mole in the selection buffer conditions described below. Preferably, in each embodiment the complementary nucleotide sequences of $R^{11}$ and $R^{22}$ and $R^{14}$ and $R^{18}$ are not complementary to any of $R^9$, $R^{16}$ or $R^{20}$ and are also not complementary to any of $R^{10}$, $R^{13}$, $R^{17}$, or $R^{21}$. In one embodiment, $R^{11}$ and $R^{22}$ and $R^{14}$ and $R^{18}$ further comprise a nucleotide sequence complementary to a nucleotide sequence of $R^{10}$ and $R^{21}$ and $R^{13}$ and $R^{17}$, respectively. In such an embodiment, the free energy for association described above for the complementary nucleotide sequences of $R^{11}$ and $R^{22}$ and $R^{14}$ and $R^{18}$ does not include the nucleotide sequences that are complementary to $R^{10}$ and $R^{21}$ and $R^{13}$ and $R^{17}$. The free energy for association solely includes the complementary nucleotide sequence of $R^{11}$ and $R^{22}$ and $R^{14}$ and $R^{18}$. In some embodiments, the nucleotide sequences of $R^{11}$ and $R^{22}$ and $R^{14}$ and $R^{18}$ that are complementary to the nucleotide sequences of $R^{10}$ and $R^{21}$ and $R^{13}$ and $R^{17}$, respectively, are from about 2 to about 40 nucleotides in length. In other embodiments, the nucleotide sequences of $R^{11}$ and $R^{22}$ and $R^{14}$ and $R^{18}$ that are complementary to the nucleotide sequences of $R^{10}$ and $R^{21}$ and $R^{13}$ and $R^{17}$, respectively, are from about 10 to about 30 nucleotides in length. In still other embodiments, the nucleotide sequences of $R^{11}$ and $R^{22}$ and $R^{14}$ and $R^{18}$ that are complementary to the nucleotide sequences of $R^{10}$ and $R^{21}$ and $R^{13}$ and $R^{17}$, respectively, are from about 15 to about 25 nucleotides in length. In still other embodiments, the nucleotide sequences of $R^{11}$ and $R^{22}$ and $R^{14}$ and $R^{18}$ that are complementary to the nucleotide sequences of $R^{10}$ and $R^{21}$ and $R^{13}$ and $R^{17}$, respectively, are from about 16 to about 20 nucleotides in length. In another aspect, any of $R^{11}$ and $R^{22}$ and $R^{14}$ and $R^{18}$ may further comprise a nucleotide sequence that is not complementary to a nucleotide sequence of $R^{10}$ and $R^{21}$ and $R^{13}$ and $R^{17}$, respectively, and is also not complementary to a nucleotide sequence of $R^{22}$ and $R^{11}$ and $R^{18}$ and $R^{14}$, respectively. In some embodiments, the nucleotide sequences of $R^{11}$ and $R^{22}$ and $R^{14}$ and $R^{18}$ that are not complementary to a nucleotide sequence of $R^{10}$ and $R^{21}$ and $R^{13}$ and $R^{17}$, respectively, and are also not complementary to a nucleotide sequence of $R^{22}$ and $R^{11}$ and $R^{18}$ and $R^{14}$, respectively, are from about 1 to about 10 nucleotides in length. In other embodiments, the nucleotide sequences of $R^{11}$ and $R^{22}$ and $R^{14}$ and $R^{18}$ that are not complementary to a nucleotide sequence of $R^{10}$ and $R^{21}$ and $R^{13}$ and $R^{17}$, respectively, and are also not complementary to a nucleotide sequence of $R^{22}$ and $R^{11}$ and $R^{18}$ and $R^{14}$, respectively, are from about 1 to about 5 nucleotides in length. In still other embodiments, the nucleotide sequences of $R^{11}$ and $R^{22}$ and $R^{14}$ and $R^{18}$ that are not complementary to a nucleotide sequence of $R^{10}$ and $R^{21}$ and $R^{13}$ and $R^{17}$, respectively, and are also not complementary to a nucleotide sequence of $R^{22}$ and $R^{11}$ and $R^{18}$ and $R^{14}$, respectively, are from about 1 to about 3 nucleotides in length.

In another aspect of a molecular biosensor having formula (II), $R^{12}$ and $R^{23}$ may together comprise several suitable detection means such that when $R^{11}$ and $R^{22}$ associate, a detectable signal is produced. In addition, $R^{15}$ and $R^{19}$ may together comprise several suitable detection means such that when $R^{14}$ and $R^{18}$ associate, a detectable signal is produced. Exemplary detections means suitable for use in the molecular biosensors include fluorescent resonance energy transfer (FRET), time resolved-FRET, fluorescence life-time imaging, lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, residence time changes, and redox potential changes.

III Three-Component Molecular Biosensors

Another aspect of the invention comprises three-component molecular biosensors. In certain embodiments, the three-component molecular biosensor will comprise an endonuclease restriction site. In alternative embodiments, the three-component molecular biosensor will not have an endonuclease restriction site.

(a) Biosensors with No Endonuclease Restriction Site

In one embodiment, the three-component biosensor will comprise: (1) a first epitope-binding agent construct that binds to a first epitope on a target molecule and comprises a first epitope binding agent, a first affinity binding pair, a first linker, a first signaling oligo, and a first detection means; (2) a second epitope-binding agent construct that binds to a second epitope on the target molecule and comprises a second epitope binding agent, a first affinity binding pair, a second linker, a second signaling oligo, and a second detection means; and (3) an oligonucleotide construct that comprises a first region that is complementary to the first oligo and a second region that is complementary to the second oligo. The first signaling oligo and second signaling oligo, as such, are not complementary to each other, but are complementary to two distinct regions on the oligonucleotide construct. Co-association of the two epitope-binding agent constructs with the target molecule results in hybridization of each of the signaling oligos to the oligonucleotide construct. Binding of the two signaling oligo to the oligonucleotide construct brings them into proximity such that a detectable signal is produced.

In an exemplary embodiment, the three-component molecular biosensor comprises three epitope-binding agent constructs, which together have formula (III):

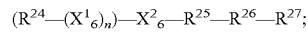

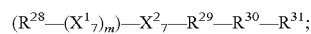

O                                                                              (III)

wherein:
- $X^1_6$ and $X^2_6$ are a first affinity binding pair;
- $X^1_7$ and $X^2_7$ are a second affinity binding pair;
- n and m are each an integer from 1 to 2;
- $R^{24}$ is an epitope-binding agent that binds to a first epitope on a target molecule;
- $R^{25}$ is a flexible linker attaching $X^2_6$ to $R^{26}$;
- $R^{26}$ and $R^{30}$ comprise a pair of nucleotide sequences that are not complementary to each other, but are complementary to two distinct regions on O;
- $R^{27}$ and $R^{31}$ together comprise a detection means such that when $R^{26}$ and
- $R^{30}$ associate with O, a detectable signal is produced;
- $R^{28}$ is an epitope-binding agent that binds to a second epitope on the target molecule;
- $R^{29}$ is a flexible linker attaching $X^2_7$ to $R^{30}$; and
- O is a nucleotide sequence comprising a first region that is complementary to $R^{26}$, and a second region that is complementary to $R^{30}$.

The choice of epitope binding agents, $R^{24}$ and $R^{28}$, in molecular biosensors having formula (III) can and will vary depending upon the particular target molecule. By way of example, when the target molecule is a protein, peptide or antigen, $R^{24}$ and $R^{28}$ may be an aptamer, or antibody. By way of further example, when the target molecule is an antibody, $R^{24}$ and $R^{28}$ may be an antigen or peptide specifically recognized by the variable region of a target antibody. In still another example, when $R^{24}$ and $R^{28}$ are double stranded nucleic acid the target molecule is typically a macromolecule that binds to DNA or a DNA binding protein. In an aspect, suitable choices for $R^{24}$ and $R^{28}$ will include two agents that each recognize distinct epitopes on the same target molecule. In another aspect, suitable choices for $R^{24}$ and $R^{28}$ will include two agents that each recognize distinct epitopes on different target molecules. In another aspect, suitable choices for $R^{24}$ and $R^{28}$ will include two agents that each recognize an identical repeating epitope on a single target. In molecular biosensors having formula (III), $R^{24}$ and $R^{28}$ are independently selected from any suitable type of epitope binding agent. Non-limiting examples of suitable epitope binding agents, depending upon the target, include agents selected from the group consisting of an aptamer, an antibody, an antibody fragment, a double-stranded DNA sequence, an antigen, modified nucleic acids, nucleic acid mimics, a ligand, a ligand fragment, a receptor, a receptor fragment, a protein, a polypeptide, a peptide, a coenzyme, a coregulator, an allosteric molecule, and an ion.

In an exemplary embodiment, $R^{24}$ and $R^{28}$ are each aptamers having a sequence ranging in length from about 20 to about 110 bases. In another embodiment, $R^{24}$ and $R^{28}$ are each antibodies selected from the group consisting of polyclonal antibodies, ascites, Fab fragments, Fab' fragments, monoclonal antibodies, and humanized antibodies. In an alternative embodiment, $R^{24}$ and $R^{28}$ are peptides or antigens. For example, $R^{24}$ and $R^{28}$ may be peptides or antigens specifically recognized by the variable region of an antibody. By way of non-limiting example, $R^{24}$ and $R^{28}$ may be peptides or antigens specifically recognized by the variable region of a disease or disorder specific antibody. In a preferred alternative of this embodiment, $R^{24}$ and $R^{28}$ are each monoclonal antibodies. In an additional embodiment, $R^{24}$ and $R^{28}$ are each double stranded DNA. In a further embodiment, $R^{24}$ is a double stranded nucleic acid and $R^{28}$ is an aptamer. In an additional embodiment, $R^{24}$ is an antibody and $R^{28}$ is an aptamer. In another additional embodiment, $R^{24}$ is an antibody and $R^{28}$ is a double stranded DNA. In yet another embodiment, $R^{24}$ is an antibody and $R^{28}$ is a peptide.

In another aspect of a molecular biosensor having formula (III), an affinity binding pair ($X^1_6/X^2_6$; $X^1_7/X^2_7$) non-covalently binds each epitope binding agent, $R^{24}$ and $R^{28}$, to a signaling oligonucleotide, $R^{26}$ and $R^{30}$, respectively, through a flexible linker, $R^{25}$ and $R^{29}$, respectively. In some embodiments, the affinity binding pair in each epitope-binding construct is the same. For example, the first and second affinity binding pair may each consist of biotin and a biotin binding partner. In other embodiments, the affinity bind pair in each epitope-binding construct is different. Suitable affinity binding pairs are described above in Section I. Generally speaking, the member of the affinity binding pair that is smaller in size is attached to the epitope binding agent in order to minimize steric interference of the epitope binding agent—target molecule interaction. By way of non-limiting example, biotin is preferably attached to epitope binding agent when the affinity binding pair consists of biotin and a biotin binding partner.

In another aspect of a molecular biosensor having formula (III), exemplary linkers, $R^{25}$ and $R^{29}$ may each be a nucleotide sequence from about 10 to about 100 nucleotides in length. In one embodiment, $R^{25}$ and $R^{29}$ are from 10 to about 25 nucleotides in length. In another embodiment, $R^{25}$ and $R^{29}$ are from about 25 to about 50 nucleotides in length. In a further embodiment, $R^{25}$ and $R^{29}$ are from about 50 to about 75 nucleotides in length. In yet another embodiment, $R^{25}$ and $R^{29}$ are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment $R^{25}$ and $R^{29}$ are comprised of DNA bases. In another embodiment, $R^{25}$ and $R^{29}$ are comprised of RNA bases. In yet another embodiment, $R^{25}$ and $R^{29}$ are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^{25}$ and $R^{29}$ may be nucleotide mimics. Examples of nucleotide mimics include locked nucleic acids (LNA), peptide nucleic acids (PNA), and phosphorodiamidate morpholino oligomers (PMO). A nucleotide linker may be single-stranded, double-stranded, or a combination thereof. Alternatively, $R^{25}$ and $R^{29}$ may be a bifunctional chemical linker or polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP (N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Non-limiting examples of additional suitable linkers include polyethylene glycol such as PEG 4, PEG 8, PEG 12 (a 12-unit polyethylene glycol spacer) and the phosphoramidate form of Spacer 18 comprised of polyethylene glycol, as well as those illustrated in the Examples. In one embodiment, $R^{25}$ and $R^{29}$ are comprised of nucleotides and a bifunctional chemical linker. In another embodiment, $R^{25}$ and $R^{29}$ are comprised of a heterobifunctional chemical linker and nucleotides. In still another embodiment, $R^{25}$ and $R^{29}$ are comprised of a heterobifunctional chemical linker, a polyethylene glycol linker, and nucleotides. In a specific embodiment, $R^{25}$ and $R^{29}$ are comprised of a SMCC linker and nucleotides. In another specific embodiment, $R^{25}$ and $R^{29}$ are comprised of a SMCC linker, a polyethylene glycol linker and nucleotides. The nucleotides of $R^{25}$ and $R^{29}$ may be complementary to a portion of the signaling oligos ($R^{26}$ and $R^{30}$, respectively), wherein the nucleotides of $R^{25}$ and $R^{29}$ are not complementary to the nucleotide sequences of $R^{26}$ and $R^{30}$ that are complementary to O (described below). All or some of the nucleotides of $R^{25}$ and $R^{29}$ may be complementary to a portion of $R^{26}$ and $R^{30}$ respectively, wherein the nucleotides of $R^{25}$ and $R^{29}$ are not complementary to the nucleotide sequences of $R^{26}$ and $R^{30}$ that are complementary to O. In an embodiment where all or some of the nucleotides of $R^{25}$ and $R^{29}$ are complementary to a portion of $R^{26}$ and $R^{30}$, respectively, when $R^{25}$ and $R^{29}$ comprising nucleotides complementary to a portion of $R^{26}$ and $R^{30}$ are contacted with $R^{26}$ and $R^{30}$ comprising nucleotides complementary to $R^{25}$ and $R^{29}$, respectively, $R^{25}$ and $R^{29}$ anneal with the portion of $R^{26}$ and $R^{30}$ that is complementary to $R^{25}$ and $R^{29}$ but do not anneal with the nucleotide sequences of $R^{26}$ and $R^{30}$ that are complementary to O. In one embodiment, $R^{25}$ and $R^{29}$ are from 0 to about 500 angstroms in length. In another embodiment, $R^{25}$ and $R^{29}$ are from about 20 to about 400 angstroms in length. In yet another embodiment, $R^{25}$ and $R^{29}$ are from about 50 to about 250 angstroms in length.

In another aspect of a molecular biosensor having formula (III), $R^{26}$ and $R^{30}$ comprise nucleotide sequences that are not complementary to each other, but that are complementary to two distinct regions of O. The region of $R^{26}$ and $R^{30}$ that is complementary to two distinct regions of O may be from about 2 to about 20 nucleotides in length. In another embodiment, the region of $R^{26}$ and $R^{30}$ that is complementary to two distinct regions of O may be from about 4 to about 15 nucleotides in length. In still another embodiment, the region of $R^{26}$ and $R^{30}$ that is complementary to two distinct regions of O may be from about 5 to about 7 nucleotides in length. Typically, the region of $R^{26}$ and $R^{30}$ that is complementary to two distinct regions of O has a free energy for association from about −5.5 kcal/mole to about −8.0 kcal/mole as measured in the selection buffer conditions, defined below. In certain embodiments, the region of $R^{26}$ and $R^{30}$ that is complementary to two distinct regions of O has a free energy for association from about −6.0 kcal/mole to about −8.0 kcal/mole as measured in the selection buffer conditions defined below. In certain other embodiments, the region of $R^{26}$ and $R^{30}$ that is complementary to two distinct regions of O has a free energy for association from about −7.0 kcal/mole to −8.0 kcal/mole in the selection buffer conditions. In a preferred embodiment, the region of $R^{26}$ and $R^{30}$ that is complementary to two distinct regions of O has a free energy for association of about −7.5 kcal/mole in the selection buffer conditions described below. Preferably, in each embodiment, the region of $R^{26}$ and $R^{30}$ that is complementary to two distinct regions of O is not complementary to $R^{24}$ and $R^{28}$ and is also not complementary to $R^{25}$ and $R^{29}$. In one embodiment, one or both of $R^{26}$ and $R^{30}$ further comprise a nucleotide sequence complementary to a nucleotide sequence of $R^{25}$ and $R^{29}$, respectively. In such an embodiment, the free energy for association described above for the region of $R^{26}$ and $R^{30}$ that is complementary to two distinct regions of O does not include the nucleotide sequences that are complementary to $R^{25}$ and $R^{29}$. The free energy for association solely includes the region of $R^{26}$ and $R^{30}$ that is complementary to two distinct regions of O. In some embodiments, the nucleotide sequences of $R^{26}$ and $R^{30}$ that are complementary to the nucleotide sequences of $R^{25}$ and $R^{29}$, respectively, are from about 2 to about 40 nucleotides in length. In other embodiments, the nucleotide sequences of $R^{26}$ and $R^{30}$ that are complementary to the nucleotide sequences of $R^{25}$ and $R^{29}$, respectively, are from about 10 to about 30 nucleotides in length. In still other embodiments, the nucleotide sequences of $R^{26}$ and $R^{30}$ that are complementary to the nucleotide sequences of $R^{25}$ and $R^{29}$, respectively, are from about 15 to about 25 nucleotides in length. In still other embodiments, the nucleotide sequences of $R^{26}$ and $R^{30}$ that are complementary to the nucleotide sequences of $R^{25}$ and $R^{29}$, respectively, are from about 16 to about 20 nucleotides in length. In another aspect, one or both of $R^{26}$ and $R^{30}$ may further comprise a nucleotide sequence that is not complementary to a nucleotide sequence of $R^{25}$ and $R^{29}$, respectively, and is also not complementary to a distinct region of O. In some embodiments, the nucleotide sequences of $R^{26}$ and $R^{30}$ that are not complementary to a nucleotide sequence of $R^{25}$ and $R^{29}$, respectively, and are also not complementary to a distinct region of O, are from about 1 to about 10 nucleotides in length. In other embodiments, the nucleotide sequences of $R^{26}$ and $R^{30}$ that are not complementary to a nucleotide sequence of $R^{25}$ and $R^{29}$, respectively, and are also not complementary to a distinct region of O, are from about 1 to about 5 nucleotides in length. In still other embodiments, the nucleotide sequences of $R^{26}$ and $R^{30}$ that are not complementary to a nucleotide sequence of $R^{25}$ and $R^{29}$, respectively, and are also not complementary to a distinct region of O, are from about 1 to about 3 nucleotides in length.

In another aspect of a molecular biosensor having formula (III), $R^{27}$ and $R^{31}$ may together comprise several suitable detection means such that when $R^{26}$ and $R^{30}$ each bind to complementary, distinct regions on O, a detectable signal is produced. Exemplary detections means suitable for use in the molecular biosensors include fluorescent resonance energy transfer (FRET), time resolved-FRET, fluorescence life-time imaging, lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, residence time changes, and redox potential changes.

In another aspect of a molecular biosensors having formula (III), $R^{27}$ and $R^{31}$ are not present. In these embodiments the binding of $R^{26}$ and $R^{30}$ to complementary, distinct regions on O may be detected by changes in mass, electrical, or optical properties of the biosensor upon target binding. In these embodiments, the change in mass, electrical, or optical properties that result when $R^{24}$ and $R^{28}$ bind to the target, and $R^{26}$ and $R^{30}$ bind to O, result in a detectable signal. For instance, the detection means may include surface plasmon resonance, optical ring resonance, and silicon nanowire sensors.

For molecular biosensors having formula (III), O comprises a first region that is complementary to $R^{26}$, and a second region that is complementary to $R^{30}$. O may be from about 8 to about 100 nucleotides in length. In other embodiments, O is from about 10 to about 15 nucleotides in length, or from about 15 to about 20 nucleotides in length, or from about 20 to about 25 nucleotides in length, or from about 25 to about 30 nucleotides in length, or from about 30 to about 35 nucleotides in length, or from about 35 to about 40 nucleotides in length, or from about 40 to about 45 nucleotides in length, or from about 45 to about 50 nucleotides in length, or from about 50 to about 55 nucleotides in length, or from about 55 to about 60 nucleotides in length, or from about 60 to about 65 nucleotides in length, or from about 65 to about 70 nucleotides in length, or from about 70 to about 75 nucleotides in length, or from about 75 to about 80 nucleotides in length, or from about 80 to about 85 nucleotides in length, or from about 85 to about 90 nucleotides in length, or from about 90 to about 95 nucleotides in length, or greater than about 95 nucleotides in length.

In an exemplary embodiment, O will comprise formula (IV):

$$R^{32}-R^{33}-R^{34}-R^{35}-R^{36} \quad (IV)$$

wherein:
$R^{32}$, $R^{34}$, and $R^{36}$ are nucleotide sequences not complementary to any of $R^{26}$, $R^{30}$, $R^{33}$, or $R^{35}$. $R^{32}$, $R^{34}$, and $R^{36}$ may independently be from about 2 to about 20 nucleotides in length. In other embodiments, $R^{32}$, $R^{34}$, and $R^{36}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length;

$R^{33}$ is a nucleotide sequence that is complementary to $R^{26}$, and $R^{35}$ is a nucleotide sequence that is complementary to $R^{30}$.

$R^{33}$ and $R^{35}$ generally have a length such that the free energy of association between the complementary region of $R^{33}$ and $R^{26}$ and $R^{35}$ and $R^{30}$ is from about −5 to about −12 kcal/mole at a temperature from about 21° C. to about 40° C. and at a salt concentration from about 1 mM to about 100 mM. In other embodiments, the free energy of association between the complementary region of $R^{33}$ and $R^{26}$ and $R^{35}$ and $R^{30}$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $R^{33}$ and $R^{35}$ may range from about 4 to about 20 nucleotides in length. In other embodiments, $R^{33}$ and $R^{35}$ may be about 4, about 5, about 6, about 7, about 8, about 9, about 10, about 11, about 12, about 13, about 14, about 15, about 16, about 17, about 18, about 19, or greater than about 10 nucleotides in length.

In yet another embodiment of the invention, O will comprise formula (IV);
wherein:
$R^{32}$, $R^{34}$, and $R^{36}$ are nucleotide sequences not complementary to any of $R^{26}$, $R^{30}$, $R^{33}$, or $R^{35}$. $R^{32}$, $R^{34}$, and $R^{36}$ may independently be from about 2 to about 20 nucleotides in length. In other embodiments, $R^{32}$, $R^{34}$, and $R^{36}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length;

$R^{33}$ is a nucleotide sequence complementary to all or part of $R^{26}$, and $R^{35}$ is a nucleotide sequence that is complementary to all or part of $R^{30}$.

$R^{33}$ and $R^{35}$ generally have a length such that the free energy of association between the complementary region of $R^{33}$ and $R^{26}$ and $R^{35}$ and $R^{30}$ is from about −5 to about −12 kcal/mole at a temperature from about 21° C. to about 40° C. and at a salt concentration from about 1 mM to about 100 mM.

(b) Biosensors with an Endonuclease Restriction Site
i. Formula (V)

Figure 16:
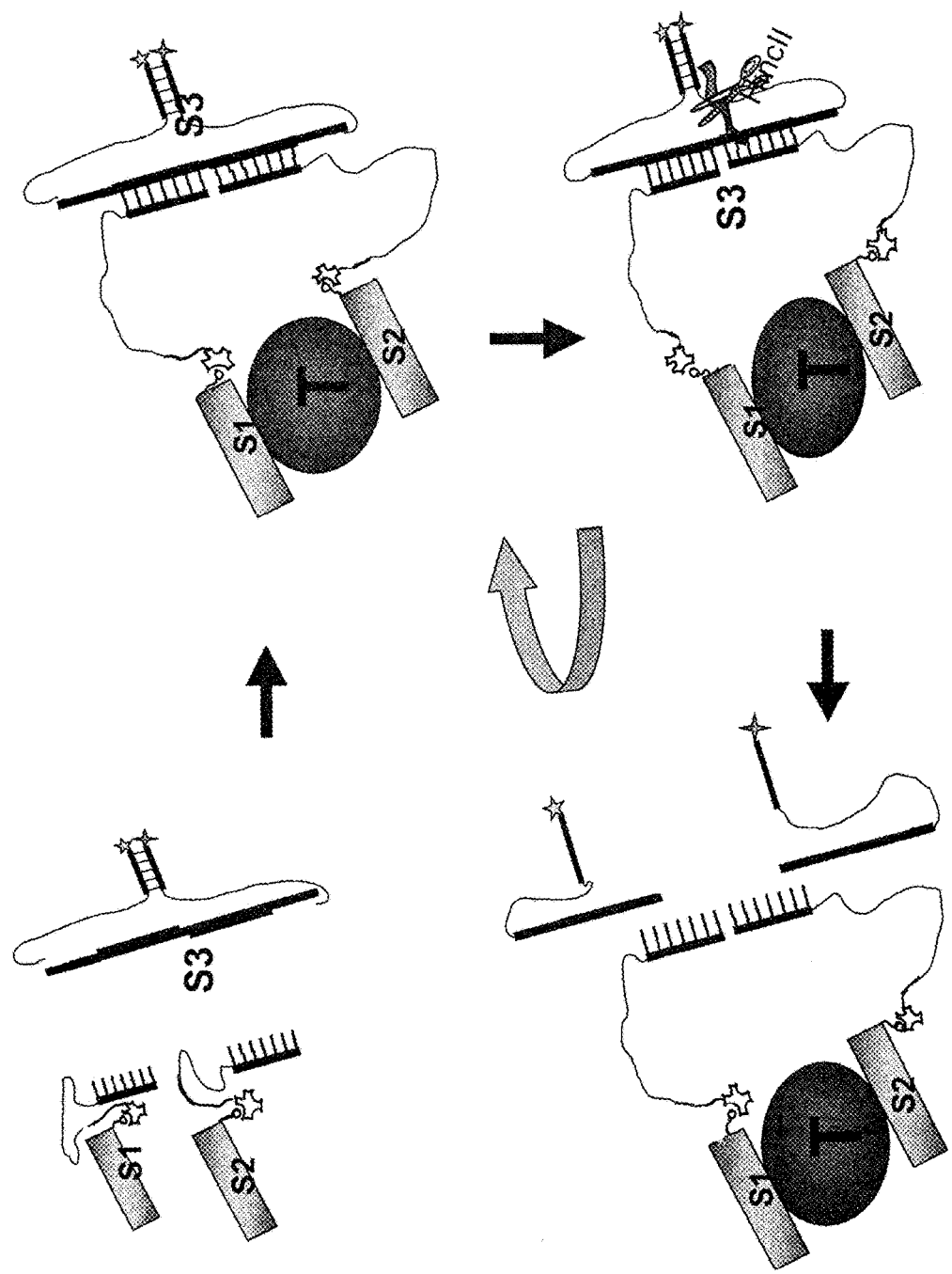
FIG. 16 depicts homogenous signal amplification utilizing the three-component sensor design. Hybridized S3 comprises a restriction endonuclease recognition site.

In an alternative embodiment, the three-component biosensor will comprise: (1) a first epitope-binding agent construct that binds to a first epitope on a target molecule and comprises a first epitope binding agent, a first affinity binding pair, a first linker, and a first signaling oligo; (2) a second epitope-binding agent construct that binds to a second epitope on the target molecule and comprises a second epitope binding agent, a second affinity binding pair, a second linker, a second signaling oligo and (3) an oligonucleotide construct that comprises a first region that is complementary to the first signaling oligo, a second region that is complementary to the second signaling oligo, two flexible linkers, an endonuclease restriction site overlapping the first and the second regions complementary to the first and the second signaling oligos, and a pair of complementary nucleotides with detection means. The first signaling oligo and second signaling oligo are not complementary to each other, but are complementary to two distinct regions on the oligonucleotide construct. Referring to FIG. 16, when the oligonucleotide construct is intact, the complementary nucleotides are annealed and produce a detectable signal. Co-association of the two epitope-binding agent constructs with the target molecule results in hybridization of each signaling oligo to the oligonucleotide construct. The signaling oligos hybridize to two distinct locations on the oligonucleotide construct such that a double-stranded DNA molecule containing the restriction site is produced, with a gap between the signaling oligos located exactly at the site of endonuclease cleavage in one strand of the double-stranded DNA substrate. When a restriction endonuclease is present, accordingly, it will cleave the oligonucleotide construct only when the target is present (i.e., when the signaling oligos are bound to the oligonucleotide construct). Upon this cleavage, the detection means present on the oligonucleotide are separated, resulting in no detectable signal. Upon dissociation of the cleaved oligonucleotide construct, another oligonucleotide construct may hybridize with the signaling oligos of the two epitope-binding agents co-associated with the target and the cleavage reaction may be repeated. This cycle of hybridization and cleavage may be repeated many times resulting in cleavage of multiple oligonucleotide constructs per one complex of the two epitope-binding agents with the target.

In exemplary alternative of this embodiment, the three-component molecular biosensor comprises three epitope-binding agent constructs, which together have formula (V):

$(R^{37}—(X^1_8)_n)—X^2_8—R^{38}—R^{39};$ $(R^{40}—(X^1_9)_m)—X^2_9—R^{41}—R^{42};$

O                                                                                       (V)

wherein:
- $X^1_8$ and $X^2_8$ are a first affinity binding pair;
- $X^1_9$ and $X^2_9$ are a second affinity binding pair;
- n and m are each an integer from 1 to 2;
- $R^{37}$ is an epitope-binding agent that binds to a first epitope on a target molecule;
- $R^{38}$ is a flexible linker attaching $X^2_8$ to $R^{39}$;
- $R^{39}$ and $R^{42}$ are a pair of nucleotide sequences that are not complementary to each other, but are complementary to two distinct regions on O;
- $R^{40}$ is an epitope-binding agent that binds to a second epitope on the target molecule;
- $R^{41}$ is a flexible linker attaching $X^2_9$ to $R^{42}$; and O comprises:
- $R^{47}—R^{46}—R^{43}—R^{44}—R^{45}$, where
- $R^{43}$ is a nucleotide construct comprising an endonuclease restriction site, a first region that is complementary to $R^{39}$, and a second region that is complementary to $R^{42}$.
- $R^{44}$ is a first flexible linker;
- $R^{45}$ is a first nucleotide sequence that is complementary to $R^{47}$ attached to an optional detection means;
- $R^{46}$ is a second flexible linker;
- $R^{47}$ is a second nucleotide sequence that is complementary to $R^{45}$ attached to a second optional detection means; and
- $R^{44}$ attaches $R^{43}$ to $R^{45}$ and $R^{46}$ attaches $R^{43}$ to $R^{47}$.

Suitable linkers, epitope binding agents, and detection means for three-component molecular biosensors having formula (V) are the same as three component molecular biosensors having formula (III). Suitable, endonuclease restriction sites comprising $R^{43}$ include sites that are recognized by restriction enzymes that cleave double stranded nucleic acid, but not single stranded nucleic acid. By way of non-limiting example, these sites include AccI, AgeI, BamHI, BgI, BgIII, BsiWI, BstBI, ClaI, CviQI, DdeI, DpnI, DraI, EagI, EcoRI, EcoRV, FseI, FspI, HaeII, HaeIII, HhaI, Hinc II, HinDIII, HpaI, HpaII, KpnI, KspI, MboI, MfeI, NaeI, NarI, NcoI, NdeI, NheI, NotI, PhoI, PstI, PvuI, PvuII, SacI, SacII, SaiI, SbfI, SmaI, SpeI, SphI, StuI, TaqI, TfiI, TliI, XbaI, XhoI, XmaI, XmnI, and ZraI. Optionally, $R^{43}$ may comprise nucleotide spacers that precede or follow one or more of the endonuclease restriction site, the first region that is complementary to $R^{39}$, and/or the second region that is complementary to $R^{42}$.

ii. Formula (VI)

In an alternative embodiment of the three-component biosensor, the biosensor comprises three constructs, which together have formula (VI):

$(R^{37}—(X^1_8)_n)—X^2_8—R^{38}—R^{39};$ $(R^{40}—(X^1_9)_m)—X^2_9—R^{41}—R^{42};$ and at least one $R^{55}—R^{56};$                                                (VI)

wherein:
- $R^{37}$, $R^{38}$, $R^{39}$, $R^{40}$, $R^{41}$, $R^{42}$, $X^1_8$, $X^2_8$, $X^1_9$, $X^2_9$, n, and m are defined as in formula (V);
- $R^{39}$ and $R^{42}$ are a first pair of nucleotide sequences that are complementary to two distinct regions on $R^{56}$;
- $R^{56}$ is a nucleotide construct comprising a first region that is complementary to $R^{39}$ and a second region that is complementary to $R^{42}$, such that when $R^{39}$ and $R^{42}$ associate with $R^{56}$, an endonuclease restriction site is reconstituted; and
- $R^{55}$ is optionally a signaling molecule.

$R^{37}$, $R^{38}$, $R^{39}$, $R^{40}$, $R^{41}$, $R^{42}$, $X^1_8$, $X^2_8$, $X^1_9$, $X^2_9$, m and n may be as defined above for three component molecular biosensors having formula (V). $R^{56}$ is the same as $R^{43}$ of formula (V).

In some embodiments for molecular biosensors having Formula (VI), $R^{55}$ may comprise two signaling molecules, each attached to one strand of a double-stranded nucleotide sequence comprising $R^{56}$. Cleavage of the restriction enzyme recognition site results in the release and separation of the two signaling molecules, resulting in a detectable and quantifiable change in signal intensity. Exemplary detections means suitable for use in the molecular biosensors include fluorescent resonance energy transfer (FRET), time resolved-FRET, fluorescence life-time imaging, lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, residence time changes, and redox potential changes.

In an alternative embodiment, $R^{55}$ is not present. In these embodiments, the binding of $R^{39}$ and $R^{42}$ to complementary, distinct regions on $R^{56}$ may be detected by changes in mass, electrical, or optical properties of the biosensor upon target binding. In these embodiments, the change in mass, electrical, or optical properties that result when $R^{37}$ and $R^{40}$ bind to the target, and $R^{39}$ and $R^{42}$ bind to $R^{56}$, result in a detectable signal. For instance, the detection means may include surface plasmon resonance, optical ring resonance, and silicon nanowire sensors.

iii. Formula (VII)

In an alternative embodiment, a three-component molecular biosensor with a restriction endonuclease recognition site will comprise an oligonucleotide construct attached to a solid support. Generally speaking, co-association of the two epitope-binding agent constructs with a target molecule results in hybridization of each single stranded nucleic acid sequence to the oligonucleotide construct, producing a tripartite double-stranded nucleic acid molecule that contains a restriction endonuclease recognition site. In the presence of a restriction endonuclease, the oligonucleotide construct may be cleaved to release a signaling molecule from the solid support.

For example, in some embodiments the three-component molecular biosensor comprises at least three constructs, which together have formula (VII):

$(R^{37}—(X^1_8)_n)—X^2_8—R^{38}—R^{39};$ $(R^{40}—(X^1_9)_m)—X^2_9—R^{41}—R^{42};$ and at least one $R^{55}—R^{56}—R^{57};$                                       (VII)

wherein:
- $R^{37}$, $R^{38}$, $R^{39}$, $R^{40}$, $R^{41}$, $R^{42}$, $X^1_8$, $X^2_8$, $X^1_9$, $X^2_9$, n, and m are defined as in formula (V); and
- $R^{57}$ is a solid support.

$R^{55}$ of formula (VII) is an optional signaling molecule. Suitable signaling molecules are known in the art. Non-limiting examples may include luminescent molecules, chemiluminescent molecules, fluorochromes, fluorescent quenching agents, colored molecules, radioisotopes, scintillants, massive labels (for detection via mass changes), biotin, avidin, streptavidin, protein A, protein G, antibodies or fragments thereof, Grb2, polyhistidine, Ni$^{2+}$, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present invention.

For molecular biosensors having formula (VII), $R^{56}$ comprises a first region that is complementary to $R^{39}$, and a second region that is complementary to $R^{42}$. $R^{56}$ may be as described above for O. When $R^{39}$ and $R^{42}$ associate with $R^{56}$, a tripartite double-stranded DNA molecule is formed that contains a restriction endonuclease recognition sequence. In the presence of a restriction endonuclease, $R^{56}$ is cleaved, optionally releasing $R^{55}$ from the solid support $R^{57}$. In an exemplary embodiment, $R^{39}$ and $R^{42}$ do not form a stable complex with $R^{56}$ after $R^{56}$ is cleaved, freeing $R^{39}$ and $R^{42}$ to bind to another $R^{56}$ and repeat the cleavage cycle. This amplifies the biosensor signal.

In an exemplary embodiment, $R^{56}$ will comprise formula (VIII):

(VIII)

wherein:
  $R^{58}$ and $R^{61}$ are single-stranded nucleotide sequences not complementary to any of $R^{37}$, $R^{38}$, $R^{39}$, $R^{40}$, $R^{41}$, or $R^{42}$;
  $R^{59}$ is a nucleotide sequence complementary to $R^{39}$; and
  $R^{60}$ is a nucleotide sequence that is complementary to $R^{42}$.

In some embodiments, $R^{58}$ and $R^{61}$ may independently be from about 0 to about 20 nucleotides in length. In other embodiments, $R^{58}$ and $R^{61}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length.

Generally speaking, $R^{59}$ and $R^{60}$ have a length such that the free energy of association between $R^{59}$ and $R^{39}$ and $R^{60}$ and $R^{42}$ is from about −5 to about −12 kcal/mole at a temperature from about 21° C. to about 40° C. and at a salt concentration from about 1 mM to about 100 mM. In other embodiments, the free energy of association between $R^{59}$ and $R^{39}$ and $R^{60}$ and $R^{42}$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $R^{59}$ and $R^{60}$ may range from about 4 to about 20 nucleotides in length. In other embodiments, $R^{59}$ and $R^{60}$ may be about 4, about 5, about 6, about 7, about 8, about 9, about 10, about 11, about 12, about 13, about 14, about 15, about 16, about 17, about 18, about 19, or greater than about 10 nucleotides in length.

In one embodiment, when $R^{56}$ comprises formula (VIII), the cleavage site of the restriction endonuclease recognition sequence produced by the association of $R^{39}$ and $R^{42}$ with $R^{56}$ is located between $R^{59}$ and $R^{60}$. In this manner, in the presence of a suitable restriction endonuclease, $R^{56}$ will be cleaved between $R^{59}$ and $R^{60}$, but $R^{39}$ and $R^{42}$ remain intact. Suitable restriction endonuclease recognition sequences are recognized by restriction enzymes that cleave double stranded nucleic acid, but not single stranded nucleic acid. Such enzymes and the corresponding recognition sites are known in the art. By way of non-limiting example, these enzymes may include AccI, AgeI, BamHI, BgII, BgIII, BsiWI, BstBI, ClaI, CviQI, DdeI, DpnI, DraI, EagI, EcoRI, EcoRV, FseI, FspI, HaeII, HaeIII, HhaI, HincII, HinDIII, HpaI, HpaII, KpnI, KspI, MboI, MfeI, NaeI, NarI, NcoI, NdeI, NheI, NotI, PhoI, PstI, PvuI, PvuII, SacI, SacI, SaiI, SbfI, SmaI, SpeI, SphI, StuI, TaqI, TliI, TfiI, XbaI, XhoI, XmaI, XmnI, and ZraI.

In another exemplary embodiment, $R^{56}$ will comprise formula (IX):

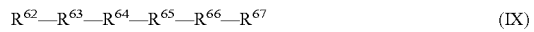

(IX)

wherein:
  $R^{63}$, $R^{64}$, $R^{65}$, and $R^{66}$ are single stranded oligonucleotide sequences not complementary to each other or any of $R^{37}$, $R^{38}$, $R^{39}$, $R^{40}$, $R^{41}$, or $R^{42}$;
  $R^{62}$ and $R^{67}$ are double-stranded nucleic acid sequences;
  $R^{64}$ is a nucleotide sequence complementary to $R^{39}$; and
  $R^{65}$ is a nucleotide sequence that is complementary to $R^{42}$.
  $R^{63}$ and $R^{66}$ may independently be from about 0 to about 20 nucleotides in length. In other embodiments, $R^{63}$ and $R^{66}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length;
  $R^{62}$ and $R^{67}$ may independently be from about 0 to about 20 base pairs in length. In other embodiments, $R^{62}$ and $R^{67}$ may independently be from about 2 to about 4 base pairs in length, or from about 4 to about 6 base pairs in length, or from about 6 to about 8 base pairs in length, or from about 8 to about 10 base pairs in length, or from about 10 to about 12 base pairs in length, or from about 12 to about 14 base pairs in length, or from about 14 to about 16 base pairs in length, or from about 16 to about 18 base pairs in length, or from about 18 to about 20 base pairs in length, or greater than about 20 base pairs in length;
  $R^{64}$ and $R^{65}$ generally have a length such that the free energy of association between $R^{64}$ and $R^{39}$ and $R^{65}$ and $R^{42}$ is from about −5 to about −12 kcal/mole at a temperature from about 21° C. to about 40° C. and at a salt concentration from about 1 mM to about 100 mM. In other embodiments, the free energy of association between $R^{64}$ and $R^{39}$ and $R^{65}$ and $R^{42}$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $R^{64}$ and $R^{65}$ may range from about 4 to about 20 nucleotides in length. In other embodiments, $R^{64}$ and $R^{65}$ may be about 4, about 5, about 6, about 7, about 8, about 9, about 10, about 11, about 12, about 13, about 14, about 15, about 16, about 17, about 18, about 19, or greater than about 20 nucleotides in length.

In yet another exemplary embodiment, $R^{56}$ may comprise formula (X):

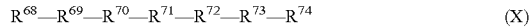

wherein:
$R^{69}$, $R^{70}$, $R^{72}$, $R^{73}$ and $R^{74}$ are single stranded oligonucleotide sequences independently not complementary to each other or any of $R^{37}$, $R^{38}$, $R^{39}$, $R^{40}$, $R^{41}$, Or $R^{42}$;
$R^{68}$ and $R^{71}$ are double-stranded nucleic acid sequences;
$R^{69}$ is a nucleotide sequence complementary to $R^{39}$; and
$R^{73}$ is a nucleotide sequence that is complementary to $R^{42}$.
$R^{70}$, $R^{72}$, and $R^{74}$ may independently be from about 0 to about 20 nucleotides in length. In other embodiments, $R^{70}$, $R^{72}$, and $R^{74}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length.
$R^{68}$ and $R^{71}$ may independently be from about 0 to about 20 base pairs in length. In other embodiments, $R^{68}$ and $R^{71}$ may independently be from about 2 to about 4 base pairs in length, or from about 4 to about 6 base pairs in length, or from about 6 to about 8 base pairs in length, or from about 8 to about 10 base pairs in length, or from about 10 to about 12 base pairs in length, or from about 12 to about 14 base pairs in length, or from about 14 to about 16 base pairs in length, or from about 16 to about 18 base pairs in length, or from about 18 to about 20 base pairs in length, or greater than about 20 base pairs in length.
$R^{69}$ and $R^{73}$ generally have a length such that the free energy of association between $R^{69}$ and $R^{39}$ and $R^{73}$ and $R^{42}$ is from about −5 to about −12 kcal/mole at a temperature from about 21° C. to about 40° C. and at a salt concentration from about 1 mM to about 100 mM. In other embodiments, the free energy of association between $R^{69}$ and $R^{39}$ and $R^{73}$ and $R^{42}$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $R^{69}$ and $R^{73}$ may range from about 4 to about 20 nucleotides in length. In other embodiments, $R^{69}$ and $R^{73}$ may be about 4, about 5, about 6, about 7, about 8, about 9, about 10, about 11, about 12, about 13, about 14, about 15, about 16, about 17, about 18, about 19, or greater than about 10 nucleotides in length.

When $R^{56}$ comprises formula (IX) or formula (X), a cleavage site of a restriction endonuclease recognition sequence produced by the association of $R^{39}$ and $R^{42}$ with $R^{56}$ may be located within either $R^{62}$ for formula (IX) or $R^{68}$ for formula (X), $R^{67}$ for formula (IV), $R^{71}$ for formula (V), or a combination thereof. Suitable restriction endonuclease recognition sequences for these embodiments are recognized by restriction enzymes that cleave double stranded nucleic acid outside the recognition sequence of the restriction enzyme. Such enzymes and the corresponding recognition and cleavage sites are known in the art. By way of non-limiting example, these sites may include AcuI, AlwI, BaeI, BbsI, BbvI, BccI, BceAI, BcgI, BciVI, BfuAI, BmrI, BpmI, BpuEI, BsaI, BsaXI, BseRI, BsgI, BsmAI, BsmBI, BsmFI, BspCNI, BspMI, BspQI, BtgZI, CspCI, EarI, EciI, EcoP15I, FokI, HgaI, HphI, HpyAV, MboII, MlyI, MmeI, MmeAIII, PleI, SapI, SfaNI.

In some embodiments for molecular biosensors having Formula (IX) or Formula (X), $R^{55}$ may comprise two signaling molecules, each attached to one strand of a double-stranded nucleotide sequence comprising $R^{56}$. Cleavage of the restriction enzyme recognition site results in the release and separation of the two signaling molecules, resulting in a detectable and quantifiable change in signal intensity. Exemplary detections means suitable for use in the molecular biosensors include fluorescent resonance energy transfer (FRET), time resolved-FRET, fluorescence life-time imaging, lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, residence time changes, and redox potential changes.

In an alternative embodiment, $R^{55}$ is not present. In these embodiments, the binding of $R^{39}$ and $R^{42}$ to complementary, distinct regions on $R^{56}$ may be detected by changes in mass, electrical, or optical properties of the biosensor upon target binding. In these embodiments, the change in mass, electrical, or optical properties that result when $R^{37}$ and $R^{40}$ bind to the target, and $R^{39}$ and $R^{42}$ bind to $R^{56}$, result in a detectable signal. For instance, the detection means may include surface plasmon resonance, optical ring resonance, and silicon nanowire sensors.

In some embodiments, $R^{57}$ is a solid support having $R^{56}$ attached thereto. Non-limiting examples of suitable solid supports may include microtitre plates, test tubes, beads, resins and other polymers, as well as other surfaces either known in the art or described herein. The solid support may be a material that may be modified to contain discrete individual sites appropriate for the attachment or association of the construct and is amenable to at least one detection method. Non-limiting examples of solid support materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. The size and shape of the solid support may also vary without departing from the scope of the invention. A solid support may be planar, a solid support may be a well, i.e. a 364 well plate, or alternatively, a solid support may be a bead or a slide.

$R^{56}$ may be attached to $R^{57}$ in a wide variety of ways, as will be appreciated by those in the art. $R^{56}$, for example, may either be synthesized first, with subsequent attachment to the solid support, or may be directly synthesized on the solid support. $R^{57}$ and $R^{56}$ may be derivatized with chemical functional groups for subsequent attachment of the two. For example, the solid support may be derivatized with a chemical functional group including, but not limited to, amino groups, carboxyl groups, oxo groups or thiol groups. Using these functional groups, the $R^{56}$ may be attached using functional groups either directly or indirectly using linkers. Alternatively, $R^{56}$ may also be attached to the surface non-covalently. For example, a biotinylated $R^{56}$ can be prepared, which may bind to surfaces covalently coated with streptavidin, resulting in attachment. Alternatively, $R^{56}$ may be synthesized on the surface using techniques such as photopolymerization and photolithography. Additional methods of attaching $R^{56}$ to a surface and methods of synthesizing nucleic acids on surfaces are well known in the art, i.e. VLSIPS technology from Affymetrix (e.g., see U.S. Pat. No. 6,566,495, and Rockett and Dix, "DNA arrays: technology, options and toxicological applications," Xenobiotica 30(2):155-177, all of which are hereby incorporated by reference in their entirety).

(c) Further Sensor Variants

In each of the foregoing embodiments for molecular biosensors, the first epitope-binding agent construct, and the second epitope-binding agent construct may optionally be attached to each other by a linker $R^{LA}$ to create tight binding bivalent ligands. Typically, the attachment is by covalent bond formation. Alternatively, the attachment may be by non-covalent bond formation. Generally speaking, $R^{LA}$ may be a nucleotide sequence as described above.

In other various embodiments O may be comprised of A and B1-B2-B3, such that A is similar to $R^{56}$ and A hybridizes to B1 (B1 may be defined as, for instance, similar to $R^{41}$). B1 may be connected to B3 (may be defined as, for instance, similar to $R^{57}$) via B2 (may be defined as, for instance, similar to $R^{37}$). Similarly, in an exemplary embodiment, an epitope-binding agent construct may comprise E1-E2-E3 and F1-F2-F3, such that E1 corresponds to $R^{38}$; E2, E3, F1, and F2 together comprise $R^{37}$; and F3 corresponds to $R^{36}$. Specifically, E3 is a single-stranded nucleic acid that hybridizes to F1. Conversely, F1 is a single-stranded nucleic acid that hybridizes to E3. E3 may be joined with E1 (may be defined as, for instance, similar to $R^{38}$) via E2 (may be defined as, for instance, similar to $R^{37}$), or E3 may be joined directly to E1 (e.g. E2 is not present). Similarly, F1 may be joined with F3 (defined as the same as $R^{36}$) via F2 (defined the same as $R^{37}$), or F1 may be joined directly to F3 (e.g. F2 is not present). In this regard, for a biosensor comprising two epitope-binding agent constructs and O, a stable complex capable of producing a signal would require five binding events: the first F3 to the target molecule, the second F3 to the target molecule, the first E1 to A, the second E1 to A, and the first E3 to the first F1, and the second E3 to the second F1.

IV Biosensors Capable of Signal Amplification

Another aspect of the invention encompasses a molecular biosensor capable of signal amplification. Such a biosensor may be used to detect a target molecule. In one embodiment, the biosensor is comprised of two components, which comprise two epitope-binding agent constructs. Alternatively, in another embodiment, the biosensor is comprised of three components, which comprise two epitope-binding agent constructs and an oligonucleotide construct comprising a restriction enzyme recognition site. In each of these embodiments, the epitope-binding agent construct has a modular design.

(a) Two-component Molecular Biosensors

Figure 17A:
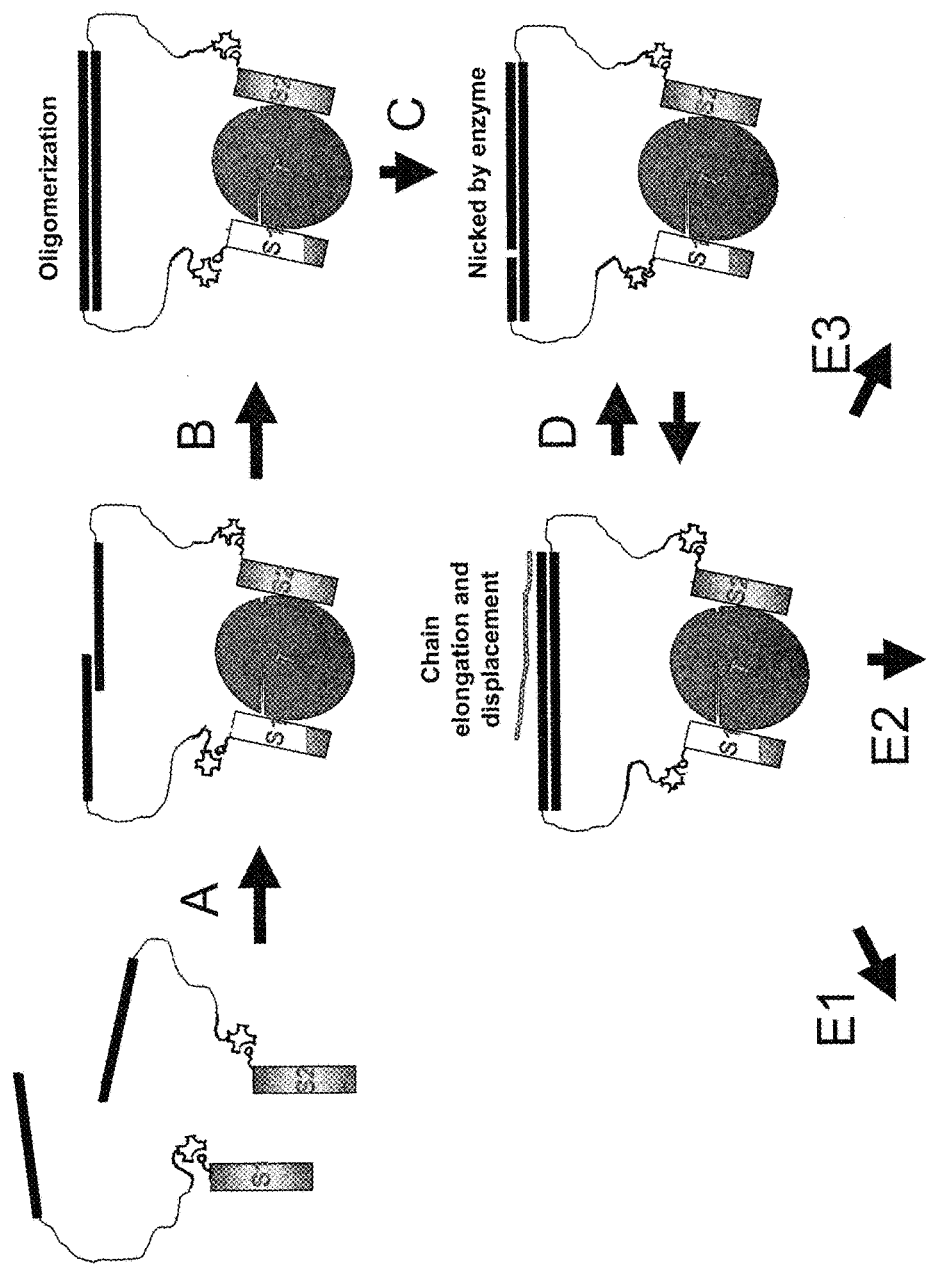
Figure 18:
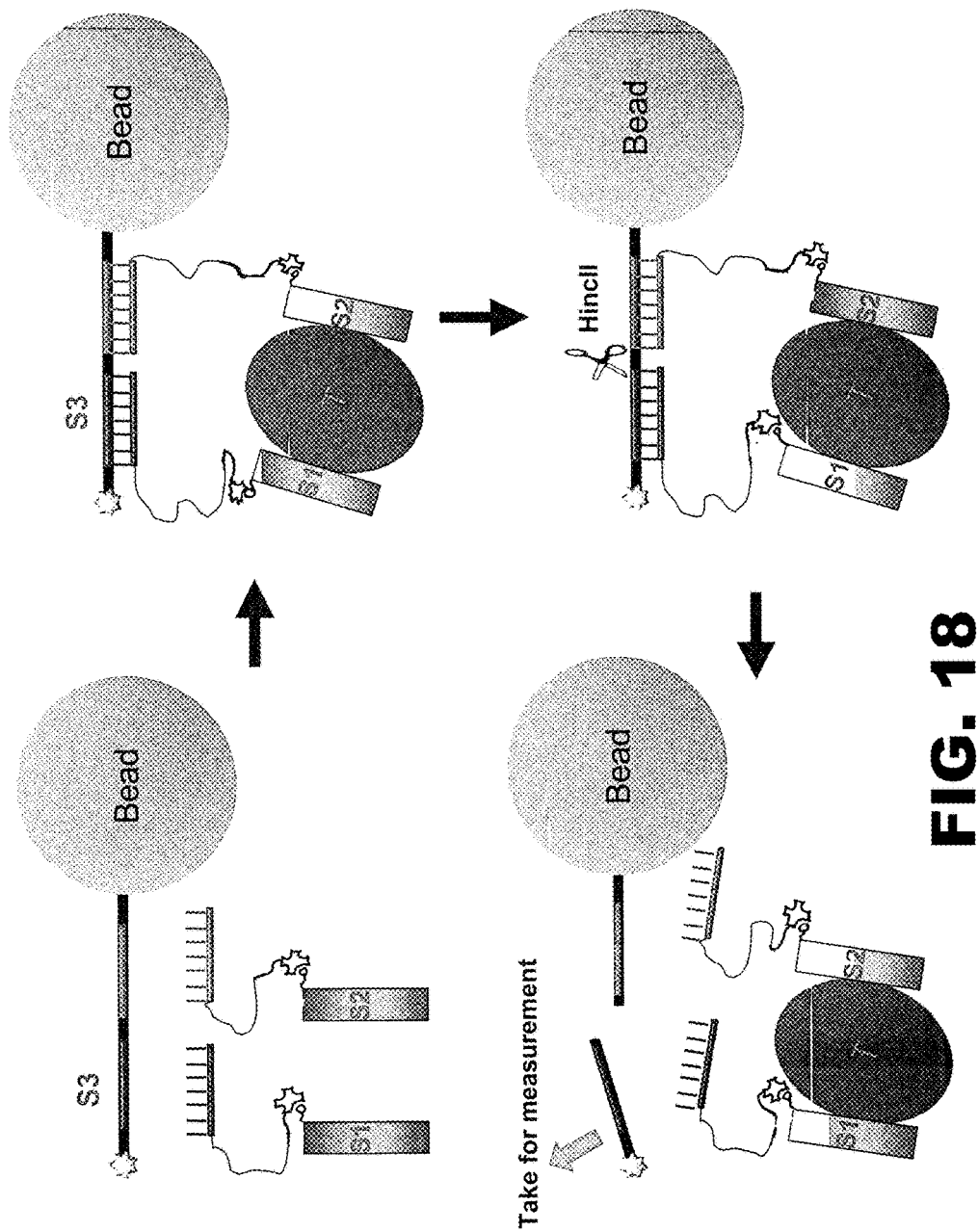
FIG. 18 depicts the overall design and function of a three-component molecular biosensor comprising a signaling oligonucleotide attached to a bead.

One aspect of the invention encompasses a two-component biosensor and methods of use thereof. For a two-component biosensor, detection of a target molecule typically involves target-molecule induced co-association of two epitope-binding agent constructs $((Q^1\text{-}(X^1_{10})_n)\text{—}X^2_{10}\text{-}Q^2\text{-}Q^3$ and $(Q^4\text{-}(X^1_{11})_m)\text{—}X^2_{11}\text{-}Q^5\text{-}Q^6)$ that each recognize distinct epitopes on the target molecule. The epitope-binding agent constructs each comprise a single-stranded nucleotide sequence ($Q^3$ and $Q^6$). Each single-stranded sequence comprises a complementary sequence ($Q^8$ and $Q^9$). Additionally, at least one single-stranded sequence comprises a restriction endonuclease recognition site ($Q^7$). Association of the epitope binding agents ($Q^1$ and $Q^4$) with a target molecule results in annealing of the complementary sequences ($Q^8$ and $Q^9$) of the single-stranded nucleotide sequences, such that when the complementary regions are extended in the presence of a polymerase, a double-stranded endonuclease recognition site is reconstituted. The newly synthesized double-stranded recognition sequence may be nicked by a nicking restriction endonuclease that recognizes the reconstituted restriction enzyme recognition site. A DNA polymerase may then extend a second nucleic acid from the nick, thereby displacing the first nicked strand to form a displaced strand. The second extended strand may then be nicked, repeating the extension and displacement steps such that multiple copies of the displaced strand are produced, thereby amplifying the signal from the biosensor. The displaced strand may then be detected via several different methods. See, for instance FIG. 17.

The structure of the biosensor and methods of using the biosensor are discussed in more detail below.

i. Biosensor Structure

In exemplary embodiments, a two-component molecular biosensor capable of signal amplification comprises two constructs, which together have formula (XI):

$(Q^1\text{-}(X^1_{10})_n)\text{—}X^2_{10}\text{-}Q^2\text{-}Q^3$; and $(Q^4\text{-}(X^1_{11})_m)\text{—}X^2_{11}\text{-}Q^5\text{-}Q^6$;     (XI)

wherein:

$X^1_{10}$ and $X^2_{10}$ are a first affinity binding pair;

$X^1_{11}$ and $X^2_{11}$ are a second affinity binding pair;

n and m are each an integer from 1 to 2;

$Q^1$ is an epitope-binding agent that binds to a first epitope on a target molecule;

$Q^2$ is a flexible linker attaching $X^2_{10}$ to $Q^3$;

$Q^3$ is a single stranded nucleotide sequence comprising $Q^7$ and $Q^8$;

$Q^7$ is a nucleotide sequence comprising at least one restriction endonuclease recognition site;

$Q^8$ is a nucleotide sequence complementary to $Q^9$;

$Q^6$ is a single stranded nucleotide sequence comprising $Q^9$;

$Q^9$ is a nucleotide sequence complementary to $Q^8$, such that when $Q^8$ and $Q^9$ associate to form an annealed complex in the presence of a polymerase, $Q^8$ and $Q^9$ are extended by the polymerase to form a nucleotide sequence complementary to $Q^7$, forming at least one double-stranded endonuclease recognition site;

$Q^5$ is a flexible linker attaching $X^2_{11}$ to $Q^6$;

$Q^4$ is an epitope-binding agent that binds to a second epitope on a target molecule.

As will be appreciated by those of skill in the art, the choice of epitope binding agents, $Q^1$ and $Q^4$, in molecular biosensors having formula (XI) can and will vary depending upon the particular target molecule. By way of example, when the target molecule is a protein, peptide or antigen, $Q^1$ and $Q^4$ may be an aptamer, or antibody. By way of further example, when the target molecule is an antibody, $Q^1$ and $Q^4$ may be an antigen or peptide specifically recognized by the variable region of a target antibody. In still another example, when $Q^1$ and $Q^4$ are double stranded nucleic acid the target molecule is typically a macromolecule that binds to DNA or a DNA binding protein. In an aspect, $Q^1$ and $Q^4$ may be two epitope binding agents that each recognize distinct epitopes on the same target molecule. In another aspect, $Q^1$ and $Q^4$ may be two epitope binding agents that each recognize distinct epitopes on different target molecules. In still another aspect, $Q^1$ and $Q^4$ may be two epitope binding agents that each recognize a repeating epitope on the same target molecule. It is contemplated herein that $Q^1$ and $Q^4$ may or may not be the same epitope binding agent. For example, $Q^1$ and $Q^4$ may be independently selected from a group of suitable epitope binding agents. Non-limiting examples of suitable epitope binding agents may include agents selected from the group consisting of an aptamer, an antibody, an antibody fragment, an antigen, a double-stranded DNA sequence, modified nucleic acids, nucleic acid mimics (e.g. LNA or PNA), a ligand, a ligand fragment, a receptor, a receptor fragment, a protein, a polypeptide, a peptide, a coenzyme, a coregulator, an allosteric molecule, a chemical entity and an ion.

In one embodiment, $Q^1$ and $Q^4$ are each aptamers having a sequence ranging in length from about 20 to about 110 bases. In another embodiment, $Q^1$ and $Q^4$ are each antibodies or antibody-like binders selected from the group consisting of polyclonal antibodies, ascites, Fab fragments, Fab' fragments, monoclonal antibodies, humanized antibodies, chimeric antibodies, single chain antibodies, and non-immunoglobulin scaffolds such as Affibodies, Anticalins, designed Ankyrin repeat proteins and others. In an alternative embodiment, $Q^1$ and $Q^4$ are peptides or antigens. For example, $Q^1$ and $Q^4$ may be peptides or antigens specifically recognized by the variable region of an antibody. By way of non-limiting example, $Q^1$ and $Q^4$ may be peptides or antigens specifically recognized by the variable region of a disease or disorder specific antibody. In an exemplary embodiment, $Q^1$ and $Q^4$ are each monoclonal antibodies. In an additional embodiment, $Q^1$ and $Q^4$ are each double stranded DNA. In a further embodiment, $Q^1$ is a double stranded nucleic acid and $Q^4$ is an aptamer. In an additional embodiment, $Q^1$ is an antibody and $Q^4$ is an aptamer. In another additional embodiment, $Q^1$ is an antibody and $Q^4$ is a double stranded DNA.

In another aspect of a molecular biosensor having formula (XI), an affinity binding pair ($X^1_{10}/X^2_{10}$; $X^1_{11}/X^2_{11}$) non-covalently binds each epitope binding agent, $Q^1$ and $Q^4$, to a signaling oligonucleotide, $Q^3$ and $Q^6$, respectively, through a flexible linker, $Q^2$ and $Q^5$, respectively. In some embodiments, the affinity binding pair in each epitope-binding construct is the same. For example, the first and second affinity binding pair may each consist of biotin and a biotin binding partner. In other embodiments, the affinity bind pair in each epitope-binding construct is different. For example, the first affinity binding pair may consist of biotin and a biotin binding partner, and the second affinity binding pair may consist of an anti-tag antibody and a tag protein. Suitable affinity binding pairs are described above in Section I. Generally speaking, the member of the affinity binding pair that is smaller in size is attached to the epitope binding agent in order to minimize steric interference of the epitope binding agent—target molecule interaction. By way of non-limiting example, biotin is preferably attached to the epitope binding agent when the affinity binding pair consists of biotin and a biotin binding partner.

In another aspect of a molecular biosensor having formula (XI), exemplary linkers, $Q^2$ and $Q^5$, will functionally keep $Q^3$ and $Q^6$ in close proximity such that when $Q^1$ and $Q^4$ each bind to the target molecule, $Q^8$ and $Q^9$ associate in a manner such that a detectable signal is produced. $Q^2$ and $Q^5$ may each be a nucleotide sequence from about 10 to about 100 nucleotides in length. In one embodiment, $Q^2$ and $Q^5$ are from 10 to about 25 nucleotides in length. In another embodiment, $Q^2$ and $Q^5$ are from about 25 to about 50 nucleotides in length. In a further embodiment, $Q^2$ and $Q^5$ are from about 50 to about 75 nucleotides in length. In yet another embodiment, $Q^2$ and $Q^5$ are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment $Q^2$ and $Q^5$ are comprised of DNA bases. In another embodiment, $Q^2$ and $Q^5$ are comprised of RNA bases. In yet another embodiment, $Q^2$ and $Q^5$ are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases may include 2'-fluoro nucleotides, 2'-amino nucleotides, 5'-aminoallyl-2'-fluoro nucleotides and phosphorothioate nucleotides (monothiophosphate and dithiophosphate). In a further embodiment, $Q^2$ and $Q^5$ may be nucleotide mimics. Examples of nucleotide mimics may include locked nucleic acids (LNA), peptide nucleic acids (PNA), and phosphorodiamidate morpholine oligomers (PMO). A nucleotide linker may be single-stranded, double-stranded, or a combination thereof. Alternatively, $Q^2$ and $Q^5$ may be a bifunctional chemical linker or a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP(N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Non-limiting examples of additional suitable linkers include polyethylene glycol such as PEG 4, PEG 8, PEG 12 (a 12-unit polyethylene glycol spacer) and the phosphoramidate form of Spacer 18 comprised of polyethylene glycol, as well as those illustrated in the Examples. In one embodiment, $Q^2$ and $Q^5$ are comprised of nucleotides and a bifunctional chemical linker. In another embodiment, $Q^2$ and $Q^5$ are comprised of a heterobifunctional chemical linker and nucleotides. In still another embodiment, $Q^2$ and $Q^5$ are comprised of a heterobifunctional chemical linker, a polyethylene glycol linker, and nucleotides. In a specific embodiment, $Q^2$ and $Q^5$ are comprised of a SMCC linker and nucleotides. In another specific embodiment, $Q^2$ and $Q^5$ are comprised of a SMCC linker, a polyethylene glycol linker and nucleotides. In one embodiment, $Q^2$ and $Q^5$ are from 0 to about 500 angstroms in length. In another embodiment, $Q^2$ and $Q^5$ are from about 20 to about 400 angstroms in length. In yet another embodiment, $Q^2$ and $Q^5$ are from about 50 to about 250 angstroms in length.

In another aspect of a molecular biosensor having formula (XI), $Q^3$ comprises $Q^7$ and $Q^8$, and $Q^6$ comprises $Q^9$. Generally speaking, except for $Q^8$ and $Q^9$, $Q^3$ and $Q^6$ are not complementary. Further, generally speaking, $Q^3$ and $Q^6$ are not complementary to $Q^2$ and $Q^5$. $Q^8$ and $Q^9$ are nucleotide sequences that are complementary to each other such that they preferably do not associate unless $Q^1$ and $Q^4$ bind to separate epitopes on a target molecule. When $Q^1$ and $Q^4$ bind to separate epitopes of a target molecule, $Q^8$ and $Q^9$ are brought into relative proximity resulting in an increase in their local concentration, which drives the association of $Q^8$ and $Q^9$.

To ensure that $Q^8$ and $Q^9$ only associate when $Q^1$ and $Q^4$ bind to separate epitopes of a target, $Q^8$ and $Q^9$ generally have a length such that the free energy of association is from about −5 to about −12 kcal/mole at a temperature from about 21° C. to about 40° C. and at a salt concentration from about 1 mM to about 100 mM. In other embodiments, the free energy of association between $Q^8$ and $Q^9$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $Q^8$ and $Q^9$ may range from about 4 to about 20 nucleotides in length. In other embodiments, $Q^8$ and $Q^9$ may be about 4, about 5, about 6, about 7, about 8, about 9, about 10, about 11, about 12, about 13, about 14, about 15, about 16, about 17, about 18, about 19, or greater than about 10 nucleotides in length.

In some embodiments, $Q^3$ comprises $Q^7$-$Q^8$, such that $Q^7$ is located 5' to $Q^8$. In other embodiments, $Q^3$ comprises $Q^8$-$Q^7$, such that $Q^8$ is located 5' to $Q^7$.

In an exemplary embodiment, $Q^8$ and $Q^9$ are at the 3' ends of $Q^3$ and $Q^6$, such that association of $Q^8$ and $Q^9$ forms a complex where the 3' ends can be extended using $Q^3$ and $Q^6$ as a template to form a double-stranded nucleotide sequence comprising $Q^7$. Polymerases suitable for extending $Q^8$ and $Q^9$ are known in the art. For example, non-limiting examples of nucleotide polymerases suitable for extending nucleic acid sequences of the invention may include Bsu DNA Polymerase, DNA Polymerase I (*E. coli*), DNA Polymerase I Large (Klenow) Fragment, Klenow Fragment (3'→5 exo-), phi29 DNA Polymerase, T4 DNA Polymerase, T7 DNA Polymerase (unmodified), or any of the thermophilic polymerases, such as the full length or large fragment of Bst DNA Polymerase, Taq DNA Polymerase, 9° $N_m$ DNA Polymerase, Crimson Taq DNA Polymerase, Deep VentR™ (exo-) DNA Polymerase, Deep VentR™ DNA Polymerase, DyNAzyme™ EXT DNA Polymerase, DyNAzyme™ II Hot Start DNA Polymerase, Hemo KlenTaq™, Phusion® High-Fidelity DNA Polymerase, Sulfolobus DNA Polymerase IV, Terminator™ DNA Polymerase, VentR® DNA Polymerase.

Generally speaking, for molecular biosensors having formula (XI) $Q^3$ comprises at least one restriction endonuclease recognition site. In some embodiments, however, $Q^3$ may comprise more than one restriction endonuclease recognition site. For instance, $Q^3$ may comprise at least two, three, four, or five endonuclease recognition sites. Similarly, $Q^6$ may comprise at least one, two, three, four or five endonuclease recognition sites.

Typically, a restriction enzyme recognizing a restriction enzyme recognition site cannot cleave or nick a single stranded nucleotide sequence. Association of the epitope binding agents with a target molecule and the subsequent extension of the 3' ends of $Q^8$ and $Q^9$ in the presence of a polymerase forms a double-stranded endonuclease recognition site that may be cleaved or nicked by a restriction endonuclease. As is commonly known by persons skilled in the art, restriction endonucleases may hydrolyze both strands of the nucleic acid duplex to cleave the nucleic acid duplex, or hydrolyze one of the strands of the nucleic acid duplex, thus producing double-stranded nucleic acid molecules that are "nicked", rather than cleaved. In preferred embodiments of molecular biosensors having formula (XI), $Q^7$ comprises an endonuclease recognition sequence for a nicking restriction enzyme. A nicking restriction endonuclease may hydrolyze the bottom or the top strand of a nucleic acid duplex. By way of non-limiting example, recognition sites for nicking restriction enzymes may include Nt.BstNBI, Nb.BsrD, Nb.BtsI, Nt.AlwI, Nb.BbvCI, Nt.BbvC and Nb.BsmI.

In each of the foregoing embodiments for molecular biosensors having formula (XI), the first nucleic acid construct, $(Q^1\text{-}(X^1_{10})_n)\text{—}X^2_{10}\text{-}Q^2\text{-}Q^3$ and the second nucleic acid construct, $(Q^4\text{-}(X^1_{11})_m)\text{—}X^2_{11}\text{-}Q^5\text{-}Q^6$, may optionally be attached to each other by a linker $Q^{LA}$ to create tight binding bivalent ligands. Typically, the attachment is by covalent bond formation. Alternatively, the attachment may be by non-covalent bond formation. In one embodiment, $Q^{LA}$ attaches $Q^1$ of the first nucleic acid construct to $Q^4$ of the second nucleic acid construct to form a molecule comprising:

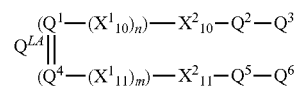

In a further embodiment, $R^{LA}$ attaches $X^1_{10}$ of the first nucleic acid construct to $X^1_{11}$ of the second nucleic acid construct to form a molecule comprising:

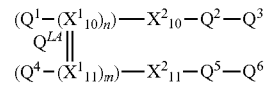

In yet another embodiment, $Q^{LA}$ attaches $X^2_{10}$ of the first nucleic acid construct to $X^2_{11}$ of the second nucleic acid construct to form a molecule comprising:

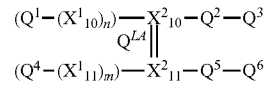

In yet another embodiment, $Q^{LA}$ attaches $Q^2$ of the first nucleic acid construct to $Q^5$ of the second nucleic acid construct to form a molecule comprising:

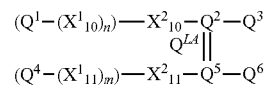

In yet another embodiment, $Q^{LA}$ attaches $Q^3$ of the first nucleic acid construct to $Q^6$ of the second nucleic acid construct to form a molecule comprising:

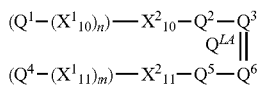

Generally speaking, $Q^{LA}$ may be a nucleotide sequence from about 10 to about 100 nucleotides in length. The nucleotides comprising $Q^{LA}$ may be any of the nucleotide bases in DNA or RNA (A, C, T, G in the case of DNA, or A, C, U, G in the case of RNA). In one embodiment, $Q^{LA}$ is comprised of DNA bases. In another embodiment, $Q^{LA}$ is comprised of RNA bases. In yet another embodiment, $Q^{LA}$ is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases may include 2'-fluoro nucleotides, 2'-amino nucleotides, 5'-aminoallyl-2'-fluoro nucleotides and phosphorothioate nucleotides (monothiophosphate and dithiophosphate). In a further embodiment, $Q^{LA}$ is comprised of nucleotide mimics. Examples of nucleotide mimics may include locked nucleic acids (LNA), peptide nucleic acids (PNA), and phosphorodiamidate morpholine oligomers (PMO). Alternatively, $Q^{LA}$ may be a bifunctional chemical linker or a polymer of bifunctional chemical linkers. In one embodiment the bifunctional chemical linker is heterobifunctional. Suitable heterobifunctional chemical linkers may include sulfoS-MCC (Sulfosuccinimidyl-4-(N-maleimidomethyl)cyclohexane-1-carboxylate), and Ic-SPDP (N-Succinimidyl-6-(3'-(2-PyridylDithio)-Propionamido)-hexanoate). In another embodiment, the bifunctional chemical linker is homobifunctional. Suitable homobifunctional linkers may include disuccinimidyl suberate, disuccinimidyl glutarate, and disuccinimidyl tartrate. Non-limiting examples of additional suitable linkers include polyethylene glycol such as PEG 4, PEG 8, PEG 12 (a 12-unit polyethylene glycol spacer) and the phosphoramidate form of Spacer 18 comprised of polyethylene glycol. In one embodiment, $Q^{LA}$ is from about 1 to about 500 angstroms in length. In another embodiment, $Q^{LA}$ is from about 20 to about 400 angstroms in length. In yet another embodiment, $Q^{LA}$ is from about 50 to about 250 angstroms in length.

ii. Means of Detection

As discussed above, when $Q^8$ and $Q^9$ are extended in the presence of a polymerase, the newly synthesized double-stranded endonuclease recognition sequence may be nicked by a nicking restriction endonuclease that recognizes the double-stranded restriction enzyme recognition site. A DNA polymerase may then extend a second nucleic acid from the nick, thereby displacing the first nicked strand to form a displaced strand. The second extended strand may then be nicked, repeating the extension and displacement steps such that multiple copies of the displaced strand are produced, thereby amplifying the signal from the biosensor. The displaced strand may then be detected via several different methods. Three such methods are detailed below.

In some embodiments, a displaced strand may be detected and/or quantitated by contacting a displaced strand with a complementary nucleic acid sequence. The resulting double-stranded nucleotide sequence may be detected using nucleic acid staining methods specific for double-stranded sequences. Non-limiting examples of nucleic acid stains that may be used for detecting double-stranded nucleotide sequences may include ethidium bromide, thiazole orange, propidium iodide, DAPI, Hoechst dyes, acridine orange, 7-AAD, LDS 751, hydroxystilbamidine, and cyanine dyes such as TOTO-1, POPO-1, BOBO-1, YOYO-1, JOJO-1, LOLO-1, POPO-3, YOYO-3, TOTO-3, BOBO-3, PicoGreen, SYBR Gold, SYBR Green I and SYBR Green II. (See FIG. 17 E1)

In another embodiment, a displaced strand may be detected and/or quantitated by associating with a Type IIS endonuclease nucleic acid construct. The nucleic acid construct may generally comprise two strands, where the first strand comprises $Q^{10}$-$Q^{12}$-$Q^{14}$ and the second strand comprises $Q^{11}$-$Q^{13}$. $Q^{14}$ is complementary to the displaced strand, and when associated with a displaced strand, comprises a Type IIS endonuclease recognition site. $Q^{12}$ is complementary to $Q^{13}$, and together, $Q^{12}$ and $Q^{13}$ comprise a cleavage site for a Type IIS endonuclease. $Q^{12}$ and $Q^{13}$ are of such a length that the two strands (i.e. $Q^{10}$-$Q^{12}$-$Q^{14}$ and $Q^{11}$-$Q^{13}$) stay hybridized in the absence of the displaced strand. $Q^{10}$ and $Q^{11}$ comprise a detection means, such that when $Q^{12}$ and $Q^{13}$ are cleaved by a Type IIS endonuclease, $Q^{10}$ and $Q^{11}$ are released from the Type IIS endonuclease construct and produce a detectable signal. Suitable detection means for $Q^{10}$ and $Q^{11}$ may comprise fluorescent resonance energy transfer (FRET), time resolved-FRET, fluorescence life-time imaging, lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, residence time changes, and redox potential changes. (See FIG. 17 E2)

In some embodiments, a displaced strand may be detected by a linker construct. Usually, a linker construct comprises $Q^{15}$-$Q^{16}$-$Q^{17}$-$Q^{18}$-$Q^{19}$-$Q^{20}$-$Q^{21}$. $Q^{18}$ is a nucleotide sequence that is complementary to the displaced strand, and together with the displaced strand, comprises an endonuclease recognition site. $Q^{17}$ and $Q^{19}$ are linkers, and may be defined as $Q^2$ and $Q^5$ above. $Q^{16}$ and $Q^{20}$ are complementary nucleic acid sequences, and may be defined as $Q^8$ and $Q^9$ above. $Q^{15}$ and $Q^{21}$ comprise a detection means, and may be defined as $Q^{10}$ and $Q^{11}$ above (see FIG. 17 E3). When $Q^{18}$ binds to a displaced strand, a double-stranded restriction endonuclease recognition site is formed. In the presence of a restriction endonuclease, $Q^{18}$ and the displaced strand are cleaved at the endonuclease recognition site. This destabilizes the association of $Q^{16}$ and $Q^{20}$, resulting in the separation of $Q^{15}$ and $Q^{21}$. This separation results in a detectable and quantifiable change in signal intensity.

(b) Three-component Molecular Biosensors

Another aspect of the invention encompasses a three-component biosensor capable of signal amplification. In a three-component embodiment, analogous to a two-component sensor, detection of a target molecule typically involves target-molecule induced co-association of two epitope-binding agent constructs that each recognize distinct epitopes on the target molecule. In each of these embodiments, the epitope-binding agent construct has a modular design. Unlike the two-component embodiment, however, the epitope-binding agent constructs each comprise single stranded nucleic acid sequences that are complementary to two distinct regions of the oligonucleotide construct, as opposed to being complementary to each other (as in the two-component sensor). Co-association of the two epitope-binding agent constructs with a target molecule results in hybridization of each single stranded nucleic acid sequence to the oligonucleotide construct. This tripartite construct comprised of the two single-stranded, epitope-binding agent constructs and the oligonucleotide construct reconstitutes a restriction endonuclease recognition site. The endonuclease recognition site may be cleaved in the presence of a restriction endonuclease. Such cleavage destabilizes the association of the single stranded nucleic acid sequences and the (now cleaved) oligonucleotide construct, releasing the single stranded nucleic acid sequences. The single stranded nucleic acid sequences may then bind to another oligonucleotide construct, repeating the cleavage cycle and therefore amplifying the biosensor signal. Importantly, the oligonucleotide construct is capable of producing a detectable signal when cleaved.

In certain embodiments, the three-component molecular biosensor will comprise a solid support. In alternative embodiments, the three-component molecular biosensor will not comprise a solid support. Both of these embodiments are discussed in more detail below. In some embodiments, a three-component molecular biosensor may comprise a plurality of oligonucleotide constructs (e.g. $Q^7$-$Q^8$ or $Q^7$-$Q^8$-$Q^9$).

i. Three-component Molecular Biosensors Comprising a Solid Support

In one embodiment, a three-component molecular biosensor will comprise an oligonucleotide construct attached to a solid support. Generally speaking, co-association of the two epitope-binding agent constructs with a target molecule results in hybridization of each single stranded nucleic acid sequence to the oligonucleotide construct, producing a tripartite double-stranded nucleic acid molecule that contains a restriction endonuclease recognition site. In the presence of a restriction endonuclease, the oligonucleotide construct may be cleaved to release a signaling molecule from the solid support. (See, for instance, FIG. 18)

For example, in some embodiments the three-component molecular biosensor comprises at least three constructs, which together have formula (XII):

$$(Q^1\text{-}(X^1{}_{12})_n)\text{—}X^2{}_{12}\text{-}Q^2\text{-}Q^3;$$

$$(Q^1\text{-}(X^1{}_{13})_n)\text{—}X^2{}_{13}\text{-}Q^5\text{-}Q^6;\ \text{and}$$

$$\text{at least one } Q^7\text{-}Q^8\text{-}Q^9; \qquad \text{(XII)}$$

wherein:

- $X^1{}_{12}$ and $X^2{}_{12}$ are a first affinity binding pair;
- $X^1{}_{13}$ and $X^2{}_{13}$ are a second affinity binding pair;
- n and m are each an integer from 1 to 2;
- $Q^1$ is an epitope-binding agent that binds to a first epitope on a target molecule;
- $Q^2$ is a flexible linker attaching $X^2{}_{12}$ to $Q^3$;
- $Q^3$ and $R^6$ are a first pair of nucleotide sequences that are complementary to two distinct regions on $Q^8$;
- $Q^5$ is a flexible linker attaching $X^2{}_{13}$ to $Q^6$;
- $Q^4$ is an epitope-binding agent that binds to a second epitope on a target molecule;
- $Q^8$ is a nucleotide construct comprising a first region that is complementary to $Q^3$ and a second region that is complementary to $Q^6$, such that when $Q^3$ and $Q^6$ associated with $Q^8$, an endonuclease restriction site is reconstituted;
- $Q^7$ is a signaling molecule; and
- $Q^9$ is a solid support.

The choice of epitope binding agents, $Q^1$ and $Q^4$, in molecular biosensors having formula (XII) can and will vary depending upon the particular target molecule. By way of example, when the target molecule is a protein, peptide or antigen, $Q^1$ and $Q^4$ may be an aptamer or antibody. By way of further example, when the target molecule is an antibody, $Q^1$ and $Q^4$ may be an antigen or peptide specifically recognized by the variable region of a target antibody. In still another example, when $Q^1$ and $Q^4$ are double stranded nucleic acid the target molecule is typically a macromolecule that binds to DNA or a DNA binding protein. In an aspect, $Q^1$ and $Q^4$ may be two epitope binding agents that each recognize distinct epitopes on the same target molecule. In another aspect, $Q^1$ and $Q^4$ may be two epitope binding agents that each recognize distinct epitopes on different target molecules. In still another aspect, $Q^1$ and $Q^4$ may be two epitope binding agents that each recognize a repeating epitope on the same target molecule. It is contemplated herein that $Q^1$ and $Q^4$ may or may not be the same epitope binding agent. For example, $Q^1$ and $Q^4$ may be independently selected from a group of suitable epitope binding agents. Non-limiting examples of suitable epitope binding agents, depending upon the target molecule, may include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a protein, a polypeptide, a peptide, an antigen, a coenzyme, a coregulator, an allosteric molecule, and an ion.

In an exemplary embodiment, $Q^1$ and $Q^4$ are each aptamers having a sequence ranging in length from about 20 to about 110 bases. In another embodiment, $Q^1$ and $Q^4$ are each antibodies selected from the group consisting of polyclonal antibodies, ascites, Fab fragments, Fab' fragments, monoclonal antibodies, humanized antibodies, chimeric antibodies, and single-chain antibodies. In an alternative embodiment, $Q^1$ and $Q^4$ are peptides or antigens. For example, $Q^1$ and $Q^4$ may be peptides or antigens specifically recognized by the variable region of an antibody. By way of non-limiting example, $Q^1$ and $Q^4$ may be peptides or antigens specifically recognized by the variable region of a disease or disorder specific antibody. In a preferred embodiment, $Q^1$ and $Q^4$ are each monoclonal antibodies. In another preferred embodiment, $Q^1$ and $Q^4$ are each peptides or antigens. In an additional embodiment, $Q^1$ and $Q^4$ are each double stranded DNA. In a further embodiment, $Q^1$ is a double stranded nucleic acid and $Q^4$ is all aptamer. In an additional embodiment, $Q^1$ is an antibody and $Q^4$ is an aptamer. In another additional embodiment, $Q^1$ is an antibody and $Q^4$ is a double stranded DNA.

In another aspect of a molecular biosensor having formula (XII), an affinity binding pair ($X^1{}_{12}/X^2{}_{12}$; $X^1{}_{13}/X^2{}_{13}$) non-covalently binds each epitope binding agent, $Q^1$ and $Q^4$, to a signaling oligonucleotide, $Q^3$ and $Q^6$, respectively, through a flexible linker, $Q^2$ and $Q^5$, respectively. In some embodiments, the affinity bind pair in each epitope-binding construct is the same. For example, the first and second affinity binding pair may each consist of biotin and a biotin binding partner. In other embodiments, the affinity bind pair in each epitope-binding construct is different. For example, the first affinity binding pair may consist of biotin and a biotin binding partner, and the second affinity binding pair may consist of anti-tag antibody and tag protein. Suitable affinity binding pairs are described above in Section I. Generally speaking, the member of the affinity binding pair that is smaller in size is attached to the epitope binding agent in order to minimize steric interference of the epitope binding agent-target molecule interaction. By way of non-limiting example, biotin is preferably attached to the epitope binding agent when the affinity binding pair consists of biotin and a biotin binding partner.

In another aspect of a molecular biosensor having formula (XII), exemplary linkers, $Q^2$ and $Q^5$, will functionally keep $Q^3$ and $Q^6$ in appropriate proximity such that when $Q^1$ and $Q^4$ each bind to the target molecule, $Q^3$ and $Q^6$ associate with $R^8$ producing a detectable signal. $Q^2$ and $Q^5$ may each be a nucleotide sequence from about 10 to about 100 nucleotides in length. In one embodiment, $Q^2$ and $Q^5$ are from about 10 to about 25 nucleotides in length. In another embodiment, $Q^2$ and $Q^5$ are from about 25 to about 50 nucleotides in length. In a further embodiment, $Q^2$ and $Q^5$ are from about 50 to about 75 nucleotides in length. In yet another embodiment, $Q^2$ and $Q^5$ are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment $Q^2$ and $Q^5$ are comprised of DNA bases. In another embodiment, $Q^2$ and $Q^5$ are comprised of RNA bases. In yet another embodiment, $Q^2$ and $Q^5$ are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases may include 2'-fluoro nucleotides, 2'-amino nucleotides, 5'-aminoallyl-2'-fluoro nucleotides and phosphorothioate nucleotides (monothiophosphate and dithiophosphate). In a further embodiment, $Q^2$ and $Q^5$ may be nucleotide mimics. Examples of nucleotide mimics may include locked nucleic acids (LNA), peptide nucleic acids (PNA), and phosphorodiamidate morpholine oligomers (PMO). A nucleotide linker may be single-stranded, double-stranded, or a combination thereof. Alternatively, $Q^2$ and $Q^5$ may be a bifunctional chemical linker or a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP(N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Non-limiting examples of additional suitable linkers include polyethylene glycol such as PEG 4, PEG 8, PEG 12 (a 12-unit polyethylene glycol spacer) and the phosphoramidate form of Spacer 18 comprised of polyethylene glycol, as well as those illustrated in the Examples. In one embodiment, $Q^2$ and $Q^5$ are comprised of nucleotides and a bifunctional chemical linker. In another embodiment, $Q^2$ and $Q^5$ are comprised of a heterobifunctional chemical linker and nucleotides. In still another embodiment, $Q^2$ and $Q^5$ are comprised of a heterobifunctional chemical linker, a polyethylene glycol linker, and nucleotides. In a specific embodiment, $Q^2$ and $Q^5$ are comprised of a SMCC linker and nucleotides. In another specific embodiment, $Q^2$ and $Q^5$ are comprised of a SMCC linker, a polyethylene glycol linker and nucleotides. In one embodiment, $Q^2$ and $Q^5$ are from 0 to about 500 angstroms in length. In another embodiment, $Q^2$ and $Q^5$ are from about 20 to about 400 angstroms in length. In yet another embodiment, $Q^2$ and $Q^5$ are from about 50 to about 250 angstroms in length.

In another aspect of a molecular biosensor having formula (XII), $Q^7$ is a signaling molecule. Suitable signaling molecules are known in the art. Non-limiting examples may include luminescent molecules, chemiluminescent molecules, fluorochromes, fluorescent quenching agents, colored molecules, radioisotopes, scintillants, massive labels (for detection via mass changes), biotin, avidin, streptavidin, protein A, protein G, antibodies or fragments thereof, Grb2, polyhistidine, $Ni^{2+}$, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present invention.

In another aspect of a molecular biosensor having formula (XII), $Q^8$ comprises a first region that is complementary to $Q^6$, and a second region that is complementary to $Q^3$. $Q^8$ may be from about 8 to about 100 nucleotides in length. In other embodiments, $Q^8$ is from about 10 to about 15 nucleotides in length, or from about 15 to about 20 nucleotides in length, or from about 20 to about 25 nucleotides in length, or from about 25 to about 30 nucleotides in length, or from about 30 to about 35 nucleotides in length, or from about 35 to about 40 nucleotides in length, or from about 40 to about 45 nucleotides in length, or from about 45 to about 50 nucleotides in length, or from about 50 to about 55 nucleotides in length, or from about 55 to about 60 nucleotides in length, or from about 60 to about 65 nucleotides in length, or from about 65 to about 70 nucleotides in length, or from about 70 to about 75 nucleotides in length, or from about 75 to about 80 nucleotides in length, or from about 80 to about 85 nucleotides in length, or from about 85 to about 90 nucleotides in length, or from about 90 to about 95 nucleotides in length, or greater than about 95 nucleotides in length.

When $Q^3$ and $Q^6$ associate with $Q^8$, a tripartite double-stranded DNA molecule is formed that contains a restriction endonuclease recognition sequence. In the presence of a restriction endonuclease, $Q^8$ is cleaved, releasing $Q^7$ from the solid support $Q^9$. In an exemplary embodiment, $Q^3$ and $Q^6$ do not form a stable complex with $Q^8$ after $Q^8$ is cleaved, freeing $Q^3$ and $Q^6$ to bind to another $Q^8$ and repeat the cleavage cycle. This amplifies the biosensor signal.

In an exemplary embodiment, $Q^8$ will comprise formula (XIII):

$$Q^{22}\text{-}Q^{23}\text{-}Q^{24}\text{-}Q^{25} \qquad (XIII)$$

wherein:

$Q^{22}$ and $Q^{25}$ are single-stranded nucleotide sequences not complementary to any of $Q^1$, $Q^2$, $Q^3$, $Q^4$, $Q^5$, or $Q^6$.

$Q^{23}$ is a nucleotide sequence complementary to $Q^3$; and $Q^{24}$ is a nucleotide sequence that is complementary to $Q^6$.

In some embodiments, $Q^{22}$ and $Q^{25}$ may independently be from about 0 to about 20 nucleotides in length. In other embodiments, $Q^{22}$ and $Q^{25}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length.

Generally speaking, $Q^{23}$ and $Q^{24}$ have a length such that the free energy of association between $Q^{23}$ and $Q^3$ and $Q^{24}$ and $Q^6$ is from about $-5$ to about $-12$ kcal/mole at a temperature from about 21° C. to about 40° C. and at a salt concentration from about 1 mM to about 100 mM. In other embodiments, the free energy of association between $Q^{23}$ and $Q^3$ and $Q^{24}$ and $Q^6$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $Q^{23}$ and $Q^{24}$ may range from about 4 to about 20 nucleotides in length. In other embodiments, $Q^{23}$ and $Q^{24}$ may be about 4, about 5, about 6, about 7, about 8, about 9, about 10, about 11, about 12, about 13, about 14, about 15, about 16, about 17, about 18, about 19, or greater than about 10 nucleotides in length.

In one embodiment, when $Q^8$ comprises formula (XIII), the cleavage site of the restriction endonuclease recognition sequence produced by the association of $Q^3$ and $Q^6$ with $Q^8$ is located between $Q^{23}$ and $Q^{24}$. In this manner, in the presence of a suitable restriction endonuclease, $Q^8$ will be cleaved between $Q^{23}$ and $Q^{24}$, but $Q^3$ and $Q^6$ remain intact. Suitable restriction endonuclease recognition sequences are recognized by restriction enzymes that cleave double stranded nucleic acid, but not single stranded nucleic acid. Such enzymes and the corresponding recognition sites are known in the art. By way of non-limiting example, these enzymes may include AccI, AgeI, BamHI, BglI, BglII, BsiWI, BstBI, ClaI, CviQI, DdeI, DpnI, DraI, EagI, EcoRI, EcoRV, FseI, FspI, HaeII, HaeIII, HhaI, HincII, HinDIII, HpaI, HpaII, KpnI, KspI, MboI, MfeI, NaeI, NarI, NcoI, NdeI, NheI, NotI, PhoI, PstI, PvuI, PvuII, SacI, SacI, SaiI, SbfI, SmaI, SpeI, SphI, StuI, TaqI, TliI, TfiI, XbaI, XhoI, XmaI, XmnI, and ZraI.

In another exemplary embodiment, $Q^8$ will comprise formula (XIV):

$$Q^{26}\text{-}Q^{27}\text{-}Q^{28}\text{-}Q^{29}\text{-}Q^{30}\text{-}Q^{31} \qquad (XIV)$$

wherein:
$Q^{27}$, $Q^{28}$, $Q^{29}$, and $Q^{30}$ are single stranded oligonucleotide sequences not complementary to each other or any of $Q^1$, $Q^2$, $Q^3$, $Q^4$, $Q^5$, or $Q^6$;
$Q^{26}$ and $Q^{31}$ are double-stranded nucleic acid sequences;
$Q^{28}$ is a nucleotide sequence complementary to $Q^3$; and
$Q^{29}$ is a nucleotide sequence that is complementary to $Q^6$.
$Q^{27}$ and $Q^{30}$ may independently be from about 0 to about 20 nucleotides in length. In other embodiments, $Q^{27}$ and $Q^{30}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length;
$Q^{26}$ and $Q^{31}$ may independently be from about 0 to about 20 base pairs in length. In other embodiments, $Q^{26}$ and $Q^{31}$ may independently be from about 2 to about 4 base pairs in length, or from about 4 to about 6 base pairs in length, or from about 6 to about 8 base pairs in length, or from about 8 to about 10 base pairs in length, or from about 10 to about 12 base pairs in length, or from about 12 to about 14 base pairs in length, or from about 14 to about 16 base pairs in length, or from about 16 to about 18 base pairs in length, or from about 18 to about 20 base pairs in length, or greater than about 20 base pairs in length;
$Q^{28}$ and $Q^{29}$ generally have a length such that the free energy of association between $Q^{28}$ and $Q^3$ and $Q^{29}$ and $Q^6$ is from about −5 to about −12 kcal/mole at a temperature from about 21° C. to about 40° C. and at a salt concentration from about 1 mM to about 100 mM. In other embodiments, the free energy of association between $Q^{28}$ and $Q^3$ and $Q^{29}$ and $Q^6$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $Q^{28}$ and $Q^{29}$ may range from about 4 to about 20 nucleotides in length. In other embodiments, $Q^{28}$ and $Q^{29}$ may be about 4, about 5, about 6, about 7, about 8, about 9, about 10, about 11, about 12, about 13, about 14, about 15, about 16, about 17, about 18, about 19, or greater than about 20 nucleotides in length.

In yet another exemplary embodiment, $Q^8$ may comprise formula (XV):

$$Q^{32}\text{-}Q^{33}\text{-}Q^{34}\text{-}Q^{35}\text{-}Q^{36}\text{-}Q^{37}\text{-}Q^{38} \qquad (XV)$$

wherein:
$Q^{33}$, $Q^{34}$, $Q^{36}$, $Q^{37}$ and $Q^{38}$ are single stranded oligonucleotide sequences independently not complementary to each other or any of $Q^1$, $Q^2$, $Q^3$, $Q^4$, $Q^5$, or $Q^6$;
$Q^{32}$ and $Q^{35}$ are double-stranded nucleic acid sequences;
$Q^{33}$ is a nucleotide sequence complementary to $Q^3$; and
$Q^{37}$ is a nucleotide sequence that is complementary to $Q^6$.
$Q^{34}$, $Q^{36}$, and $Q^{38}$ may independently be from about 0 to about 20 nucleotides in length. In other embodiments, $Q^{34}$, $Q^{36}$, and $Q^{38}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length.

$Q^{32}$ and $Q^{35}$ may independently be from about 0 to about 20 base pairs in length. In other embodiments, $Q^{32}$ and $Q^{35}$ may independently be from about 2 to about 4 base pairs in length, or from about 4 to about 6 base pairs in length, or from about 6 to about 8 base pairs in length, or from about 8 to about 10 base pairs in length, or from about 10 to about 12 base pairs in length, or from about 12 to about 14 base pairs in length, or from about 14 to about 16 base pairs in length, or from about 16 to about 18 base pairs in length, or from about 18 to about 20 base pairs in length, or greater than about 20 base pairs in length.

$Q^{33}$ and $Q^{37}$ generally have a length such that the free energy of association between $Q^{33}$ and $Q^3$ and $Q^{37}$ and $Q^6$ is from about −5 to about −12 kcal/mole at a temperature from about 21° C. to about 40° C. and at a salt concentration from about 1 mM to about 100 mM. In other embodiments, the free energy of association between $Q^{33}$ and $Q^3$ and $Q^{37}$ and $Q^6$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $Q^{33}$ and $Q^{37}$ may range from about 4 to about 20 nucleotides in length. In other embodiments, $Q^{33}$ and $Q^{37}$ may be about 4, about 5, about 6, about 7, about 8, about 9, about 10, about 11, about 12, about 13, about 14, about 15, about 16, about 17, about 18, about 19, or greater than about 10 nucleotides in length.

When $Q^8$ comprises formula (XIV) or formula (XV), a cleavage site of a restriction endonuclease recognition sequence produced by the association of $Q^3$ and $Q^6$ with $Q^8$ may be located within $Q^{26}$ for formula (XIV) or within $Q^{32}$ for formula (XV), $Q^{31}$ for formula (XIV), $Q^{35}$ for formula (XV), or a combination thereof. Suitable restriction endonuclease recognition sequences for these embodiments are recognized by restriction enzymes that cleave double stranded nucleic acid outside the recognition sequence of the restriction enzyme. Such enzymes and the corresponding recognition and cleavage sites are known in the art. By way of non-limiting example, these sites may include AcuI, AlwI, BaeI, BbsI, BbvI, BccI, BceAI, BcgI, BciVI, BfuAI, BmrI, BpmI, BpuEI, BsaI, BsaXI, BseRI, BsgI, BsmAI, BsmBI, BsmFI, BspCNI, BspMI, BspQI, BtgZI, CspCI, EarI, EciI, EcoP15I, FokI, HgaI, HphI, HpyAV, MboII, MlyI, MmeI, MmeAIII, PleI, SapI, SfaNI.

In some embodiments for molecular biosensors having formula (XIV) or formula (XV), $Q^7$ may comprise two signaling molecules, each attached to one strand of a double-stranded nucleotide sequence comprising $Q^8$. Cleavage of the restriction enzyme recognition site results in the release and separation of the two signaling molecules, resulting in a detectable and quantifiable change in signal intensity. Exemplary detections means suitable for use in the molecular biosensors include fluorescent resonance energy transfer (FRET), time resolved-FRET, fluorescence life-time imaging, lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, residence time changes, and redox potential changes.

In some embodiments, $Q^9$ is a solid support having $Q^8$ attached thereto. Non-limiting examples of suitable solid supports may include microtitre plates, test tubes, beads, resins and other polymers, as well as other surfaces either known in the art or described herein. The solid support may be a material that may be modified to contain discrete individual sites appropriate for the attachment or association of the construct and is amenable to at least one detection method. Non-limiting examples of solid support materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. The size and shape of the solid support may also vary without departing from the scope of the invention. A solid support may be planar, a solid support may be a well, i.e. a 384 well plate, or alternatively, a solid support may be a bead or a slide.

$Q^8$ may be attached to the $Q^9$ in a wide variety of ways, as will be appreciated by those in the art. $Q^8$, for example, may either be synthesized first, with subsequent attachment to the solid support, or may be directly synthesized on the solid support. $Q^9$ and $Q^8$ may be derivatized with chemical functional groups for subsequent attachment of the two. For example, the solid support may be derivatized with a chemical functional group including, but not limited to, amino groups, carboxyl groups, oxo groups or thiol groups. Using these functional groups, the $Q^8$ may be attached using functional groups either directly or indirectly using linkers. Alternatively, $Q^8$ may also be attached to the surface non-covalently. For example, a biotinylated $Q^8$ can be prepared, which may bind to surfaces covalently coated with streptavidin, resulting in attachment. Alternatively, $Q^8$ may be synthesized on the surface using techniques such as photopolymerization and photolithography. Additional methods of attaching $Q^8$ to a surface and methods of synthesizing nucleic acids on surfaces are well known in the art, i.e. VLSIPS technology from Affymetrix (e.g., see U.S. Pat. No. 6,566,495, and Rockett and Dix, "DNA arrays: technology, options and toxicological applications," Xenobiotica 30(2): 155-177, all of which are hereby incorporated by reference in their entirety).

In each of the foregoing embodiments for molecular biosensors having formula (XII), the first nucleic acid construct, $Q^1$-$Q^2$-$Q^3$ and the second nucleic acid construct, $Q^4$-$Q^5$-$Q^6$, may optionally be attached to each other by a linker $Q^{LA}$ to create tight binding bivalent ligands. Typically, the attachment is by covalent bond formation. Alternatively, the attachment may be by non-covalent bond formation. In one embodiment, $Q^{LA}$ attaches $Q^1$ of the first nucleic acid construct to $Q^4$ of the second nucleic acid construct to form a molecule comprising:

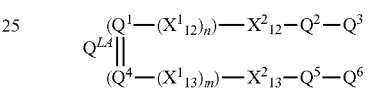

In a further embodiment, $R^{LA}$ attaches $X^1{}_{12}$ of the first nucleic acid construct to $X^1{}_3$ of the second nucleic acid construct to form a molecule comprising:

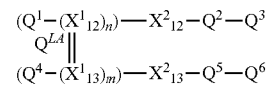

In yet another embodiment, $Q^{LA}$ attaches $X^2{}_{12}$ of the first nucleic acid construct to $X^2{}_{13}$ of the second nucleic acid construct to form a molecule comprising:

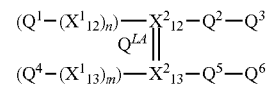

In yet another embodiment, $Q^{LA}$ attaches $Q^2$ of the first nucleic acid construct to $Q^5$ of the second nucleic acid construct to form a molecule comprising:

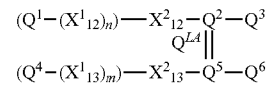

In yet another embodiment, $Q^{LA}$ attaches $Q^3$ of the first nucleic acid construct to $Q^6$ of the second nucleic acid construct to form a molecule comprising:

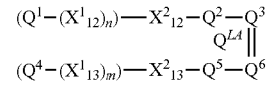

Generally speaking, $Q^{LA}$ may be a nucleotide sequence from about 10 to about 100 nucleotides in length. The nucleotides comprising $Q^{LA}$ may be any of the nucleotide bases in DNA or RNA (A, C, T, G in the case of DNA, or A, C, U, G in the case of RNA). In one embodiment, $Q^{LA}$ is comprised of DNA bases. In another embodiment, $Q^{LA}$ is comprised of RNA bases. In yet another embodiment, $Q^{LA}$ is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $Q^{LA}$ is comprised of nucleotide mimics. Examples of nucleotide mimics include locked nucleic acids (LNA), peptide nucleic acids (PNA), and phosphorodiamidate morpholine oligomers (PMO). Alternatively, $Q^{LA}$ may be a bifunctional chemical linker or a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and lc-SPDP (N-Succinimidyl-6-(3'-(2-PyridylDithio)-Propionamido)-hexanoate). In another embodiment, the bifunctional chemical linker is homobifunctional. Suitable homobifunctional linkers include disuccinimidyl suberate, disuccinimidyl glutarate, and disuccinimidyl tartrate. Non-limiting examples of additional suitable linkers include polyethylene glycol such as PEG 4, PEG 8, PEG 12 (a 12-unit polyethylene glycol spacer) and the phosphoramidate form of Spacer 18 comprised of polyethylene glycol. In one embodiment, $Q^{LA}$ is from about 1 to about 500 angstroms in length. In another embodiment, $Q^{LA}$ is from about 20 to about 400 angstroms in length. In yet another embodiment, $Q^{LA}$ is from about 50 to about 250 angstroms in length.

In an alternative embodiment of the three-component biosensor, the biosensor does not comprise a solid support. For instance, in some embodiments, the three-component molecular biosensor comprises three constructs, which together have formula (XVI):

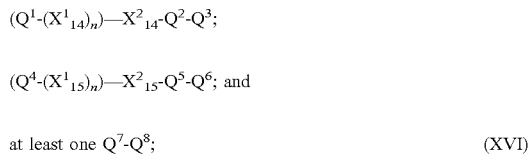

$(Q^1\text{-}(X^1_{14})_n)\text{---}X^2_{14}\text{-}Q^2\text{-}Q^3;$ $(Q^4\text{-}(X^1_{15})_n)\text{---}X^2_{15}\text{-}Q^5\text{-}Q^6;$ and at least one $Q^7\text{-}Q^8;$ (XVI)

wherein:
- $X^1_{14}$ and $X^2_{14}$ are a first affinity binding pair;
- $X^1_{15}$ and $X^2_{15}$ are a second affinity binding pair;
- n and m are each an integer from 1 to 2;
- $Q^1$ is an epitope-binding agent that binds to a first epitope on a target molecule;
- $Q^2$ is a flexible linker attaching $X^2_{14}$ to $Q^3$;
- $Q^3$ and $Q^6$ are a first pair of nucleotide sequences that are complementary to two distinct regions on $Q^8$;
- $Q^5$ is a flexible linker attaching $X^2_{15}$ to $Q^6$;
- $Q^6$ is an epitope-binding agent that binds to a second epitope on a target molecule;
- $Q^8$ is a nucleotide construct comprising a first region that is complementary to $Q^3$ and a second region that is complementary to $Q^6$, such that when $Q^3$ and $Q^6$ associated with $Q^8$, an endonuclease restriction site is reconstituted;
- $Q^7$ is a signaling molecule.

$Q^1$, $Q^2$, $Q^3$, $Q^4$, $Q^5$, $Q^6$, and $Q^7$ may be as defined above for three-component molecular biosensors having formula (XII). $Q^8$ may be as described in Section (IV)(b)(i) above. $X^1_{14}$, $X^2_{14}$, $X^1_{15}$ and $X^2_{15}$ may be as defined above for $X^1_{12}$, $X^2_{12}$, $X^1_{13}$ and $X^2_{13}$.

In some embodiments for molecular biosensors having Formula (XVI), $Q^7$ may comprise two signaling molecules, each attached to one strand of a double-stranded nucleotide sequence comprising $Q^8$. Cleavage of the restriction enzyme recognition site results in the release and separation of the two signaling molecules, resulting in a detectable and quantifiable change in signal intensity. Exemplary detections means suitable for use in the molecular biosensors include fluorescent resonance energy transfer (FRET), time resolved-FRET, fluorescence life-time imaging, lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, residence time changes, and redox potential changes.

V Methods for Selecting Epitope Binding Agents

A further aspect of the invention provides methods for selecting epitope-binding agents, and in particular aptamers for use in making any of the molecular biosensors of the present invention. Generally speaking, epitope binding agents comprising aptamers, antibodies, peptides, modified nucleic acids, nucleic acid mimics, or double stranded DNA may be purchased if commercially available or may be made in accordance with methods generally known in the art.

For example, in vitro methods of selecting peptide epitope binding agents include phage display (Ozawa et al., J. Vet. Med. Sci. 67(12):1237-41, 2005), yeast display (Boder et al., Nat. Biotech. 15:553-57, 1997), ribosome display (Hanes et al., PNAS 94:4937-42, 1997; Lipovsek et al., J. Imm. Methods, 290:51-67, 2004), bacterial display (Francisco et al., PNAS 90:10444-48, 1993; Georgiou et al., Nat. Biotech. 15:29-34, 1997), mRNA display (Roberts et al., PNAS 94:12297-302, 1997; Keefe et al., Nature 410:715-18, 2001), and protein scaffold libraries (Hosse et al., Protein Science 15:14-27, 2006). In one embodiment, the peptide epitope binding agents are selected by phage display. In another embodiment, the peptide epitope binding agents are selected by yeast display. In yet another embodiment, the peptide epitope binding agents are selected via ribosome display. In still yet another embodiment, the peptide epitope binding agents are selected via bacterial display. In an alternative embodiment, the peptide epitope binding agents are selected by mRNA display. In another alternative embodiment, the peptide epitope binding agents are selected using protein scaffold libraries.

The invention, however, provides methods for simultaneously selecting two or more aptamers that each recognize distinct epitopes on a target molecule or on separate target molecules. Alternatively, the invention also provides novel methods directed to selecting at least one aptamer in the presence of an epitope-binding agent construct. The aptamer and epitope-binding agent construct also each recognize distinct epitopes on a target molecule.

VI Methods Utilizing the Molecular Biosensors

A further aspect of the invention encompasses the use of the molecular biosensors of the invention in several applications. In certain embodiments, the molecular biosensors are utilized in methods for detecting one or more target molecules. In other embodiments, the molecular biosensors may be utilized in kits and for therapeutic and diagnostic applications.

(a) Detection Methods

In one embodiment, the molecular biosensors may be utilized for detection of a target molecule. The method generally involves contacting a molecular biosensor of the invention with the target molecule. To detect a target molecule utilizing two-component biosensors, the method typically involves target-molecule induced co-association of two epitope-binding agents (present in the molecular biosensor of the invention) that each recognize distinct epitopes on the target molecule. The epitope-binding agents each comprise complementary signaling oligonucleotides that are labeled with detection means and are attached to the epitope-binding agents through a flexible linker. Co-association of the two epitope-binding agents with the target molecule results in bringing the two signaling oligonucleotides into proximity such that a detectable signal is produced. Typically, the detectable signal is produced by any of the detection means known in the art or as described herein. Alternatively, for three-component biosensors, co-association of the two epitope-binding agent constructs with the target molecule results in hybridization of each signaling oligos to the oligonucleotide construct. Binding of the two signaling oligo to the oligonucleotide construct brings them into proximity such that a detectable signal is produced.

Figure 13A:
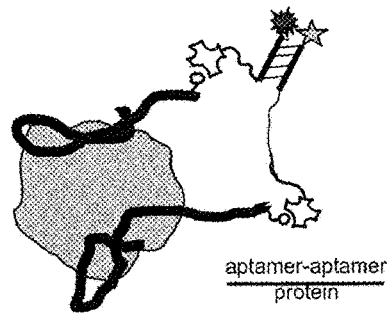
FIG. 13A, FIG. 13B, FIG. 13C, FIG. 13D, FIG. 13E, FIG. 13F, FIG. 13G, FIG. 13H and FIG. 13I depict various formations of molecular biosensors.
Figure 13B:
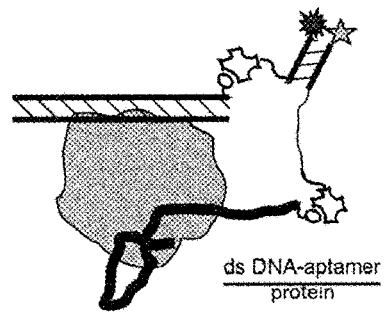
Figure 13C:
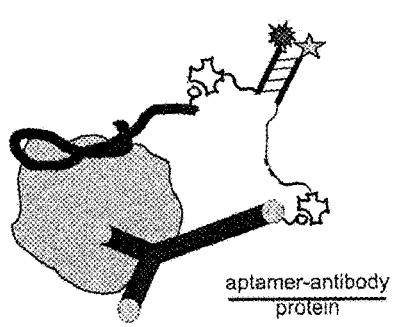
Figure 13D:
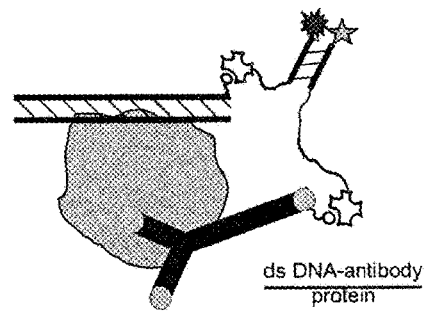
Figure 13E:
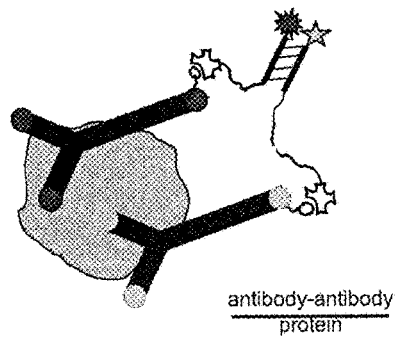
Figure 13F:
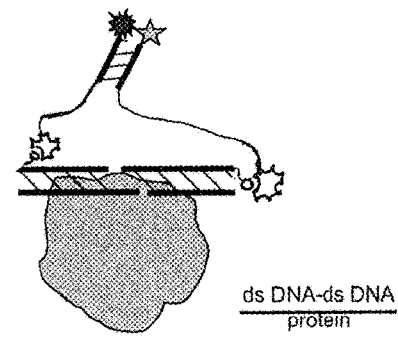
Figure 13G:
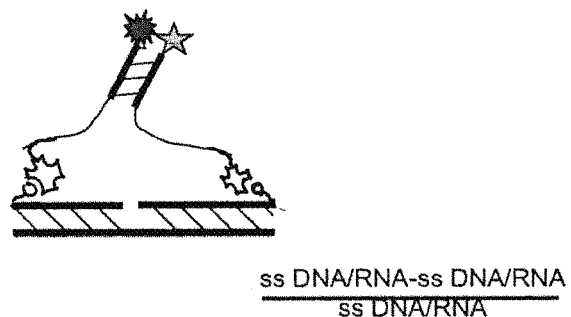
Figure 13H:
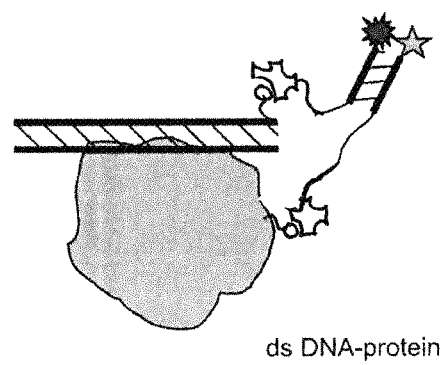
Figure 13I:
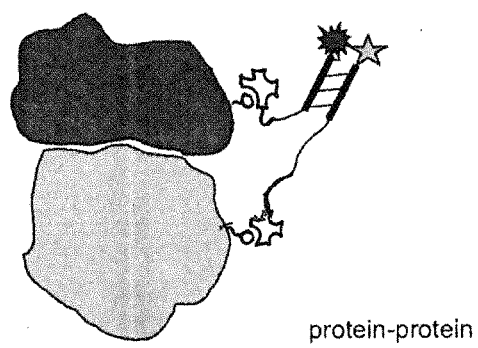
Figure 14:
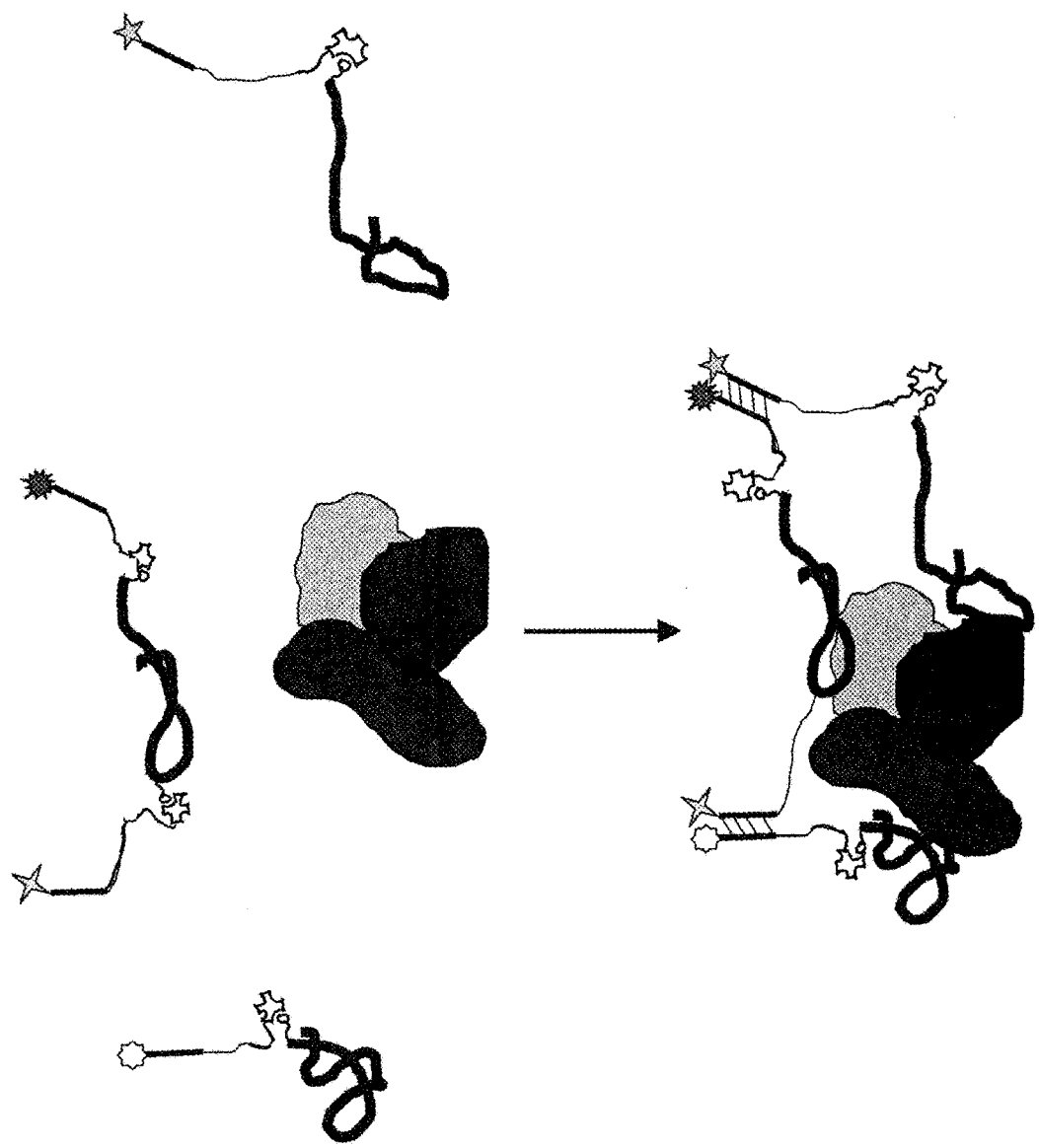
FIG. 14 depicts an example of a potential sensor design utilizing three sensing components. In this design the target is a complex of three components (black, dark gray, and light gray ovals). Each of the aptamers recognizes one of the components of the complex. Signals of different color from each of the two signaling oligonucleotide pairs could be used to discriminate between the entire complex containing all three components with alternative sub-complexes containing only two of the components.
Figure 15A:
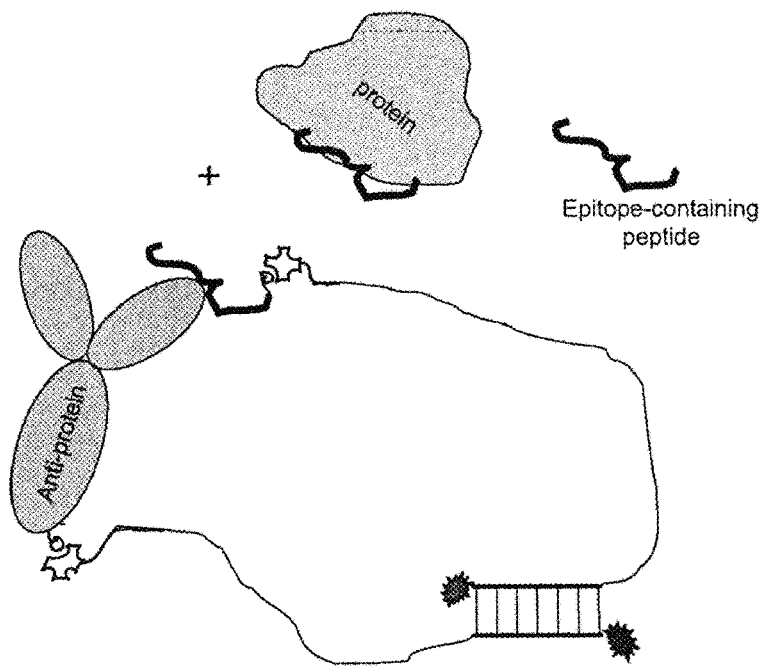
FIG. 15A and FIG. 15B depict a competition assay.
Figure 15B:
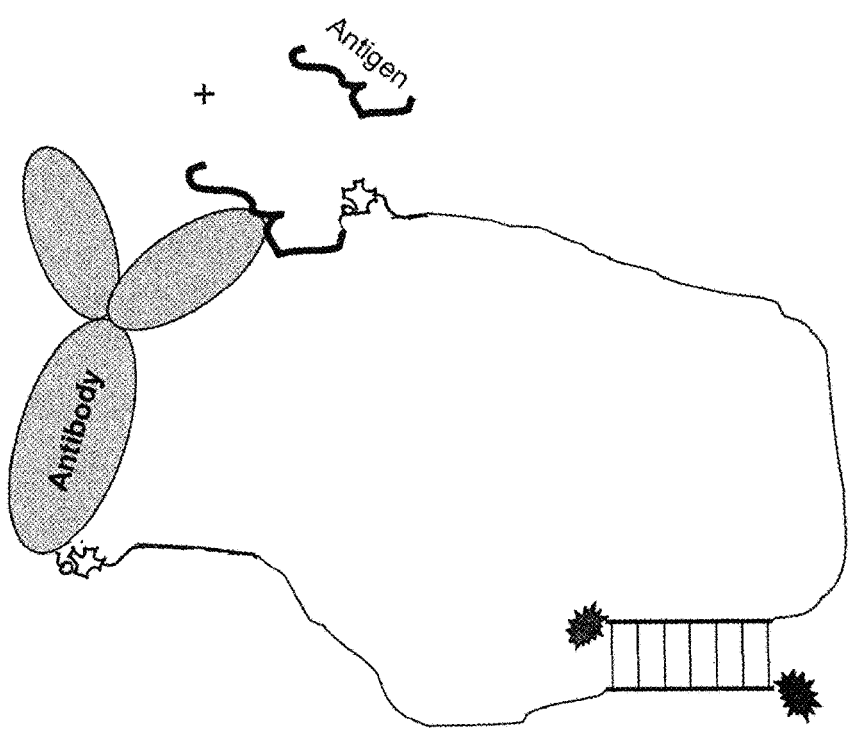

In one particular embodiment, a method for the detection of a target molecule that is a protein or polypeptide is provided. In a specific embodiment, the protein or polypeptide may be an antigen or antibody. The method generally involves detecting a polypeptide in a sample comprising the steps of contacting a sample with a molecular biosensor of the invention. By way of non-limiting example, several useful molecular biosensors are illustrated in FIGS. 13, 14 and 15. FIG. 13A depicts a molecular biosensor comprising two aptamers recognizing two distinct epitopes of a protein. FIG. 13B depicts a molecular biosensor comprising a double stranded polynucleotide containing binding site for DNA binding protein and an aptamer recognizing a distinct epitope of the protein. FIG. 13C depicts a molecular biosensor comprising an antibody and an aptamer recognizing distinct epitopes of the protein. FIG. 13D depicts a molecular biosensor comprising a double stranded polynucleotide containing a binding site for a DNA binding protein and an antibody recognizing a distinct epitope of the protein. FIG. 13E depicts a molecular biosensor comprising two antibodies recognizing two distinct epitopes or two repeating epitopes of the protein. FIG. 13F depicts a molecular biosensor comprising two double stranded polynucleotide fragments recognizing two distinct sites of the protein. FIG. 13G depicts a molecular biosensor comprising two single stranded polynucleotide elements recognizing two distinct sequence elements of another single stranded polynucleotide. FIG. 13H depicts a molecular biosensor that allows for the direct detection of formation of a protein-polynucleotide complex using a double stranded polynucleotide fragment (containing the binding site of the protein) labeled with a first signaling oligonucleotide and the protein labeled with a second signaling oligonucleotide. FIG. 13I depicts a molecular biosensor that allows for the direct detection of the formation of a protein-protein complex using two corresponding proteins labeled with signaling oligonucleotides. FIG. 14 depicts a trivalent biosensor that allows for detection of a target molecule or complex with three different epitope binding agents. FIG. 15 depicts a competitive biosensor that allows detection of a target competitor in a solution.

In another embodiment, the molecular biosensors may be used to detect a target molecule that is a macromolecular complex in a sample. In this embodiment, the first epitope is preferably on one polypeptide and the second epitope is on another polypeptide, such that when a macromolecular complex is formed, the one and another polypeptides are bought into proximity, resulting in the stable interaction of the first epitope-binding agent construct and the second epitope-binding agent construct to produce a detectable signal, as described above. Also, the first and second epitope-binding agent constructs may be fixed to a surface or to each other via a flexible linker, as described above.

In another embodiment, the molecular biosensors may be used to detect a target molecule that is an analyte in a sample. In this embodiment, when the analyte is bound to a polypeptide or macromolecular complex, a first or second epitope is created or made available to bind to a first or second epitope-binding agent construct.

Thus, when an analyte is present in a sample that contains its cognate polypeptide or macromolecular binding partner, the first epitope-binding agent construct and the second epitope-binding agent construct are brought into stable proximity to produce a detectable signal, as described above. Also, the first and second epitope-binding agent constructs may be fixed to a surface or to each other via a flexible linker, as described above.

(b) Solid Surfaces

Optionally, the invention also encompasses a solid surface having the molecular constructs of the invention attached thereto. For example, in an embodiment for two-component biosensors, the first epitope-binding agent construct may be fixed to a surface, the second epitope-binding agent construct may be fixed to a surface, or both may be fixed to a surface. Non-limiting examples of suitable surfaces include microtitre plates, test tubes, beads, resins and other polymers, as well as other surfaces either known in the art or described herein. In a preferred embodiment, the first epitope-binding agent construct and the second epitope-binding agent construct may be joined with each other by a flexible linker to form a bivalent epitope-binding agent. Preferred flexible linkers include polyethylene glycol, such as Spacer 18 polymers and deoxythymidine ("dT") polymers.

Figure 19:
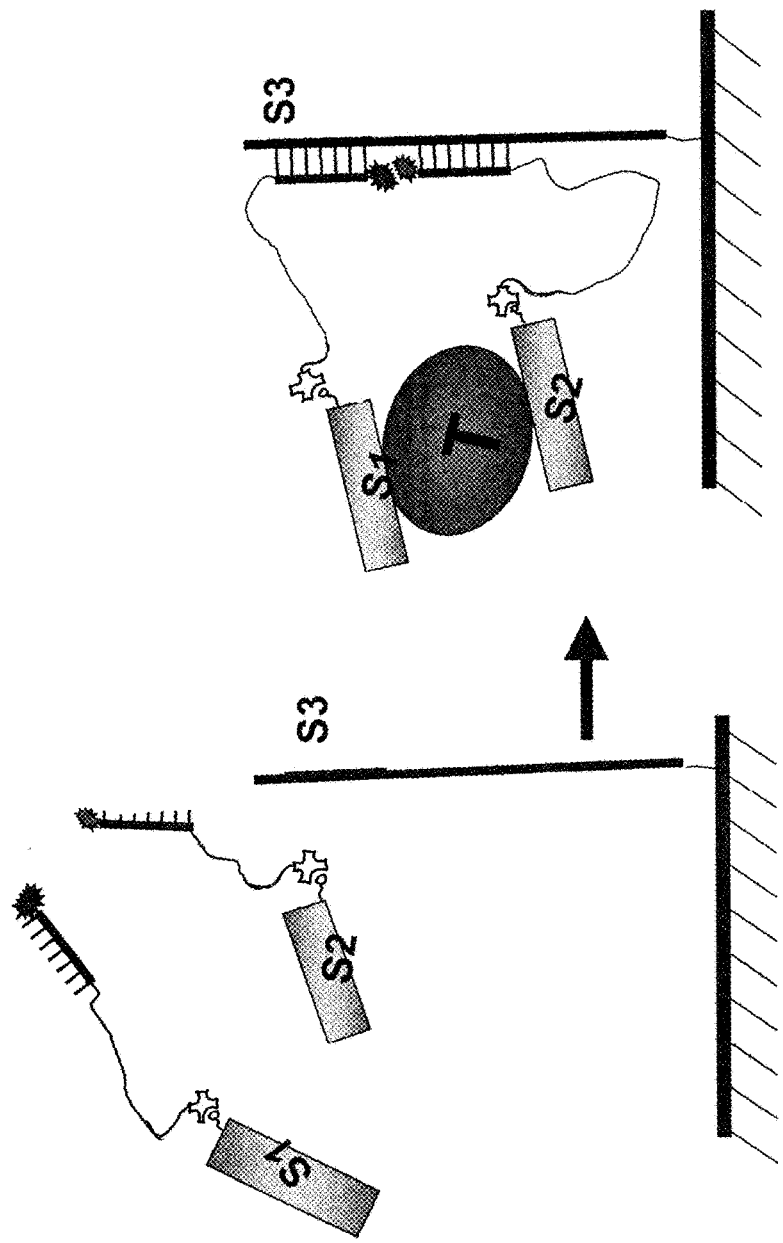
FIG. 19 depicts the solid-surface implementation of the three-component biosensor design.
Figure 20:
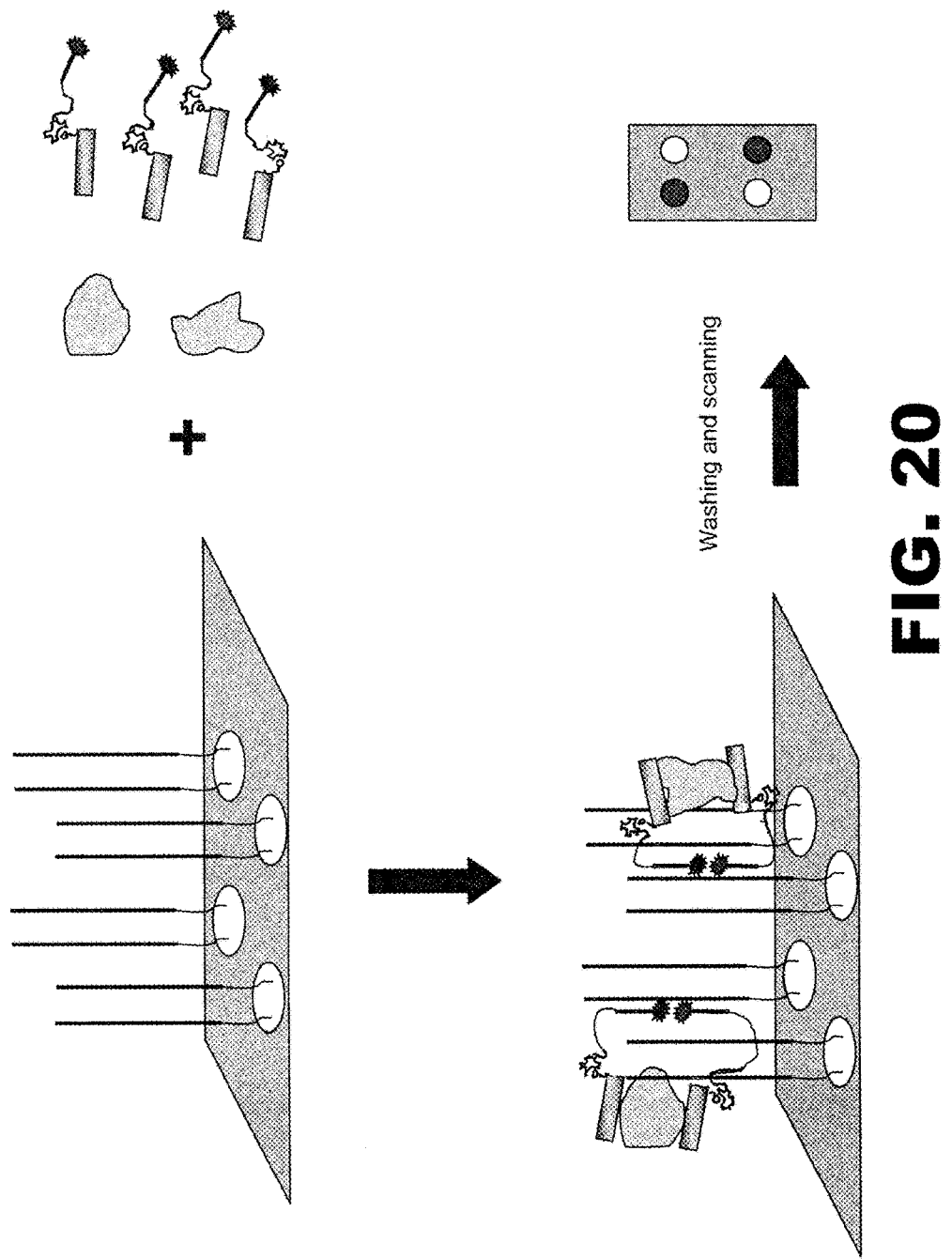
FIG. 20 depicts use of the three-component biosensor design for a microarray detection of a target.

Referring to FIGS. 19 and 20, in an exemplary embodiment the solid surface utilizes a three-component biosensor. In this embodiment, the oligonucleotide construct (S3 as described in the FIG. 19) may be immobilized on a solid surface. The first epitope binding agent and second epitope binding agent (e.g., S1 and S2 in the figure) are contacted with the surface comprising immobilized O and a sample that may comprise a target (e.g., T in figure). In the presence of target, the first epitope binding agent, second epitope binding agent, and target bind to immobilized O to form a complex. Several methods may be utilized to detect the presence of the complex comprising target. The method may include detecting a probe attached to the epitope-binding agents after washing out the unbound components. Alternatively, several surface specific real-time detection methods may be employed, including but not limited to surface plasmon resonance (SPR) or total internal reflection fluorescence (TIRF).

The oligonucleotide construct, O, may be immobilized to several types of suitable surfaces. The surface may be a material that may be modified to contain discrete individual sites appropriate for the attachment or association of the three-component biosensor and is amenable to at least one detection method. Non-limiting examples of surface materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. The size and shape of the surface may also vary without departing from the scope of the invention. A surface may be planar, a surface may be a well, i.e. a 364 well plate, or alternatively, a surface may be a bead or a slide.

The oligonucleotide construct, O, may be attached to the surface in a wide variety of ways, as will be appreciated by those in the art. O, for example, may either be synthesized first, with subsequent attachment to the surface, or may be directly synthesized on the surface. The surface and O may be derivatized with chemical functional groups for subsequent attachment of the two. For example, the surface may be derivatized with a chemical functional group including, but not limited to, amino groups, carboxyl groups, oxo groups or thiol groups. Using these functional groups, the O may be attached using functional groups either directly or indirectly using linkers. Alternatively, O may also be attached to the surface non-covalently. For example, a biotinylated O can be prepared, which may bind to surfaces covalently coated with streptavidin, resulting in attachment. Alternatively, O may be synthesized on the surface using techniques such as photopolymerization and photolithography. Additional methods of attaching O to a surface and methods of synthesizing O on surfaces are well known in the art, i.e. VLSIPS technology from Affymetrix (e.g., see U.S. Pat. No. 6,566,495, and Rockett and Dix, "DNA arrays: technology, options and toxicological applications," Xenobiotica 30(2):155-177, all of which are hereby incorporated by reference in their entirety).

(c) Competition Assays

In a further embodiment, a competitive molecular biosensor can be used to detect a competitor in a sample. Typically, the molecular biosensor used for competition assays will be a two-component molecular biosensor, as detailed in section (II) above. In an exemplary embodiment, the competitive molecular biosensor will comprise two epitope-binding agent constructs, which together have formula (XVII)

$(R^{47}-(X^1{}_{16})_n)-X^2{}_{16}-R^{48}-R^{49}-R^{50}$; and $(R^{51}-(X^1{}_{17})_m)-X^2{}_{17}-R^{52}-R^{53}-R^{54}$; (XVII)

wherein:
$X^1{}_{16}$ and $X^2{}_{16}$ are a first affinity binding pair;
$X^1{}_{17}$ and $X^2{}_{17}$ are a second affinity binding pair;
n and m are each an integer from 1 to 2;
$R^{47}$ is an epitope-binding agent that binds to a first epitope on a target molecule;
$R^{48}$ is a flexible linker attaching $X^2{}_{16}$ to $R^{49}$;
$R^{49}$ and $R^{53}$ are a pair of complementary nucleotide sequences having a free energy for association from about −5.5 kcal/mole to about −8.0 kcal/mole at a temperature from about 21° C. to about 40° C. and at a salt concentration from about 1 mM to about 100 mM;
$R^{50}$ and $R^{54}$ together comprise a detection means such that when $R^{49}$ and $R^{53}$ associate a detectable signal is produced;
$R^{51}$ is an epitope binding agent that binds to $R^{47}$; and
$R^{52}$ is a flexible linker attaching $X^2{}_{17}$ to $R^{53}$ In another alternative, the competitive molecular biosensor will comprise formula (XVII) wherein:
$X^1{}_{16}$ and $X^2{}_{16}$ are a first affinity binding pair;
$X^1{}_{17}$ and $X^2{}_{17}$ are a second affinity binding pair;
n and m are each an integer from 1 to 2;
$R^{47}$ is a peptide, a small molecule, or protein epitope-binding agent that binds to a first epitope on a target molecule;
$R^{48}$ is a flexible linker attaching $X^2{}_{16}$ to $R^{49}$;
$R^{49}$ and $R^{53}$ are a pair of complementary nucleotide sequences having a free energy for association from about −5.5 kcal/mole to about −8.0 kcal/mole at a temperature from about 21° C. to about 40° C. and at a salt concentration from about 1 mM to about 100 mM;
$R^{50}$ and $R^{54}$ together comprise a detection means such that when $R^{49}$ and $R^{53}$ associate a detectable signal is produced;
$R^{51}$ is an antibody or antibody fragment epitope binding agent that binds to $R^{47}$; and
$R^{52}$ is a flexible linker attaching $X^2{}_{17}$ to $R^{53}$ For each embodiment for competitive molecular biosensors having formula (XVII), suitable affinity binding pairs, flexible linkers, complementary nucleotide sequences, detection means, and epitope-binding agent constructs are described in Section II for two-component molecular biosensors having formula (I).

To detect the presence of a target, referring to FIG. 15, the molecular biosensor is comprised of two epitope binding agents—the first epitope binding agent is a peptide that is a solvent exposed epitope of a target protein, and the second epitope binding agent is an antibody which binds to the first epitope binding agent. When the biosensor is in solution without the target, a signal is created because the first epitope binding agent and the second epitope binding agent bind, thereby bringing the first signaling oligo and the second signaling oligo into close proximity, producing a detectable signal from the first and second label. When the target competitive protein (comprising the solvent exposed epitope used for the first epitope binding agent) is added to the biosensor, the target protein competes with the first epitope binding agent for binding to the second epitope binding agent. This competition displaces the first epitope-binding agent from the second epitope binding agent, which destabilizes the first signaling oligo from the second signaling oligo, resulting in a decrease in signal. The decrease in signal can be used as a measurement of the concentration of the competitive target.

(d) Use of Biosensors with No Detection Means

Alternatively, in certain embodiments it is contemplated that the molecular biosensor may not include a detections means. By way of example, when the molecular biosensor is a bivalent epitope-binding agent construct, the bivalent epitope-binding agent construct may not have labels for detection. It is envisioned that these alternative bivalent epitope-binding agent constructs may be used much like antibodies to detect molecules, bind molecules, purify molecules (as in a column or pull-down type of procedure), block molecular interactions, facilitate or stabilize molecular interactions, or confer passive immunity to an organism. It is further envisioned that the bivalent epitope-binding agent construct can be used for therapeutic purposes. This invention enables the skilled artisan to build several combinations of epitope-binding agent that recognize any two or more disparate epitopes form any number of molecules into a bivalent, trivalent, or other multivalent epitope-binding agent construct to pull together those disparate molecules to test the effect or to produce a desired therapeutic outcome. For example, a bivalent epitope-binding agent construct may be constructed to facilitate the binding of a ligand to its receptor in a situation wherein the natural binding kinetics of that ligand to the receptor is not favorable (e.g., insulin to insulin receptor in patients suffering diabetes.)

Furthermore, as detailed above, a three component biosensor may also not comprise a detection means. In these sensors, a change of mass, electrical, or optical properties upon target binding may provide a detectable signal.

(e) Diagnostics

In yet another embodiment, the invention is directed to a method of diagnosing a disease comprising the steps of (a) obtaining a sample from a patient, (b) contacting the sample with a first epitope-binding agent construct and a second epitope-binding agent construct, and (c) detecting the presence of a polypeptide, antibody, analyte or macromolecular complex in the sample using a detection method, wherein the presence of the polypeptide, antibody, analyte or macromolecular complex in the sample indicates whether a disease is present in the patient. In one embodiment, (a) the first epitope-binding agent construct is a first aptamer to which a first label and a first signaling oligo are attached, (b) the second epitope-binding agent construct is a second aptamer to which a second label and a second signaling oligo, which is complementary to the first signaling oligo, are attached, and (c) the detection method is a fluorescence detection method, wherein, (d) when the first aptamer binds to the polypeptide and the second aptamer binds to the polypeptide, (e) the first signaling oligo and the second signaling oligo associate with each other, and (f) the first label is brought into proximity to the second label such that a change in fluorescence occurs. In another embodiment, (a) the first epitope-binding agent construct is a first peptide to which a first label and a first signaling oligo are attached, (b) the second epitope-binding agent construct is a second peptide to which a second label and a second signaling oligo, which is complementary to the first signaling oligo, are attached, and (c) the detection method is a fluorescence detection method, wherein, (d) when the first peptide binds to the polypeptide and the second peptide binds to the polypeptide, (e) the first signaling oligo and the second signaling oligo associate with each other, and (f) the first label is brought into proximity to the second label such that a change in fluorescence occurs. In yet another embodiment, (a) the first epitope-binding agent construct is a first antibody to which a first label and a first signaling oligo are attached, (b) the second epitope-binding agent construct is a second antibody to which a second label and a second signaling oligo, which is complementary to the first signaling oligo, are attached, and (c) the detection method is a fluorescence detection method, wherein, (d) when the first antibody binds to the polypeptide and the second antibody binds to the polypeptide, (e) the first signaling oligo and the second signaling oligo associate with each other, and (f) the first label is brought into proximity to the second label such that a change in fluorescence occurs. In other embodiments, the first epitope binding agent and the second epitope-binding agents are different types of epitope binding agents (i.e. an antibody and a peptide, an aptamer and an antibody, etc.). Preferred samples include blood, urine, ascites, cells and tissue samples/biopsies. Preferred patients include humans, farm animals and companion animals.

In still yet another embodiment, the invention is directed to a method of diagnosing a disease comprising the steps of (a) obtaining a sample from a patient, (b) contacting the sample with a first epitope-binding agent construct and a second epitope-binding agent construct, and an oligonucleotide construct and (c) detecting the presence of a polypeptide, antibody, analyte or macromolecular complex in the sample using a detection method, wherein the presence of the polypeptide, antibody, analyte or macromolecular complex in the sample indicates whether a disease is present in the patient. In one embodiment, (a) the first epitope-binding agent construct is a first aptamer, peptide or antibody to which a first signaling oligo, which is complementary to a first region of the oligonucleotide construct, and a label are attached, (b) the second epitope-binding agent construct is a second aptamer, peptide or antibody to which a second signaling oligo, which is complementary to a second region of the oligonucleotide construct, and a label are attached, and (c) the detection method is a fluorescence detection method, wherein, (d) when the first aptamer, peptide or antibody binds to the polypeptide and the second aptamer, peptide or antibody binds to the polypeptide, (e) the first signaling oligo and the second signaling oligo associate with O, and (f) the first label is brought into proximity to the second label such that a change in fluorescence occurs. In another embodiment, (a) the first epitope-binding agent construct is a first aptamer, peptide or antibody to which a first signaling oligo, which is complementary to a first region of the oligonucleotide construct, is attached, (b) the second epitope-binding agent construct is a second aptamer, peptide or antibody to which a second signaling oligo, which is complementary to a second region of the oligonucleotide construct, is attached, (c) the oligonucleotide construct is intact thereby generating a signal, and (d) the detection method is a fluorescence detection method, wherein, (e) when the first aptamer, peptide or antibody binds to the polypeptide and the second aptamer, peptide or antibody binds to the polypeptide, (e) the first signaling oligo and the second signaling oligo associate with O thereby generating a restriction enzyme site, and (f) the restriction site is cleaved thereby eliminating the fluorescent signal in the present of target. In another embodiment, (a) the first epitope-binding agent construct is a first aptamer, peptide or antibody to which a first signaling oligo, which is complementary to a first region of the oligonucleotide construct, is attached, (b) the second epitope-binding agent construct is a second aptamer, peptide or antibody to which a second signaling oligo, which is complementary to a second region of the oligonucleotide construct, is attached, (c) the oligonucleotide construct comprises a detectable label, and (d) the detection method is a fluorescence detection method, wherein, (e) when the first aptamer, peptide or antibody binds to the polypeptide and the second aptamer, peptide or antibody binds to the polypeptide, (e) the first signaling oligo and the second signaling oligo associate with O thereby generating a restriction enzyme site, and (f) the restriction site is cleaved thereby generating the fluorescent signal in the present of target. In other embodiments, the first epitope binding agent and the second epitope-binding agents are different types of epitope binding agents (i.e. an antibody and a peptide, an aptamer and an antibody, etc.). Preferred samples include blood, urine, ascites, cells and tissue samples/biopsies. Preferred patients include humans, farm animals and companion animals.

In each of the above embodiments, the labels are optional. When a label is not present, the presence of a target molecule may be detected by a change in mass, electrical, or optical properties of the sensor upon target binding.

In yet another embodiment, the invention is directed to a method of screening a sample for useful reagents comprising the steps of (a) contacting a sample with a first epitope-binding agent construct and a second epitope-binding agent construct, and (b) detecting the presence of a useful reagent in the sample using a detection method. Preferred reagents include a polypeptide, which comprises a first epitope and a second epitope, an analyte that binds to a polypeptide (in which case the method further comprises the step of adding the polypeptide to the screening mixture), an antibody, and a potential therapeutic composition. In one embodiment, (a) the first epitope binding agent is a first aptamer to which a first label and a first signaling oligo are attached, (b) the second epitope binding agent is a second aptamer to which a second label and a second signaling oligo, which is complementary to the first signaling oligo, are attached, and (c) the detection method is a fluorescence detection method, wherein, (d) when the first aptamer binds to the polypeptide and the second aptamer binds to the polypeptide, (e) the first signaling oligo and the second signaling oligo associate with each other, and (f) the first label is brought into proximity to the second label such that a change in fluorescence occurs. In another embodiment, (a) the first epitope binding agent is a first peptide to which a first label and a first signaling oligo are attached, (b) the second epitope binding agent is a second peptide to which a second label and a second signaling oligo, which is complementary to the first signaling oligo, are attached, and (c) the detection method is a fluorescence detection method, wherein, (d) when the first peptide binds to the polypeptide and the second peptide binds to the polypeptide, (e) the first signaling oligo and the second signaling oligo associate with each other, and (f) the first label is brought into proximity to the second label such that a change in fluorescence occurs. In yet another embodiment, (a) the first epitope binding agent is a first antibody to which a first label and a first signaling oligo are attached, (b) the second epitope binding agent is a second antibody to which a second label and a second signaling oligo, which is complementary to the first signaling oligo, are attached, and (c) the detection method is a fluorescence detection method, wherein, (d) when the first antibody binds to the polypeptide and the second antibody binds to the polypeptide, (e) the first signaling oligo and the second signaling oligo associate with each other, and (f) the first label is brought into proximity to the second label such that a change in fluorescence occurs. In other embodiments, the first epitope binding agent and the second epitope-binding agents are different types of epitope binding agents (i.e. an antibody and a peptide, an aptamer and an antibody, etc.).

VII Kits

In another aspect, the present invention encompasses a kit for converting an epitope binding agent into a molecular biosensor. In another aspect, the present invention encompasses a kit for converting an epitope binding agent into an epitope binding agent construct. Generally speaking, the kit comprises (i) means for modifying at least one epitope binding agent with a first member of an affinity binding pair and (ii) a signaling oligonucleotide attached to a second member of the affinity binding pair through a flexible linker. In another embodiment, a kit comprises means for constructing a signaling oligonucleotide attached to a second member of the affinity binding pair through a flexible linker. Suitable epitope binding agents, affinity binding pairs, signaling oligonucleotides, and flexible linkers are described above. In some embodiments, the first member of the affinity binding pair is a ligand and the second member of the affinity binding pair is the ligand's cognate binding partner. In other embodiments, the second member of the affinity binding pair is a ligand and the first member of the affinity binding pair is the ligand's cognate binding partner. In each of the foregoing embodiments, an epitope binding agent may be modified at least once with a member of an affinity binding pair. By way of non-limiting example, an epitope binding agent can be modified with one or more ligands. In a preferred embodiment, the affinity binding pair is biotin and a biotin binding protein. In certain embodiments, a biotin binding protein is selected from the group consisting of avidin, deglycosylated avidin, native streptavidin, and recombinant streptavidin. In an exemplary embodiment, a kit comprises (i) means for modifying at least one epitope binding agent with one or more biotin or biotin derivatives and (ii) a signaling oligonucleotide attached to recombinant streptavidin through a flexible linker. In another exemplary embodiment, a kit comprises a signaling oligonucleotide attached to a recombinant streptavidin through a flexible linker. In each of the foregoing embodiments, a kit may further comprise an oligonucleotide construct. Suitable oligonucleotide constructs are described above.

In some embodiments, a kit of the invention is for converting an epitope binding agent into a molecular biosensor comprising two epitope binding constructs. The kit comprises (i) means for modifying at least two epitope binding agents with a first member of an affinity binding pair, and (ii) a signaling oligonucleotide attached to a second member of the affinity binding pair through a flexible linker, wherein the flexible linker and signaling oligonucleotide are as described in Section II. In an aspect, the first member of the affinity binding pair is a ligand and the second member of the affinity binding pair is the ligand's cognate binding partner. In another aspect, the second member of the affinity binding pair is a ligand and the first member of the affinity binding pair is the ligand's cognate binding partner. In each of the foregoing embodiments, an epitope binding agent may be modified at least once with a member of an affinity binding pair. By way of non-limiting example, an epitope binding agent can be modified with one or more ligands. In a preferred embodiment, the affinity binding pair is biotin and a biotin binding protein. In certain embodiments, a biotin binding protein is selected from the group consisting of avidin, deglycosylated avidin, native streptavidin, and recombinant streptavidin. In an exemplary embodiment, a kit comprises means for modifying at least two epitope binding agents with one or more biotin or biotin derivatives, and (ii) a signaling oligonucleotide attached to a recombinant streptavidin through a flexible linker, wherein the flexible linker and signaling oligonucleotide are as described in Section II. In another exemplary embodiment, a kit comprises means for modifying at least two epitope binding agents with one or more biotin or biotin derivatives, (ii) a linker attached to a recombinant streptavidin, and (iii) a detectable label attached to a signaling oligonucleotide, wherein the flexible linker and signaling oligonucleotide are as described in Section II. In still another exemplary embodiment, a kit comprises (i) a linker attached to a recombinant streptavidin, and (ii) a detectable label attached to a signaling oligonucleotide, wherein the flexible linker and signaling oligonucleotide are as described in Section II, provided the user provides the at least two epitope binding agents modified with one or more biotin or biotin derivatives.

In other embodiments, a kit of the invention is for converting an epitope binding agent into a molecular biosensor comprising two epitope binding constructs and an oligonucleotide construct. The kit comprises (i) means for modifying at least two epitope binding agents with a first member of an affinity binding pair, (ii) a signaling oligonucleotide attached to a second member of the affinity binding pair through a flexible linker, and (iii) an oligonucleotide construct, wherein the flexible linker, signaling oligonucleotide, and oligonucleotide construct are as described in Section III. In an aspect, the first member of the affinity binding pair is a ligand and the second member of the affinity binding pair is the ligand's cognate binding partner. In another aspect, the second member of the affinity binding pair is a ligand and the first member of the affinity binding pair is the ligand's cognate binding partner. In each of the foregoing embodiments, an epitope binding agent may be modified at least once with a member of an affinity binding pair. By way of non-limiting example, an epitope binding agent can be modified with one or more ligands. In a preferred embodiment, the affinity binding pair is biotin and a biotin binding protein. In certain embodiments, a biotin binding protein is selected from the group consisting of avidin, deglycosylated avidin, native streptavidin, and recombinant streptavidin. In an exemplary embodiment, a kit comprises means for modifying at least two epitope binding agents with one or more biotin or biotin derivatives, and (ii) a signaling oligonucleotide attached to a second member of the affinity binding pair through a flexible linker, and (iii) an oligonucleotide construct, wherein the flexible linker, signaling oligonucleotide, and oligonucleotide construct are as described in Section III. In another exemplary embodiment, a kit comprises means for modifying at least two epitope binding agents with one or more biotin or biotin derivatives, and (ii) a linker attached to a second member of the affinity binding pair through a flexible linker, (iii) a detectable label attached to a signaling oligonucleotide, and (iv) an oligonucleotide construct, wherein the flexible linker, signaling oligonucleotide, and oligonucleotide construct are as described in Section III. In still another exemplary embodiment, a kit comprises (i) a linker attached to a second member of the affinity binding pair through a flexible linker, (ii) a detectable label attached to a signaling oligonucleotide, and (iii) an oligonucleotide construct, wherein the flexible linker, signaling oligonucleotide, and oligonucleotide construct are as described in Section III, provided the user provides at least two epitope binding agents modified with one or more biotin or biotin derivatives.

In other embodiments, a kit of the invention is for converting an epitope binding agent into a molecular biosensor comprising two epitope binding constructs. The kit comprises (i) means for modifying at least two epitope binding agents with a first member of an affinity binding pair, and (ii) a signaling oligonucleotide attached to a second member of the affinity binding pair through a flexible linker, wherein the flexible linker and signaling oligonucleotide are as described in Section IV. In an aspect, the first member of the affinity binding pair is a ligand and the second member of the affinity binding pair is the ligand's cognate binding partner. In another aspect, the second member of the affinity binding pair is a ligand and the first member of the affinity binding pair is the ligand's cognate binding partner. In each of the foregoing embodiments, an epitope binding agent may be modified at least once with a member of an affinity binding pair. By way of non-limiting example, an epitope binding agent can be modified with one or more ligands. In a preferred embodiment, the affinity binding pair is biotin and a biotin binding protein. In certain embodiments, a biotin binding protein is selected from the group consisting of avidin, deglycosylated avidin, native streptavidin, and recombinant streptavidin. In an exemplary embodiment, a kit comprises (i) means for modifying at least two epitope binding agents with one or more biotin or biotin derivatives, and (ii) a signaling oligonucleotide attached to a recombinant streptavidin through a flexible linker, wherein the flexible linker and signaling oligonucleotide are as described in Section IV. In another exemplary embodiment, a kit comprises ii) a signaling oligonucleotide attached to a recombinant streptavidin through a flexible linker, wherein the flexible linker and signaling oligonucleotide are as described in Section IV, provided the user provides at least two epitope binding agents modified with one or more biotin or biotin derivatives.

In other embodiments, a kit of the invention is for converting an epitope binding agent into a molecular biosensor comprising two epitope binding constructs and an oligonucleotide construct. The kit comprises (i) means for modifying at least two epitope binding agents with a first member of an affinity binding pair, (ii) a signaling oligonucleotide attached to a second member of the affinity binding pair through a flexible linker, and (iii) an oligonucleotide construct, wherein the flexible linker, signaling oligonucleotide, and oligonucleotide construct are as described in Section IV. In an aspect, the first member of the affinity binding pair is a ligand and the second member of the affinity binding pair is the ligand's cognate binding partner. In another aspect, the second member of the affinity binding pair is a ligand and the first member of the affinity binding pair is the ligand's cognate binding partner. In each of the foregoing embodiments, an epitope binding agent may be modified at least once with a member of an affinity binding pair. By way of non-limiting example, an epitope binding agent can be modified with one or more ligands. In a preferred embodiment, the affinity binding pair is biotin and a biotin binding protein. In certain embodiments, a biotin binding protein is selected from the group consisting of avidin, deglycosylated avidin, native streptavidin, and recombinant streptavidin. In an exemplary embodiment, a kit comprises (i) means for modifying at least two epitope binding agents with one or more biotin or biotin derivatives, and (ii) a signaling oligonucleotide attached to a second member of the affinity binding pair through a flexible linker, and (iii) an oligonucleotide construct, wherein the flexible linker, signaling oligonucleotide, and oligonucleotide construct are as described in Section IV. In another exemplary embodiment, a kit comprises (i) a signaling oligonucleotide attached to a second member of the affinity binding pair through a flexible linker, and (ii) an oligonucleotide construct, wherein the flexible linker, signaling oligonucleotide, and oligonucleotide construct are as described in Section IV, provided the user provides at least two epitope binding agents modified with one or more biotin or biotin derivatives.

As used herein, "means for modifying at least one epitope binding agent with a first member of an affinity binding pair" refers to reagents and/or instructions. A skilled artisan will appreciate that reagents needed may vary depending on the affinity binding pair and the epitope binding agent, and that many reagents needed are commercially available and/or can be readily produced in a laboratory setting. For example, if the affinity binding pair is biotin and a biotin binding partner and the kit comprises means for modifying at least one epitope binding agent with biotin, then it is sufficient for the "means" to be instructions detailing how to modify the epitope binding agent. Such instructions may recommend certain forms or derivatives of biotin and suitable parameters for the modification reaction, such as ratio of biotin to epitope binding reagent, length of the reaction, temperature of the reaction, suitable buffers, and other parameters familiar to a skilled artisan. Alternatively, the "means" may comprise instructions and reagents. Non-limiting examples of reagents may include a member of the affinity binding pair, buffers, enzymes, cells, and solutions.

In yet another embodiment, the invention encompasses a kit comprising any of the preceding biosensors.

A kit of the invention is useful in the detection of polypeptides, analytes or macromolecular complexes, and as such, may be used in research or medical/veterinary diagnostics applications.

DEFINITIONS

As used herein, the term "affinity binding pair" refers to a ligand and its cognate binding partner. A binding partner may be capable of binding to one or more than one ligand. Binding partners capable of binding more than one of the ligand can be described as multivalent.

The term "analyte" refers generally to a ligand, chemical moiety, compound, ion, salt, metal, enzyme, secondary messenger of a cellular signal transduction pathway, drug, nanoparticle, environmental contaminant, toxin, fatty acid, steroid, hormone, carbohydrate, amino acid, antigen, peptide, polypeptide, protein or other amino acid polymer, microbe, virus or any other agent which is capable of binding to a polypeptide, protein or macromolecular complex in such a way as to create an epitope or alter the availability of an epitope for binding to an aptamer.

The term "antibody" generally means a polypeptide or protein that recognizes and can bind to an epitope of an antigen or protein. An antibody, as used herein, may be a complete antibody as understood in the art, i.e., consisting of two heavy chains and two light chains, or be selected from a group comprising polyclonal antibodies, ascites, Fab fragments, Fab' fragments, monoclonal antibodies, chimeric antibodies, humanized antibodies, and a peptide comprising a hypervariable region of an antibody. In all instances, an antibody specifically recognizes a peptide or antigen via its variable region. The term "specifically recognizes" herein means antibodies bind to the protein, peptide or antigen with an affinity constant or Affinity of interaction ($K_D$) in the range of at least 0.1 mM to 1 pM, or in the range of at least 0.1 pM to 10 nM, with a preferred range being 0.1 pM to 1 nM.

The term "aptamer" refers to a polynucleotide, generally a RNA or a DNA that has a useful biological activity in terms of biochemical activity, molecular recognition or binding attributes. Usually, an aptamer has a molecular activity such as binding to a target molecule at a specific epitope (region). It is generally accepted that an aptamer, which is specific in its binding to any polypeptide, may be synthesized and/or identified by in vitro evolution methods.

As used herein, "detection method" means any of several methods known in the art to detect a molecular interaction event. The phrase "detectable signal", as used herein, is essentially equivalent to "detection method." Detection methods include detecting changes in mass (e.g., plasmin resonance), changes in fluorescence (e.g., fluorescent resonance energy transfer (FRET), time resolved-FRET, fluorescence life-time imaging, lanthamide resonance energy transfer (LRET), FCCS, fluorescence quenching or increasing fluorescence, fluorescence polarization, flow cytometry), enzymatic activity (e.g., depletion of substrate or formation of a product, such as a detectable dye—NBT-BCIP system of alkaline phosphatase is an example), changes in chemiluminescence or scintillation (e.g., scintillation proximity assay, luminescence resonance energy transfer, bioluminescence resonance energy transfer and the like), and ground-state complex formation, excimer formation, colorimetric substance detection, phosphorescence, electro-chemical changes, residence time changes, and redox potential changes. Detection methods may further include changes in electrical or optical properties.

The term "epitope" refers generally to a particular region of a target molecule. Examples include an antigen, a hapten, a molecule, a polymer, a prion, a microbe, a cell, a peptide, polypeptide, protein, or macromolecular complex. An epitope may consist of a small peptide derived from a larger polypeptide. An epitope may be a two or three-dimensional surface or surface feature of a polypeptide, protein or macromolecular complex that comprises several non-contiguous peptide stretches or amino acid groups. An epitope may be an antibody.

The term "epitope binding agent" refers to a substance that is capable of binding to a specific epitope of an antigen, a polypeptide, a protein or a macromolecular complex. Non-limiting examples of epitope binding agents include aptamers, thioaptamers, double-stranded DNA sequence, peptides and polypeptides, ligands and fragments of ligands, receptors and fragments of receptors, antibodies and fragments of antibodies, polynucleotides, coenzymes, coregulators, allosteric molecules, peptide nucleic acids, locked nucleic acids, phosphorodiamidate morpholino oligomers (PMO) and ions. Peptide epitope binding agents include ligand regulated peptide epitope binding agents.

The term "epitope-binding agent construct" refers to a construct that contains an epitope-binding agent and can serve in a "molecular biosensor" with another molecular biosensor. Preferably, an epitope-binding agent construct also contains a "linker," and a "signaling oligo". Epitope-binding agent constructs can be used to initiate the aptamer selection methods of the invention. A first epitope-binding agent construct and a second epitope-binding agent construct may be joined together by a "linker" to form a "bivalent epitope-binding agent construct." An epitope-binding agent construct can also be referred to as a molecular recognition construct. An aptamer construct is a special kind of epitope-binding agent construct wherein the epitope binding agent is an aptamer.

The phrase "in vitro evolution" generally means any method of selecting for an aptamer that binds to a biomolecule, particularly a peptide or polypeptide. In vitro evolution is also known as "in vitro selection", "SELEX" or "systematic evolution of ligands by exponential enrichment." Briefly, in vitro evolution involves screening a pool of random polynucleotides for a particular polynucleotide that binds to a biomolecule or has a particular activity that is selectable. Generally, the particular polynucleotide (i.e., aptamer) represents a very small fraction of the pool, therefore, a round of aptamer amplification, usually via polymerase chain reaction, is employed to increase the representation of potentially useful aptamers. Successive rounds of selection and amplification are employed to exponentially increase the abundance of the particular and useful aptamer. In vitro evolution is described in Famulok, M.; Szostak, J. W., In Vitro Selection of Specific Ligand Binding Nucleic Acids, Angew. Chem. 1992, 104, 1001. (Angew. Chem. Int. Ed. Engl. 1992, 31, 979-988.); Famulok, M.; Szostak, J. W., Selection of Functional RNA and DNA Molecules from Randomized Sequences, Nucleic Acids and Molecular Biology, Vol 7, F. Eckstein, D. M. J. Lilley, Eds., Springer Verlag, Berlin, 1993, pp. 271; Klug, S.; Famulok, M., All you wanted to know about SELEX; Mol. Biol. Reports 1994, 20, 97-107; and Burgstaller, P.; Famulok, M. Synthetic ribozymes and the first deoxyribozyme; Angew. Chem. 1995, 107, 1303-1306 (Angew. Chem. Int. Ed. Engl. 1995, 34, 1189-1192), which are incorporated herein by reference.

In the practice of certain embodiments of the invention, in vitro evolution is used to generate aptamers that bind to distinct epitopes of any given polypeptide or macromolecular complex. Aptamers are selected against "substrates", which contain the epitope of interest. As used herein, a "substrate" is any molecular entity that contains an epitope to which an aptamer can bind and that is useful in the selection of an aptamer.

The term "label", as used herein, refers to any substance attachable to a polynucleotide, polypeptide, aptamer, nucleic acid component, or other substrate material, in which the substance is detectable by a detection method. Non-limiting examples of labels applicable to this invention include but are not limited to luminescent molecules, chemiluminescent molecules, fluorochromes, fluorescent quenching agents, colored molecules, radioisotopes, scintillants, massive labels (for detection via mass changes), biotin, avidin, streptavidin, protein A, protein G, antibodies or fragments thereof, Grb2, polyhistidine, Ni2+, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present invention.

As used herein, the term "macromolecular complex" refers to a composition of matter comprising a macromolecule. Preferably, these are complexes of one or more macromolecules, such as polypeptides, lipids, carbohydrates, nucleic acids, natural or artificial polymers and the like, in association with each other. The association may involve covalent or non-covalent interactions between components of the macromolecular complex. Macromolecular complexes may be relatively simple, such as a ligand bound polypeptide, relatively complex, such as a lipid raft, or very complex, such as a cell surface, virus, bacteria, spore and the like. Macromolecular complexes may be biological or non-biological in nature.

The term "molecular biosensor" and "molecular beacon" are used interchangeably herein to refer to a construct comprised of at least two epitope-binding agent constructs. The molecular biosensor can be used for detecting or quantifying the presence of a target molecule using a chemical-based system for detecting or quantifying the presence of an analyte, a prion, a protein, a nucleic acid, a lipid, a carbohydrate, a biomolecule, a macromolecular complex, a fungus, a microbial organism, or a macromolecular complex comprised of biomolecules using a measurable read-out system as the detection method.

The phrase "natural cognate binding element sequence" refers to a nucleotide sequence that serves as a binding site for a nucleic acid binding factor. Preferably the natural cognate binding element sequence is a naturally occurring sequence that is recognized by a naturally occurring nucleotide binding factor.

The term "nucleic acid construct" refers to a molecule comprising a random nucleic acid sequence flanked by two primers. Preferably, a nucleic acid construct also contains a signaling oligo. Nucleic acid constructs are used to initiate the aptamer selection methods of the invention.

The term "signaling oligo" means a short (generally 2 to 15 nucleotides, preferably 5 to 7 nucleotides in length) single-stranded polynucleotide. Signaling oligos are typically used in pairs comprising a first signaling oligo and a second signaling oligo. Preferably, the first signaling oligo sequence is complementary to the second signaling oligo. Preferably, the first signaling oligo and the second signaling oligo cannot form a stable association with each other through hydrogen bonding unless the first and second signaling oligos are brought into close proximity to each other through the mediation of a third party agent.

EXAMPLES

The following examples illustrate various iterations of the invention.

Example 1

We encountered problems to convert certain antigens (proteins, peptides or other organic molecules) into molecular biosensors to detect their corresponding antibodies, especially when these antigens are poorly soluble. In particular, the antigens precipitated when modifications were made. When these molecules are not soluble, we are not able to modify them and the epitope binding agent (PINCER) cannot be generated. To solve this problem, a new design was developed which allows the whole HCV antigen molecule to be converted into an epitope binding construct in the presence of a high concentration of urea to keep the antigen soluble. This design then became a universal approach for developing new molecular biosensors, allowing the production of groups of biosensors that varied only in terms of the epitope binding agent. For example, this design can allow us to dissolve these types of molecules in 4-6 M urea, a condition upon which biotinylation works well. Streptavidin can bind to the biotinylated molecule very well even in 4M urea. When the assay is performed, the concentration of PINCER is usually in 10-30 nM range and most of them become soluble in the presence of mild detergents such as tween-20. In all cases we have tested using this preparation methodology, the PINCER assay works well. Further, we have also noted that even though some antigens are soluble initially, they become insoluble during the modification procedures to generate the epitope binding agent due to pH change or other known factors. However, the new methodology, using biotinylation, occurs in pH 7-7.5 such that the majority of the time, solubility of the molecule is not affected. Further, unlike previous biosensor designs, the modified streptavidin may be packaged as a kit, allowing user to biotinylate their macromolecule of choice.

One of the designs is illustrated in FIG. 1. In this design, the antigen is modified with biotin either on Avitag by an enzyme, or randomly on the whole molecule via chemical modification. Streptavidin (SA) is first modified with oligonucleotide A2 through crosslinker PEG12. The biotinylated antigen is then converted into PINCER A or B by binding with SA-A2, followed by hybridizing with oligonucleotide AA2 or AM, each conjugated with a different fluorescent dye. These dyes when in proximity can generate FRET signal. In the presence of the specific antibody, two modified antigens (PINCER A and PINCER B) will simultaneously bind to the variable domain of the antibody and enhance the annealing of the two oligonucleotide AA2 and AM, which will bring the fluorescent dyes to a close proximity and initiate FRET (fluorescence resonance energy transfer).

Example 2

Antigen Detection Using Biotinylated Antibodies

Figure 2:
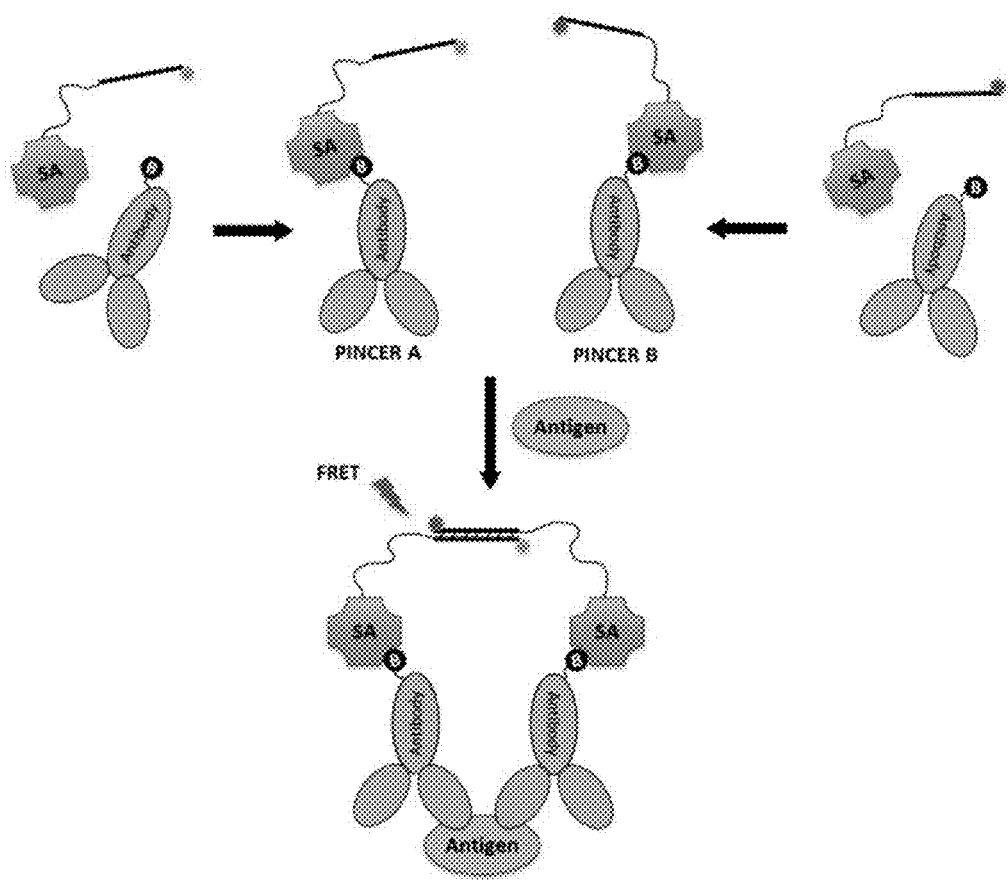
FIG. 2 is an illustration of a generic two-component biosensor assay for antigen detection. In this illustration, the affinity binding pair is biotin and streptavidin, the first and second epitope binding agents are antibodies (either the same antibody or different antibodies), and the target molecule is an antigen specifically recognized by the first and second epitope binding agents. Contacting a first signaling oligonucleotide attached to streptavidin through a flexible linker with a first epitope binding agent modified with biotin results in the non-covalent binding of biotin to streptavidin and the tight association of the epitope binding agent to the signaling oligonucleotide to produce the first epitope binding agent construct (labeled Pincer A in the illustration). The second epitope binding agent construct is similarly produced (labeled Pincer B in the illustration). Co-association of the two epitope-binding agent constructs with the target molecule results in bringing the two signaling oligonucleotides into proximity such that a detectable signal is produced.

Considering the random modification can result in multiple biotins on one antigen, and up to four biotinylated antigens can bind to one streptavidin, all of which could affect the assay performance. To find out how this could affect the performance of the PINCER assay, we conducted a systematic study to test these factors in a model system that utilizes human C-reactive protein (hCRP) and its monoclonal antibodies since the antibody/antigen binding has been well characterized. The design of the model system is illustrated in FIG. 2, which is similar but a little different from the above design in FIG. 1, since we want to test these factors on a more generic PINCER assay. In this design, two monoclonal anti-hCRP antibodies are biotinylated and converted into to PINCER A and PINCER B by binding to SA-A2, followed by hybridizing with oligonucleotide AA2 or AM, each conjugated with a different fluorescent dye. These dyes when in proximity can generate FRET signal. In the presence of hCRP protein, these two monoclonal antibodies will simultaneously bind to the epitopes on the hCRP protein and initiate FRET signal.

Biotinylation of antibodies: Anti-hCRP antibodies 5404 and 5405 were each mixed with Biotin-LCLC-NHS (Pierce) under the following conditions: a. 1:15 (Ab:biotin) molar ratio for 1 hour; b. 1:25 for 2 hours; c. 1:50 for 2 hours in PBS at room temperature. The reactions were stopped by addition of Tris buffer and immediately dialyzed to TBS to remove excess of biotin. The protein concentration was then determined by BCA protein assay (Pierce) and the biotin concentration was determined by Biotin TRF-PINCER assay (Mediomics). The following biotinylation levels were reached: a. 2 biotins on each antibody (5404 and 5405); b. 5 biotins on antibody 5404 and 3.5 biotins on antibody 5405; c. more than 10 biotins on each antibody (5404 and 5405).

Streptavidin-A2 Conjugation: Streptavidin was modified with oligonucleotide A2 through PEG12 linker following the standard chemical procedure described previously. The resulting conjugate has A2 to SA molar ratio of 1.4:1.

PINCER preparation: PINCER A (or B) was prepared by mixing biotinylated antibody 5404 (or 5405 for PINCER B) with SA-A2 and probe AA2-Eu (or AM-Alexa647 for PINCER B) at 1:1:1.4:1 (Ab:SA:A2:probe), 1.6:1:1.4:1, and 1.3:1.3:1.8:1 molar ratio at room temperature for 2 hours.

PINCER assay performance: hCRP protein was diluted in 10 ul reaction buffer (TBS with 0.2 mg/ml BSA, 0.05% Tween-20, and 0.02% NaN3). 10 ul of 2×PINCER mix (20 nM of PINCER A and 25 nM of PINCER B) was mixed with the antigen solution. The reactions were incubated at room temperature for 30 min and the fluorescence emission at 665 nM (TRF) and 620 nM (Donor) with excitation at 330 nM were recorded on a Synergy 4 plate reader (Biotek).

Figure 3:
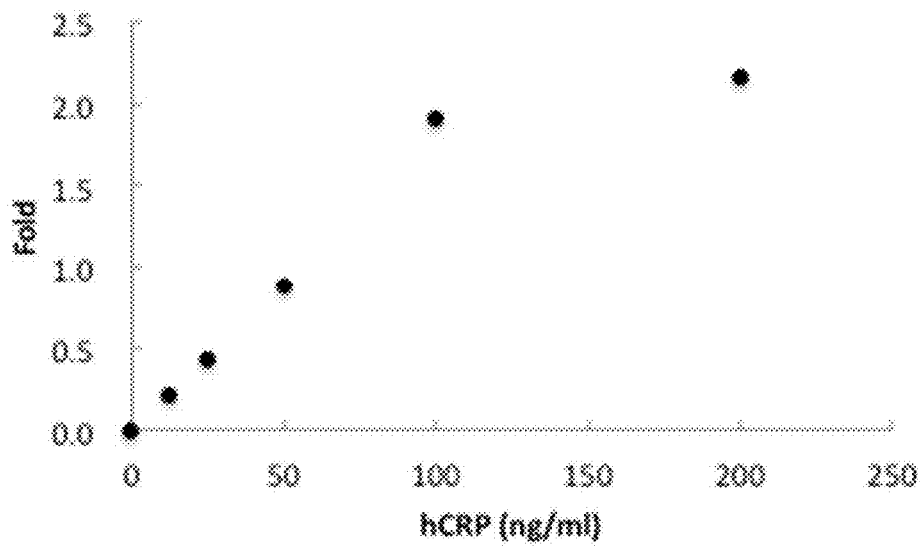
FIG. 3 is a graph depicting an hCRP standard curve with biotinylation level at >10:1 (Biotin: anti-hCRP antibody). hCRP concentration (ng/ml) is across the x-axis and fold change in signal is on the y-axis. Molecular biosensors were prepared under a single condition: Ab:SA:A2:probe=1.3:1.3:1.8:1.

When there were more than 10 biotins on each antibody, and the ratio of each components was 1.3:1.3:1.8:1, the FRET signal increased with increasing concentration of hCRP until 200 ng/ml, then the signal dropped due to competition of PINCER by excess of hCRP proteins. The overall signal change was 2 fold (Table 1, FIG. 3). This performance is very poor.

TABLE 1 hCRP standard curve with antibody biotinylation level at >10:1 (Biotin:Ab).

| | hCRP (ng/ml) | | | | | | | |
|---|---|---|---|---|---|---|---|---|
| | 0 | 12.5 | 25 | 50 | 100 | 200 | 400 | B0 |
| TRF | 2300 | 2746 | 3192 | 4154 | 6306 | 6778 | 4370 | 105 |
| Donor | 14900 | 14754 | 14687 | 14569 | 14475 | 14301 | 13181 | 49 |
| Ratio | 0.15 | 0.18 | 0.21 | 0.28 | 0.43 | 0.47 | 0.32 | |
| Fold | 0.00 | 0.22 | 0.43 | 0.89 | 1.91 | 2.17 | 1.20 | |

Figure 4:
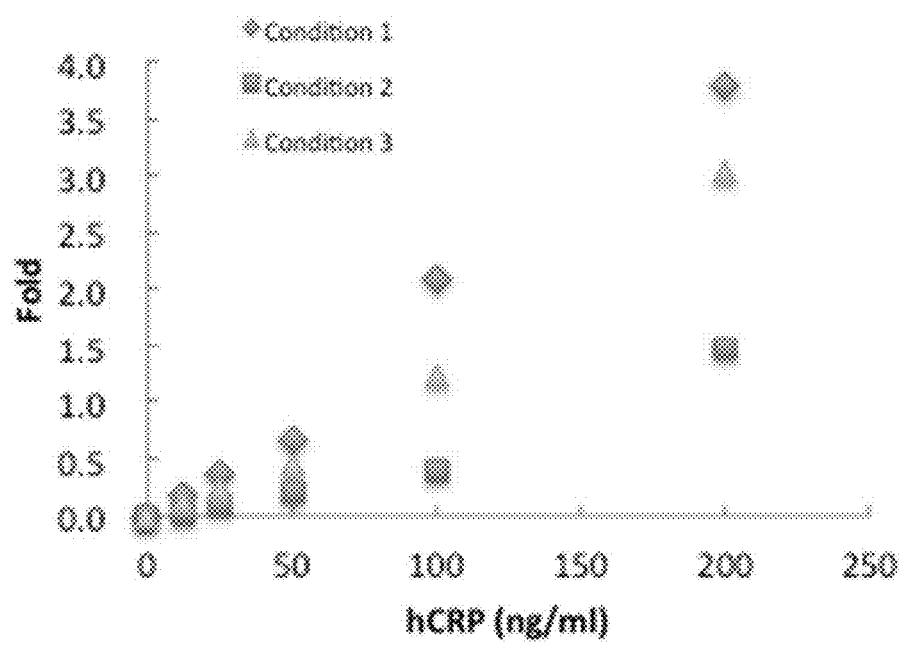
FIG. 4 is a graph depicting an hCRP standard curve with biotinylation level at ~4:1 (Biotin: anti-hCRP antibody). hCRP concentration (ng/ml) is across the x-axis and fold change in signal is on the y-axis. Molecular biosensors were prepared under three conditions: Condition 1: Ab:SA:A2:AA2 or AM=1:1:1.4:1; Condition 2. Ab:SA:A2:AA2 or AM=1.6:1:1.4:1; Condition 3: Ab:SA:A2:AA2 or AM=1.3:1.3:1.8:1. Ab=anti-hCRP antibody; SA=streptavidin; A2=flexible linker; AA2=first signaling oligonucleotide conjugated to probe; AM=second signaling oligonucleotide conjugated to probe.

When the biotinylation level decreased to about 4 biotins on each antibody, we prepared the PINCER under following conditions: 1. Ab:SA:A2:AA2 or AM=1:1:1.4:1; 2. Ab:SA:A2:AA2 or AM=1.6:1:1.4:1; 3: Ab:SA:A2:AA2 or AM=1.3:1.3:1.8:1. We noticed that when there was more than one antibody binding to one streptavidin, the assay performance dropped significantly, which could be due to the steric hindrance of the protein structure that interfered with the complex formation. When the A2 to probe ratio was lower than 1.4:1, the performance also dropped, which could be due to the excess of A2 and antibody that could not participate in the complex formation. When the antibodies were less biotinylated, the assay performance was better than using higher biotinylated antibodies under the same condition, which could be due to less interference of the biotin with the antigen/antibody interaction (Table 2, FIG. 4).

TABLE 2 hCRP standard curve with antibody biotinylation level at ~4:1 (Biotin:Ab)

| | | hCRP (ng/ml) | | | | | | | |
|---|---|---|---|---|---|---|---|---|---|
| | | 0 | 12.5 | 25 | 50 | 100 | 200 | 400 | B0 |
| Condition 1 | TRF | 2379 | 2711 | 3106 | 3783 | 6673 | 10194 | 5925 | 89 |
| | Donor | 14573 | 14230 | 14029 | 14141 | 13559 | 13510 | 13135 | 45 |
| | Ratio | 0.16 | 0.18 | 0.22 | 0.26 | 0.49 | 0.75 | 0.45 | |
| | Fold | 0.00 | 0.17 | 0.37 | 0.67 | 2.10 | 3.78 | 1.84 | |
| Condition 2 | TRF | 2506 | 2510 | 2722 | 2904 | 3433 | 5931 | 6385 | 114 |
| | Donor | 15260 | 15000 | 15185 | 14642 | 15229 | 15002 | 13905 | 48 |
| | Ratio | 0.16 | 0.16 | 0.17 | 0.19 | 0.22 | 0.39 | 0.45 | |
| | Fold | 0.00 | 0.02 | 0.10 | 0.21 | 0.39 | 1.47 | 1.87 | |
| Condition 3 | TRF | 2448 | 2683 | 2952 | 3400 | 5124 | 9088 | 4687 | 102 |
| | Donor | 14157 | 13762 | 14011 | 13725 | 13642 | 13456 | 12416 | 50 |

TABLE 2-continued hCRP standard curve with antibody biotinylation level at ~4:1 (Biotin:Ab)

| | hCRP (ng/ml) | | | | | | |
|---|---|---|---|---|---|---|---|
| | 0 | 12.5 | 25 | 50 | 100 | 200 | 400 | B0 |
| Ratio | 0.17 | 0.19 | 0.20 | 0.24 | 0.37 | 0.67 | 0.37 | |
| Fold | 0.00 | 0.13 | 0.23 | 0.42 | 1.22 | 30.03 | 1.23 | |

Figure 5:
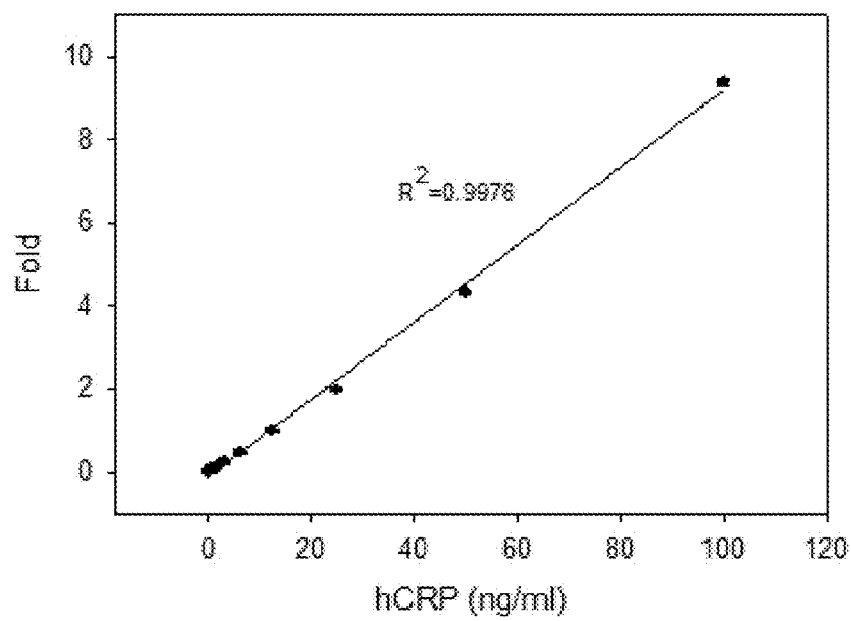
FIG. 5 is a graph depicting an hCRP standard curve with biotinylation level at ~2:1 (Biotin: anti-hCRP antibody). hCRP concentration (ng/ml) is across the x-axis and fold change in signal is on the y-axis. Molecular biosensors were prepared under a single condition: Ab:SA:A2:probe=1:1:1.4:1.

When biotinylation level was further decreased to 2 biotins on each antibody, the assay performance was significantly improved to the level that is similar to the original PINCER assay designs. When the ratio of each component was 1:1:1.4:1 (Ab:SA:A2:probe), the sensitivity and signal to background ratio was as good as TRF-PINCER assay (Table 3, FIG. 5). From the above studies, we concluded that the best PINCER assay performance could be reached when the antibodies were modified with biotin at 1:1 molar ratio, and the antibody:SA:probe ratio was 1:1:1. These conditions can also be applied to most antibody detections.

TABLE 3 hCRP standard curve with antibody biotinylation level at ~2:1 (Biotin:Ab).

| | hCRP (ng/ml) | | | | | | | | | | |
|---|---|---|---|---|---|---|---|---|---|---|---|
| | 0 | 0.78 | 1.56 | 3.125 | 6.25 | 12.5 | 25 | 50 | 100 | 200 | B0 |
| TRF | 2820 | 2971 | 3159 | 3242 | 3963 | 5313 | 7928 | 13361 | 24707 | 26162 | 170 |
| | 2753 | 3219 | 3147 | 3517 | 4045 | 5333 | 8088 | 13576 | 25339 | 27495 | 184 |
| | 2856 | 3063 | 2938 | 3627 | 4160 | 5565 | 7589 | 13562 | 25338 | 27949 | 162 |
| Donor | 15148 | 15068 | 15214 | 14893 | 14912 | 14897 | 14630 | 14147 | 13572 | 12888 | 46 |
| | 14873 | 14917 | 14871 | 14782 | 14780 | 14751 | 14541 | 14153 | 13534 | 13173 | 46 |
| | 14790 | 14921 | 14950 | 14833 | 14807 | 14767 | 14576 | 14196 | 13617 | 13178 | 50 |
| Fold (mean) | 0.00 | 0.10 | 0.10 | 0.25 | 0.48 | 1.00 | 1.98 | 4.31 | 9.39 | 10.67 | |
| Stderror | 0.01 | 0.03 | 0.03 | 0.05 | 0.02 | 0.03 | 0.06 | 0.03 | 0.09 | 0.15 | |

Example 3

HCV Core 1b Antibody PINCER Assay Using In Vivo Biotinylated Core 1b Protein PINCER Streptavidin-A2 (SA-A2) was prepared by modifying SA with oligo A2 through PEG12 linker following the standard chemical modification procedure. The modified SA-A2 was purified by gel filtration chromatography and the concentrations of SA and A2 were estimated from OD 260 absorbance and BCA protein assay, respectively. The estimated A2 to SA molar ratio is 1.8:1.

Figure 6:
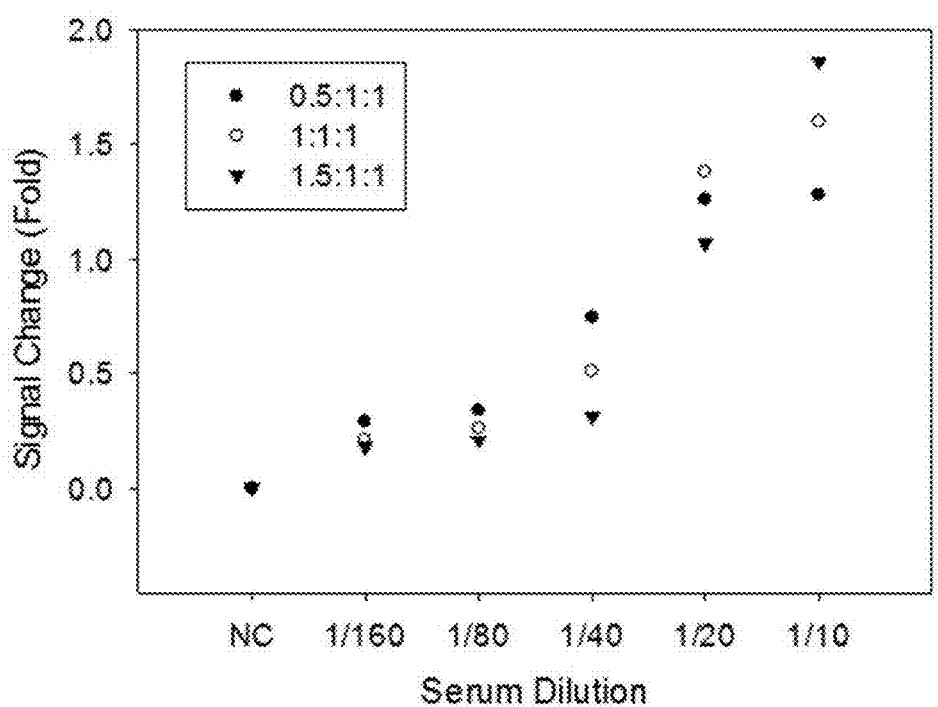
FIG. 6 is a graph depicting the standard curve for HCV core 1 b antibody PINCER assay using in vivo biotinylated core 1 b protein PINCER.

PINCER A and B were prepared by mixing in vivo biotinylated HCV core 1 b protein (stored in PBS with 2 M urea) with SA-A2 and probe (AA2-Eu or AM-647) at 0.5:1:1 (core 1 b:SA:probe), 1:1:1, or 1.5:1:1 molar ratio in TBS/NaN3 (20 mM Tris, pH 8.0, 100 mM NaCl, 0.02% NaN3) with 0.2 mg/ml BSA and 10% glycerol at room temperature for 1.5 hr. The prepared PINCERs were stored on ice until use. Anti-HCV core 1a chicken serum was serially diluted in reaction buffer (20 mM Tris, pH 8.0, 100 mM NaCl, 0.2 mg/ml BSA, 0.02% NaN3). 10 µl of the diluted sera were mixed with 10 µl of the 2×PINCER assay solution (20 nM PINCER A and 25 nM PINCER B in reaction buffer). The reactions were incubated at room temperature for 30 minutes. The fluorescence intensity at ~665 nm for the TRF signal (excitation at ~330 nm) and the fluorescence intensity at ~620 nm for the donor signal (excitation at ~330 nm) were recorded on a Synergy 4 plate reader (Biotek). Table 4, FIG. 6.

TABLE 4

Raw data for the HCV core 1b antibody PINCER assay using in vivo biotinylated core 1b protein PINCER.

| | | Anti-core 1a serum dilution | | | | | | |
|---|---|---|---|---|---|---|---|---|
| | | NC | 1/160 | 1/80 | 1/40 | 1/20 | 1/10 | B0 |
| TRF | 0.5:1:1 | 3038 | 3830 | 3905 | 4867 | 5873 | 5689 | 105 |
| | 1:1:1 | 3397 | 3852 | 3891 | 4293 | 6369 | 6653 | |
| | 1.5:1:1 | 3090 | 3553 | 3649 | 3636 | 5221 | 6647 | |
| Donor | 0.5:1:1 | 14228 | 14036 | 13720 | 13206 | 12370 | 11904 | 45 |
| | 1:1:1 | 15830 | 14872 | 14445 | 13323 | 12689 | 12132 | |
| | 1.5:1:1 | 14976 | 14605 | 14645 | 13484 | 12392 | 11499 | |
| ratio | 0.5:1:1 | 0.21 | 0.27 | 0.28 | 0.36 | 0.47 | 0.47 | |
| | 1:1:1 | 0.21 | 0.25 | 0.26 | 0.32 | 0.50 | 0.54 | |
| | 1.5:1:1 | 0.20 | 0.24 | 0.26 | 0.26 | 0.41 | 0.57 | |
| fold | 0.5:1:1 | 0.00 | 0.29 | 0.34 | 0.75 | 1.26 | 1.28 | |
| | 1:1:1 | 0.00 | 0.21 | 0.26 | 0.51 | 1.38 | 1.60 | |
| | 1.5:1:1 | 0.00 | 0.18 | 0.21 | 0.31 | 1.07 | 1.86 | |

Example 4

Figure 7:
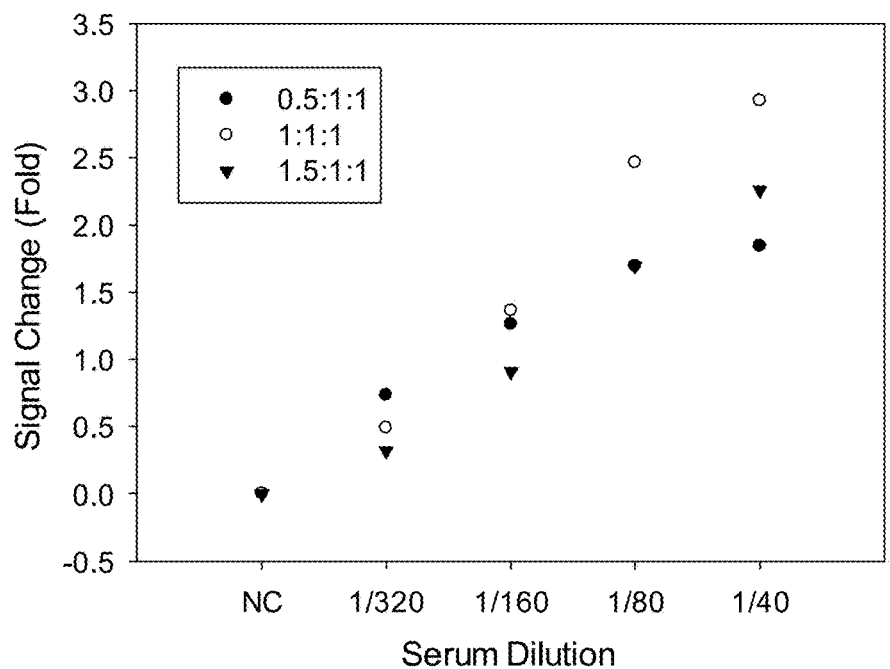
FIG. 7 is a graph depicting the standard curve for HCV c200 antibody PINCER assay using in vivo biotinylated c200 protein PINCER.

HCV C200 Antibody PINCER Assay Using In Vivo Biotinylated C200 Protein PINCER PINCER A and B were prepared by mixing in vivo biotinylated C200 protein (stored in PBS with 2 M urea) with SA-A2 and probe (AA2-Eu or AM-647) at 0.5:1:1 (C200:SA:probe), 1:1:1, or 1.5:1:1 molar ratio in TBS/NaN3 with 0.2 mg/ml BSA and 10% glycerol at room temperature for 1.5 hr. The prepared PINCERs were stored on ice until use. Anti-C200 chicken serum was serially diluted in reaction buffer (20 mM Tris, pH 8.0, 100 mM NaCl, 0.2 mg/ml BSA, 0.02% NaN3). 10 µl of the diluted sera were mixed with 10 µl of the 2×PINCER assay solution (20 nM PINCER A and 25 nM PINCER B in reaction buffer). The reactions were incubated at room temperature for 30 minutes. The fluorescence intensity at ~665 nm for the TRF signal (excitation at ~330 nm) and the fluorescence intensity at ~620 nm for the donor signal (excitation at ~330 nm) were recorded on a Synergy 4 plate reader (Biotek). Table 5, FIG. 7.

TABLE 5

Raw data for the HCV c200 antibody PINCER assay using in vivo biotinylated c200 protein PINCER.

| | | Anti-C200 serum dilution | | | | |
|---|---|---|---|---|---|---|
| | | NC | 1/320 | 1/160 | 1/80 | 1/40 |
| 0.5:1:1 | TRF | 2543 | 4273 | 5524 | 6607 | 3687 |
| | Donor | 13478 | 13278 | 13223 | 13307 | 13056 |
| 1:1:1 | TRF | 2293 | 3281 | 5202 | 7555 | 8539 |
| | Donor | 12806 | 12472 | 12604 | 12562 | 12546 |
| 1.5:1:1 | TRF | 2179 | 2827 | 4080 | 5661 | 6857 |
| | Donor | 12817 | 12770 | 12862 | 12716 | 12777 |
| Ratio | 0.5:1:1 | 0.18 | 0.32 | 0.41 | 0.49 | 0.52 |
| | 1:1:1 | 0.17 | 0.26 | 0.41 | 0.60 | 0.68 |
| | 1.5:1:1 | 0.16 | 0.21 | 0.31 | 0.44 | 0.53 |
| Fold | 0.5:1:1 | 0.00 | 0.73 | 1.26 | 1.70 | 1.85 |
| | 1:1:1 | 0.00 | 0.49 | 1.36 | 2.47 | 2.93 |
| | 1.5:1:1 | 0.00 | 0.32 | 0.91 | 1.70 | 2.26 |

Example 5

HCV NS4 Antibody PINCER Assay Using In Vivo Biotinylated NS4 Protein PINCER

Figure 8:
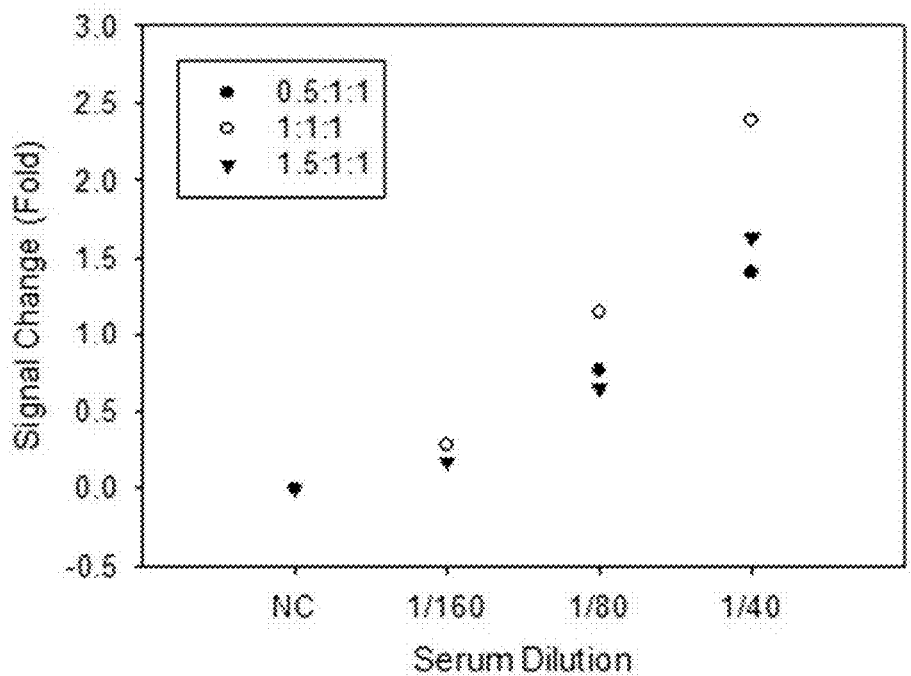
FIG. 8 is a graph depicting the standard curve for HCV NS4 antibody PINCER assay using in vivo biotinylated NS4 protein PINCER.

PINCER A and B were prepared by mixing in vivo biotinylated HCV NS4 protein (stored in PBS) with SA-A2 and probe (AA2-Eu or AM-647) at 0.5:1:1 (NS4:SA:probe), 1:1:1, or 1.5:1:1 molar ratio in TBS/NaN3 with 0.2 mg/ml BSA and 10% glycerol at room temperature for 1.5 hr. The prepared PINCERs were stored on ice until use. Anti-NS4 chicken serum was serially diluted in reaction buffer (20 mM Tris, pH 8.0, 100 mM NaCl, 0.2 mg/ml BSA, 0.02% NaN3). 10 µl of the diluted sera were mixed with 10 µl of the 2×PINCER assay solution (20 nM PINCER A and 25 nM PINCER B in reaction buffer). The reactions were incubated at room temperature for 30 minutes. The fluorescence intensity at ~665 nm for the TRF signal (excitation at ~330 nm) and the fluorescence intensity at ~620 nm for the donor signal (excitation at ~330 nm) were recorded on a Synergy 4 plate reader (Biotek). Table 6, FIG. 8.

TABLE 6

Raw data for the HCV NS4 antibody PINCER assay using in vivo biotinylated NS4 protein PINCER.

| | | Serum | | | |
|---|---|---|---|---|---|
| | | None | 1/160 | 1/80 | 1/40 |
| 0.5:1:1 | TRF | 2586 | 3069 | 4215 | 5348 |
| | Donor | 15364 | 14350 | 14438 | 13464 |
| 1:1:1 | TRF | 2679 | 3359 | 5313 | 8216 |
| | Donor | 14711 | 14513 | 13827 | 13667 |
| 1.5:1:1 | TRF | 2657 | 2822 | 3788 | 5891 |
| | Donor | 14962 | 13573 | 13113 | 12871 |
| Ratio | 0.5:1:1 | 0.16 | 0.21 | 0.29 | 0.39 |
| | 1:1:1 | 0.18 | 0.23 | 0.38 | 0.60 |
| | 1.5:1:1 | 0.17 | 0.20 | 0.28 | 0.45 |
| Fold | 0.5:1:1 | 0.00 | 0.28 | 0.76 | 1.41 |
| | 1:1:1 | 0.00 | 0.28 | 1.15 | 2.39 |
| | 1.5:1:1 | 0.00 | 0.17 | 0.65 | 1.63 |

Example 6

HCV NS5 Antibody PINCER Assay Using In Vivo Biotinylated NS5 Protein PINCER

Figure 9:
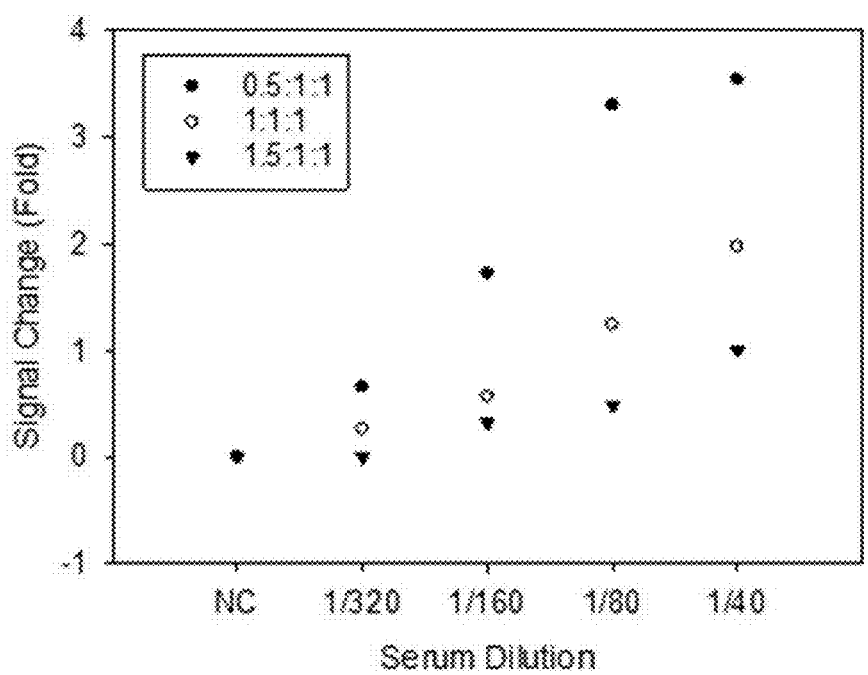
FIG. 9 is a graph depicting the standard curve for HCV NS5 antibody PINCER assay using in vivo biotinylated NS5 protein PINCER.

PINCER A and B were prepared by mixing in vivo biotinylated HCV NS5 protein with SA-A2 and probe (AA2-Eu or AM-647) at 0.5:1:1 (NS5:SA:probe), 1:1:1, or 1.5:1:1 molar ratio in TBS/NaN3 with 0.2 mg/ml BSA and 10% glycerol at room temperature for 1.5 hr. The prepared PINCERs were stored on ice until use. Anti-NS5 chicken serum was serially diluted in reaction buffer (20 mM Tris, pH 8.0, 100 mM NaCl, 0.2 mg/ml BSA, 0.05% Tween-20, 0.02% NaN3). 10 µl of the diluted sera were mixed with 10 µl of the 2×PINCER assay solution (20 nM PINCER A and 25 nM PINCER B in reaction buffer). The reactions were incubated at room temperature for 30 minutes. The fluorescence intensity at ~665 nm for the TRF signal (excitation at ~330 nm) and the fluorescence intensity at ~620 nm for the donor signal (excitation at ~330 nm) were recorded on a Synergy 4 plate reader (Biotek). Table 7, FIG. 9.

TABLE 7

Raw data for the HCV NS5 antibody PINCER assay using in vivo biotinylated NS5 protein PINCER.

| | | Anti-NS5 serum dilution | | | | |
|---|---|---|---|---|---|---|
| | | No serum | 1/320 | 1/160 | 1/80 | 1/40 |
| 0.5:1:1 | TRF | 2499 | 4049 | 6629 | 10036 | 10738 |
| | Donor | 13880 | 13783 | 13881 | 13371 | 13565 |
| 1:1:1 | TRF | 2307 | 2885 | 3497 | 4790 | 6173 |
| | Donor | 14724 | 14710 | 14484 | 13943 | 13606 |
| 1.5:1:1 | TRF | 2393 | 2400 | 3023 | 3395 | 4371 |
| | Donor | 14560 | 14627 | 14062 | 14076 | 13546 |
| Ratio | 0.5:1:1 | 0.17 | 0.29 | 0.47 | 0.75 | 0.79 |
| | 1:1:1 | 0.15 | 0.19 | 0.24 | 0.34 | 0.45 |
| | 1.5:1:1 | 0.16 | 0.16 | 0.21 | 0.23 | 0.32 |
| Fold | 0.5:1:1 | 0.00 | 0.66 | 1.72 | 3.30 | 3.54 |
| | 1:1:1 | 0.00 | 0.26 | 0.56 | 1.24 | 1.98 |
| | 1.5:1:1 | 0.00 | 0.00 | 0.32 | 0.49 | 1.00 |

Example 7

In Vitro Biotinylated HCV Protein PINCER Assay

In vitro biotinylation of NS4 and NS5. 300 µg of NS4 mosaic protein and NS5-1 b protein were each diluted to 1 mg/ml in PBS, pH 7.4. Biotin-LCLC-NHS (Pierce) was dissolved in DMSO and added to the protein solution at final 0.1 mM (12 fold molar excess of NS4 and 6 fold molar excess of NS5-1 b). The reactions were incubated at 22° C. for 30 min and stopped by addition of 1 µl 1M Tris, pH 8.0. The reactions were immediately dialyzed against TBS/NaN3 at 4° C. overnight. There was some precipitation in NS5-1 b in stock and in reaction. The precipitation was removed by centrifugation after dialysis.

Determine the protein concentrations and biotin levels. The protein concentrations were measure by OD 280 nm. The biotin levels were determined using Biotin TRF-PINCER assay.

Figure 10:
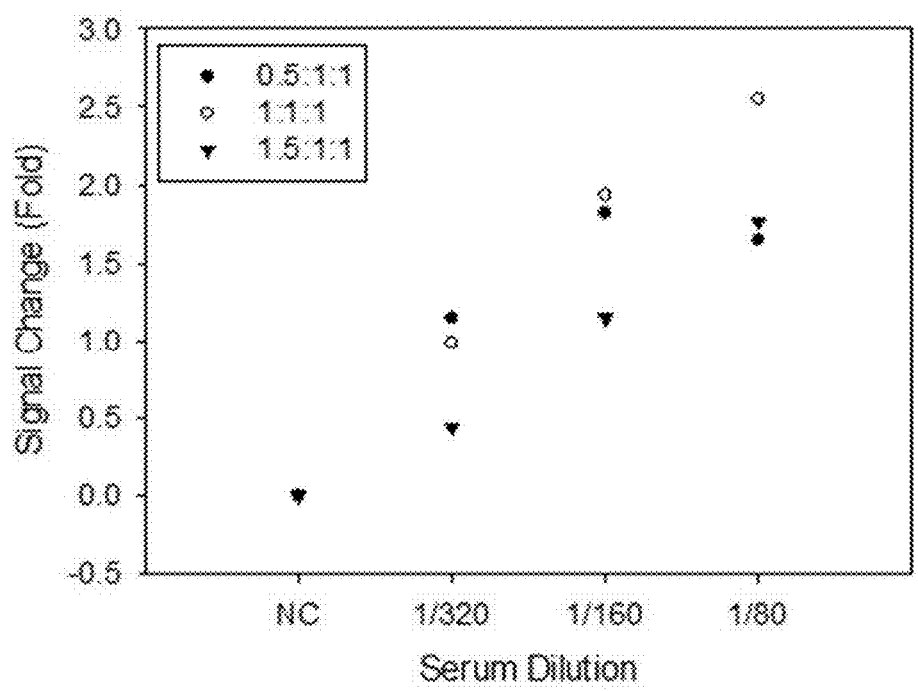
FIG. 10 is a graph depicting the standard curve for HCV NS5 antibody PINCER assay using in vitro biotinylated NS5 protein PINCER.

PINCER assay. PINCER A and B were prepared by mixing in vitro biotinylated HCV NS5 protein with SA-A2 and probe (AA2-Eu or AM-647) at 0.5:1:1 (NS5:SA:probe), 1:1:1, or 1.5:1:1 molar ratio in TBS/NaN3 with 0.2 mg/ml BSA and 10% glycerol at room temperature for 1.5 hr. The prepared PINCERs were stored on ice until use. Anti-NS5 chicken serum was serially diluted in reaction buffer (20 mM Tris, pH 8.0, 100 mM NaCl, 0.2 mg/ml BSA, 0.05% Tween-20, 0.02% NaN3). 10 µl of the diluted sera were mixed with 10 µl of the 2×PINCER assay solution (20 nM PINCER A and 25 nM PINCER B in reaction buffer). The reactions were incubated at room temperature for 30 minutes. The fluorescence intensity at ~665 nm for the TRF signal (excitation at ~330 nm) and the fluorescence intensity at ~620 nm for the donor signal (excitation at ~330 nm) were recorded on a Synergy 4 plate reader (Biotek). Table 8. FIG. 10.

Figure 11:
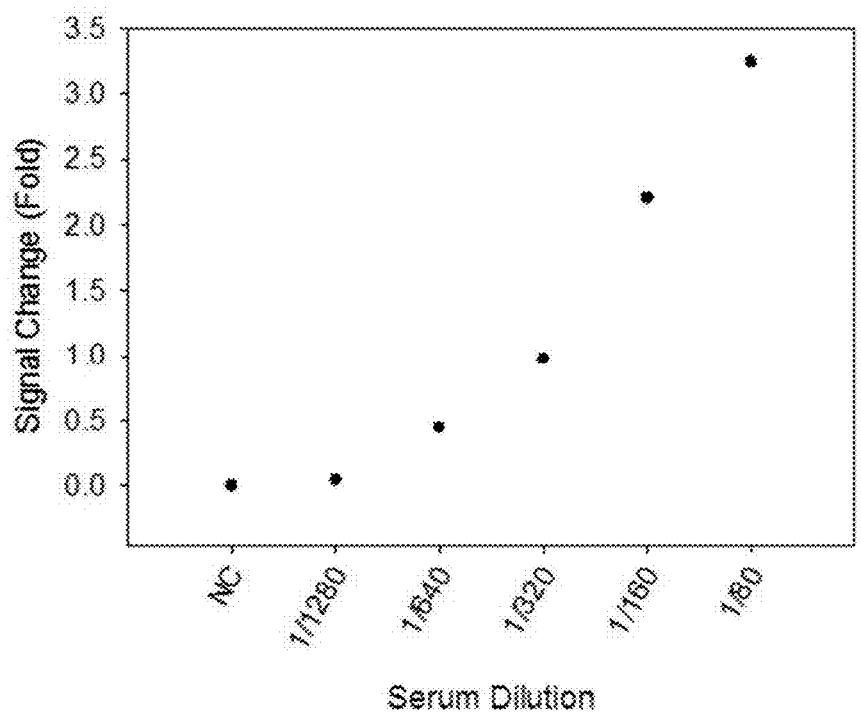
FIG. 11 is a graph depicting the standard curve for HCV NS4 antibody PINCER assay using in vitro biotinylated NS4 protein PINCER (using Eu/647 dye pair).
Figure 12:
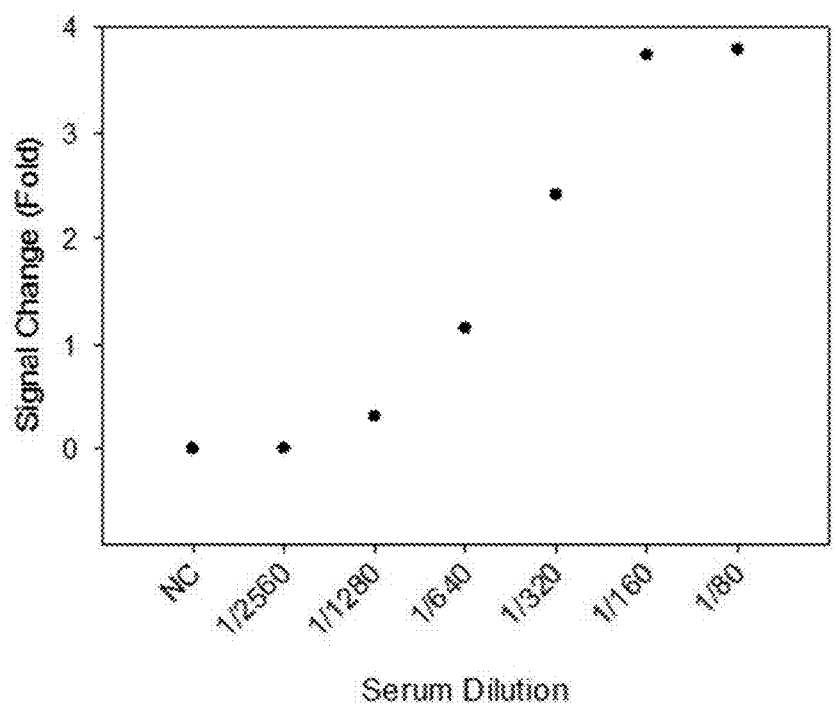
FIG. 12 is a graph depicting the standard curve for HCV NS5 antibody PINCER assay using in vitro biotinylated NS5 protein PINCER (using Eu/645 dye pair).

PINCER assays were also conducted using AA2-Eu/AM-match-5 Alexa probe pair. PINCER A and B were prepared by mixing in vitro biotinylated HCV NS4 and NS5 protein with SA-A2 and probe (AA2-Eu or AM-647) at 1:1:1 or 2:1:1 molar ratio in TBS/NaN3 with 0.2 mg/ml BSA and 10% glycerol at room temperature for 1.5 hr. The prepared PINCERs were stored on ice until use. Anti-NS4 or NS5 chicken serum was serially diluted in reaction buffer (20 mM Tris, pH 8.0, 100 mM NaCl, 0.2 mg/ml BSA, 0.05%, 0.02% NaN3). 10 µl of the diluted sera were mixed with 10 Dl of the 2×PINCER assay solution (20 nM PINCER A and 25 nM PINCER B in reaction buffer). The reactions were incubated at room temperature for 30 minutes. The fluorescence intensity at ~665 nm for the TRF signal (excitation at ~330 nm) and the fluorescence intensity at ~620 nm for the donor signal (excitation at ~330 nm) were recorded on a Synergy 4 plate reader (Biotek). Table 9, 10. FIGS. 11, 12.

TABLE 8

Raw data for the HCV NS5 antibody PINCER assay using in vitro biotinylated NS5 protein PINCER.

| | | Anti-NS5 serum | | | |
|---|---|---|---|---|---|
| | | No serum | 1/320 | 1/160 | 1/80 |
| 0.5:1:1 | TRF | 2731 | 5596 | 7501 | 7075 |
| | Donor | 14075 | 13706 | 14044 | 14108 |
| 1:1:1 | TRF | 2578 | 5093 | 7327 | 8854 |
| | Donor | 13940 | 14114 | 13857 | 13884 |
| 1.5:1:1 | TRF | 2839 | 3926 | 5740 | 7393 |
| | Donor | 15274 | 14839 | 14645 | 14705 |
| Ratio | 0.5:1:1 | 0.19 | 0.40 | 0.53 | 0.50 |
| | 1:1:1 | 0.18 | 0.36 | 0.52 | 0.63 |
| | 1.5:1:1 | 0.18 | 0.26 | 0.39 | 0.50 |
| Fold | 0.5:1:1 | 0.00 | 1.15 | 1.82 | 1.64 |
| | 1:1:1 | 0.00 | 0.99 | 1.93 | 2.55 |
| | 1.5:1:1 | 0.00 | 0.44 | 1.15 | 1.77 |

TABLE 9

Raw data for the HCV NS4 antibody PINCER assay using in vitro biotinylated NS4 protein PINCER (using Eu/647 dye pair)

| | Anti-sera dilution | | | | | |
|---|---|---|---|---|---|---|
| | No serum | 1280 | 640 | 320 | 160 | 80 |
| TRF | 2357 | 2422 | 3274 | 4329 | 6659 | 8495 |
| Donor | 12728 | 12566 | 12405 | 12064 | 11548 | 11171 |
| Ratio | 0.18 | 0.19 | 0.26 | 0.35 | 0.57 | 0.75 |
| Fold | 0.00 | 0.04 | 0.44 | 0.98 | 2.20 | 3.24 |

TABLE 10

Raw data for the HCV NS5 antibody PINCER assay using in vitro biotinylated NS5 protein PINCER (using Eu/645 dye pair)

| | Anti-sera dilution | | | | | | |
|---|---|---|---|---|---|---|---|
| | No serum | 2560 | 1280 | 640 | 320 | 160 | 80 |
| TRF | 3935 | 3790 | 4819 | 7532 | 11106 | 14734 | 14668 |
| Donor | 13562 | 12979 | 12750 | 12191 | 11420 | 10927 | 10766 |
| Ratio | 0.28 | 0.29 | 0.37 | 0.61 | 0.97 | 1.35 | 1.36 |
| Fold | .000 | 0.01 | 0.31 | 1.16 | 2.41 | 3.74 | 3.79 |

Example 8

Homogeneous PINCER Assay for Quick Detection of HCV Infection

Figure 22:
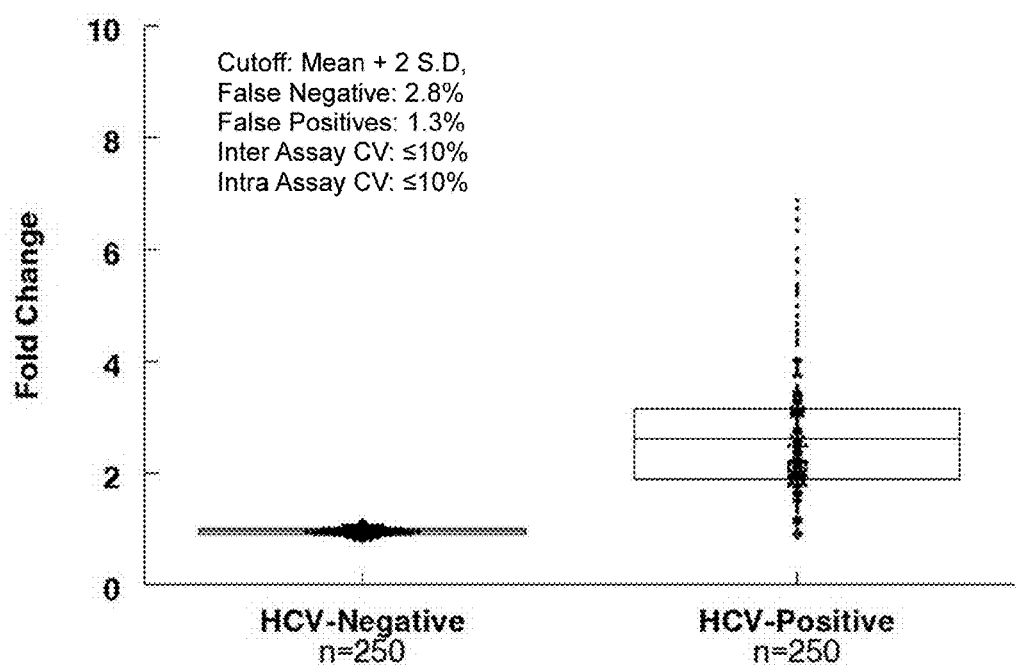
FIG. 22 is a graph depicting results from a homogeneous PINCER assay for quick detection of HCV infection using epitope-binding agent constructs with a modular design described herein. PINCER A and PINCER B for each HCV protein (core, c200, and NS5) were pooled and the homogenous HCV PINCER assay was performed on human serum samples as described in Example 8.

Streptavidin was conjugated to oligonucleotide A2 through bi-functional linker SMPEG12 following standard chemical conjugation procedures. PINCER A and PINCER B for each HCV protein (core, c200, and NS5) were pooled. Homogeneous HCV PINCER assay was performed as follows: chicken antisera and human serum samples were diluted to the indicated concentrations in 10 µl reaction buffer in a black 384 well low-volume microplate. 2×PINCER assay solution was prepared by mixing PINCER A and PINCER B for individual HCV protein or for all three antigens (core, c200, and NS5) in reaction buffer to a final concentration indicated in each experiment. 10 µl of the 2×PINCER assay solution was added to each well containing diluted serum. After the reactions were mixed and incubated at 24° C. for 30 min, time-resolved fluorescence emission at 665 nM was recorded with excitation wavelength at 330 nM and 55 µs delay, on a Synergy 4 plate reader (BioTek) for chicken serum samples, or on an Analyst HT plate reader (LJL Biosystems) for human serum samples. Fold of signal change was calculated using the following equation:

$$\text{Signal Change (Fold)} = (F_S - F_0)/(F_0 - F_B)$$

wherein $F_S$ is the fluorescence emission from reactions containing chicken test bleed or human serum sample; $F_0$ is the fluorescence emission from reactions containing buffer or human normal serum; $F_B$ is the fluorescence emission from buffer. Results are depicted in FIG. 22.

What is claimed is:

1. A molecular biosensor comprising two constructs, the two constructs which together have the formula (I):

$$(R_1-(X^1{}_1)_n)-X^2{}_1-R^2-R^3-R^4; \text{ and}$$

$$(R^5-(X^1{}_2)_m)-X^2{}_2-R^6-R^7-R^8; \quad (I)$$

wherein:
- $X^1{}_1$ and $X^2{}_1$ are a first affinity binding pair; wherein the affinity binding pair has at least a micromolar dissociation constant,
- $X^1{}_2$ and $X^2{}_2$ are a second affinity binding pair; wherein the affinity binding pair has at least a micromolar dissociation constant,
- n and m are each an integer from 1 to 2;
- $R^1$ is a first epitope binding agent that binds to a first epitope on a target molecule; wherein the first epitope binding agent is poorly soluble,
- $R^2$ is a flexible linker attaching $X^1{}_1$ to $R^3$;
- $R^3$ and $R^7$ comprise a pair of complementary nucleotide sequences such that $R^3$ and $R^7$ only associate when $R^1$ and $R^5$ remain bound to the target molecule in the presence of a denaturant;
- $R^4$ and $R^8$ together comprise a detection means such that when $R^3$ and $R^7$ associate a detectable signal is produced;
- $R^5$ is a second epitope binding agent that binds to a second epitope on the target molecule; and
- $R^6$ is a flexible linker attaching $X^2{}_2$ to $R^7$.

2. The molecular biosensor of claim 1, wherein $R^3$ and $R^7$ have a free energy association from about −5.5 kcal/mole to about −8.0 kcal/mole at a temperature from about 21° C. to about 40° C., and a salt concentration from about 1 mM to about 100 mM.

3. The molecular biosensor of claim 1, wherein $R^3$ and $R^7$ are independently from about 2 to about 20 nucleotides in length.

4. The molecular biosensor of claim 1, wherein the first and second affinity binding pair are identical.

5. The molecular biosensor of claim 1, wherein the first and second affinity binding pair are different.

6. The molecular biosensor of claim 1, wherein the first and second affinity binding pair consist of biotin and a biotin binding protein.

7. The molecular biosensor of claim 6, wherein the biotin binding protein is selected from the group consisting of avidin, deglycosylated avidin, native streptavidin and recombinant streptavidin.

8. The molecular biosensor of claim 1, wherein the target molecule is selected from the group consisting of a prion, a protein, a polypeptide, a peptide, an antigen, an antibody, a nucleic acid, a lipid, a carbohydrate, a biomolecule, a macromolecular complex, a fungus, and a microbial organism.

9. The molecular biosensor of claim 1, wherein the target molecule is selected from the group consisting of an antibody and an antigen.

10. The molecular biosensor of claim 1, wherein $R^1$ and $R^5$ are independently selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a protein, an antigen, a coenzyme, a coregulator, an allosteric molecule, and a small molecule.

11. The molecular biosensor of claim 1, wherein $R^1$ is a first antibody and $R^5$ is a second antibody, and wherein the first and second antibody specifically recognize a repeating epitope on the same target molecule.

12. The molecular biosensor of claim 1, wherein $R^1$ and $R^5$ are a Hepatitis C virus antigen.

13. The molecular biosensor of claim 1, wherein the detection means is selected from the group consisting of FRET, time resolved-FRET, fluorescence life-time imaging, fluorescence cross-correlation spectroscopy, fluorescence quenching, fluorescence polarization, flow cytometry, scintillation proximity, luminescense resonance energy transfer, direct quenching, ground-state complex formation, chemiluminescence energy transfer, bioluminescence resonance energy transfer, excimer formation, colorimetric substrates detection, phosphorescence, electro-chemical changes, residence time changes, and redox potential changes.

14. The molecular biosensor of claim 1, wherein the denaturant is selected from the group consisting of high temperature, high pH, organic solvents, urea, guanidinium chloride, sodium dodecyl sulfate (SDS), or Triton.

15. The molecular biosensor of claim 1, wherein the denaturant is about 0.1 M to about 1 M urea.

16. A method for detecting a target molecule, the method comprising contacting a sample comprising the target molecule with a molecular biosensor, the biosensor comprising:

$$(R^1\!-\!(X^1_{\ 1})_n)\!-\!X^2_{\ 1}\!-\!R^2\!-\!R^3\!-\!R^4; \text{ and}$$

$$(R^5\!-\!(X^1_{\ 2})_m)\!-\!X^2_{\ 2}\!-\!R^6\!-\!R^7\!-\!R^8;$$

wherein:
$X^1_{\ 1}$ and $X^2_{\ 1}$ are a first affinity binding pair; wherein the affinity binding pair has at least a micromolar dissociation constant, $X^1_{\ 2}$ and $X^2_{\ 2}$ are a second affinity binding pair; wherein the affinity binding pair has at least a micromolar dissociation constant, n and m are each an integer from 1 to 2;

$R^1$ is a first epitope binding agent that binds to a first epitope on a target molecule; wherein the first epitope binding agent is poorly soluble, $R^2$ is a flexible linker attaching $X^1_{\ 1}$ to $R^3$;

$R^3$ and $R^7$ comprise a pair of complementary nucleotide sequences such that $R^3$ and $R^7$ only associate when $R^1$ and $R^5$ remain bound to the target molecule in the presence of a denaturant;

$R^4$ and $R^8$ together comprise a detection means such that when $R^3$ and $R^7$ associate a detectable signal is produced;

$R^5$ is a second epitope binding agent that binds to a second epitope on the target molecule; and $R^6$ is a flexible linker attaching $X^2_{\ 2}$ to $R^7$; and detecting the signal produced by the association of $R^3$ with $R^7$.

17. The method for detecting the target molecule of claim 16, wherein $R^1$ and $R^5$ are independently selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a protein, an antigen, a coenzyme, a coregulator, an allosteric molecule, and a small molecule.

18. The molecular biosensor of claim 16, wherein the denaturant is selected from the group consisting of high temperature, high pH, organic solvents, urea, guanidinium chloride, sodium dodecyl sulfate (SDS), or Triton.

19. The molecular biosensor of claim 16, wherein the denaturant is about 0.1 M to about 1 M urea.

20. A molecular biosensor, the molecular biosensor comprising three constructs which together have the formula (III):

$$(R^{24}\!-\!(X^1_{\ 6})_n)\!-\!X^2_{\ 6}\!-\!R^{25}\!-\!R^{26}\!-\!R^{27};$$

$$(R^{28}\!-\!(X^1_{\ 7})_m)\!-\!X^2_{\ 7}\!-\!R^{29}\!-\!R^{30}\!-\!R^{31}; \text{ and}$$

$$O \qquad\qquad\qquad\qquad\qquad\qquad\qquad\qquad (III)$$

wherein:
$X^1_{\ 6}$ and $X^2_{\ 6}$ are a first affinity binding pair; wherein the affinity binding pair has at least a micromolar dissociation constant, $X^1_{\ 7}$ and $X^2_{\ 7}$ are a second affinity binding pair; wherein the affinity binding pair has at least a micromolar dissociation constant, n and m are each an integer from 1 to 2;

$R^{24}$ is an epitope binding agent that binds to a first epitope on a target molecule; wherein the first epitope binding agent is poorly soluble, $R^{25}$ is a flexible linker attaching $X^2_{\ 6}$ to $R^{26}$;

$R^{26}$ and $R^{30}$ comprise a pair of nucleotide sequences that are not complementary to each other, but are complementary to two distinct regions on O;

$R^{27}$ and $R^{31}$ together comprise a detection means such that when $R^{26}$ and $R^{30}$ associate with O, a detectable signal is produced;

$R^{28}$ is an epitope binding agent that binds to a second epitope on the target molecule;

$R^{29}$ is a flexible linker attaching $X^2_{\ 7}$ to $R^{30}$; and

O is a nucleotide sequence comprising a first region that is complementary to $R^{26}$, and a second region that is complementary to $R^{30}$.

21. The molecular biosensor of claim 20, wherein O comprises formula (IV):

$$R^{32}\!-\!R^{33}\!-\!R^{34}\!-\!R^{35}\!-\!R^{36} \qquad\qquad (IV)$$

wherein:
$R^{32}$, $R^{34}$, and $R^{36}$ are nucleotide sequences not complementary to any of $R^{26}$, $R^{30}$, $R^{33}$, or $R^{35}$;

$R^{33}$ is a nucleotide sequence complementary to $R^{26}$;

$R^{35}$ is a nucleotide sequence that is complementary to $R^{30}$; and $R^{33}$ is not adjacent to $R^{35}$.

22. The molecular biosensor of claim 21, wherein $R^{26}$ and $R^{33}$ and $R^{30}$ and $R^{35}$ have a free energy association from about −5.5 kcal/mole to about −8.0 kcal/mole at a temperature from about 21° C. to about 40° C., and a salt concentration from about 1 mM to about 100 mM.

23. The molecular biosensor of claim 20, wherein $R^{26}$ and $R^{30}$ are independently from about 2 to about 20 nucleotides in length.

24. The molecular biosensor of claim 20, wherein the first and second affinity binding pair consist of biotin and a biotin binding protein.

25. The molecular biosensor of claim 20, wherein the target molecule is selected from the group consisting of a prion, a protein, a polypeptide, a peptide, an antigen, an antibody, a nucleic acid, a lipid, a carbohydrate, a biomolecule, a macromolecular complex, a fungus, and a microbial organism.

* * * * *